(12) United States Patent
Kim et al.

(10) Patent No.: US 9,136,484 B2
(45) Date of Patent: Sep. 15, 2015

(54) COMPOUNDS FOR ORGANIC ELECTRONIC MATERIAL AND ORGANIC ELECTROLUMINESCENT DEVICE USING THE SAME

(75) Inventors: Hee-Sook Kim, Suwon-si (KR); Seok-Keun Yoon, Suwon-si (KR); Kyung-Joo Lee, Seoul (KR); Hong-Yoep Na, Seoul (KR); Nam-Kyun Kim, Suwon-si (KR); Young-Jun Cho, Seongnam-si (KR); Hyuck-Joo Kwon, Seoul (KR); Bong-Ok Kim, Seoul (KR)

(73) Assignee: Rohm and Haas Electronics Materials Korea Ltd., Cheonan-si (KR)

( * ) Notice: Subject to any disclaimer, the term of this patent is extended or adjusted under 35 U.S.C. 154(b) by 0 days.

(21) Appl. No.: 14/007,634

(22) PCT Filed: Mar. 23, 2012

(86) PCT No.: PCT/KR2012/002151
§ 371 (c)(1),
(2), (4) Date: Dec. 9, 2013

(87) PCT Pub. No.: WO2012/134124
PCT Pub. Date: Oct. 4, 2012

(65) Prior Publication Data
US 2014/0114069 A1 Apr. 24, 2014

(30) Foreign Application Priority Data

Mar. 25, 2011 (KR) ........................ 10-2011-0027070

(51) Int. Cl.
| | | |
|---|---|---|
| *H01L 51/00* | (2006.01) | |
| *C09K 11/06* | (2006.01) | |
| *H05B 33/20* | (2006.01) | |
| *C07D 405/14* | (2006.01) | |
| *C07D 403/04* | (2006.01) | |
| *C07D 403/14* | (2006.01) | |
| *C07D 409/14* | (2006.01) | |
| *C07F 7/08* | (2006.01) | |

(52) U.S. Cl.
CPC .......... *H01L 51/0072* (2013.01); *C07D 403/04* (2013.01); *C07D 403/14* (2013.01); *C07D 405/14* (2013.01); *C07D 409/14* (2013.01); *C07F 7/0812* (2013.01); *C09K 11/06* (2013.01); *H05B 33/20* (2013.01); *C09K 2211/1007* (2013.01); *C09K 2211/1029* (2013.01); *C09K 2211/1044* (2013.01); *C09K 2211/185* (2013.01); *H01L 51/0052* (2013.01); *H01L 51/0054* (2013.01); *H01L 51/0055* (2013.01); *H01L 51/0058* (2013.01); *H01L 51/0073* (2013.01); *H01L 51/0074* (2013.01); *H01L 51/0094* (2013.01); *Y02B 20/181* (2013.01)

(58) Field of Classification Search
CPC ............ H01L 51/0072; H01L 51/0073; H01L 51/0074
USPC .................................................. 544/229, 284
See application file for complete search history.

(56) References Cited

U.S. PATENT DOCUMENTS

| | | |
|---|---|---|
| 2011/0278555 A1 | 11/2011 | Inoue et al. |
| 2011/0279020 A1 | 11/2011 | Inoue et al. |
| 2012/0235123 A1 | 9/2012 | Lee et al. |

FOREIGN PATENT DOCUMENTS

| | | |
|---|---|---|
| KR | 20120013173 A | 2/2012 |
| WO | 2011019156 A1 | 2/2011 |
| WO | 2012036482 A1 | 3/2012 |

*Primary Examiner* — Paul V Ward
(74) *Attorney, Agent, or Firm* — Zhiqiang Zhao

(57) ABSTRACT

The present invention relates to electroluminescent compounds of formula 1 where A and/or B represent fluorene, carbazole, dibenzo[b,d]thiophene or dibenzo[b,d]furan derivatives and $L_1$, $X_1$, $Ar_1$, $Ar_2$, $R_5$, $R_6$ and $R_7$ are as defined herein, and organic electroluminescent devices comprising the same. The compounds according to the present invention have an advantage in manufacturing an organic electroluminescent device which has a high luminous efficiency and a long operational lifetime.

6 Claims, No Drawings

COMPOUNDS FOR ORGANIC ELECTRONIC MATERIAL AND ORGANIC ELECTROLUMINESCENT DEVICE USING THE SAME

FIELD OF THE INVENTION

The present invention relates to novel compounds for organic electronic material and an organic electroluminescent device using the same.

BACKGROUND OF THE INVENTION

An electroluminescent (EL) device is a self-light-emitting device which has advantages over other types of display devices in that it provides a wider viewing angle, a greater contrast ratio, and has a faster response time. An organic EL device was first developed by Eastman Kodak, by using small molecules which are aromatic diamines, and aluminum complexes as a material for forming a light-emitting layer [Appl. Phys. Lett. 51, 913, 1987].

The most important factor to determine luminous efficiency in an organic EL device is a light-emitting material. Until now, fluorescent materials have been widely used as a light-emitting material. However, in view of electroluminescent mechanisms, phosphorescent materials theoretically show four (4) times higher luminous efficiency than fluorescent materials. Thus, recently, phosphorescent materials have been investigated. Iridium(III) complexes have been widely known as phosphorescent materials, including bis(2-(2'-benzothienyl)-pyridinato-N,C3')iridium(acetylacetonate) ((acac)Ir(btp)$_2$), tris(2-phenylpyridine)indium (Ir(ppy)$_3$) and bis(4,6-difluorophenylpyridinato-N,C2)picolinate iridium (Firpic) as red, green and blue materials, respectively.

In order to improve color purity, luminous efficiency and stability, light-emitting materials can be used as one prepared by mixing a dopant with a host material. In the host material/dopant system, the host material has a great influence on the efficiency and performance of an EL device, and thus is important.

At present, 4,4'-N,N'-dicarbazol-biphenyl (CBP) is the most widely known host material for phosphorescent substances. Further, Pioneer (Japan) et al. developed a high performance organic EL device employing, as a host material, bathocuproine (BCP) and aluminum(III)bis(2-methyl-8-quinolinate)(4-phenylphenolate) (BAlq) which had been a material used for a hole blocking layer.

Though these phosphorous host materials provide good light-emitting characteristics, they have the following disadvantages: (1) Due to their low glass transition temperature and poor thermal stability, their degradation may occur during a high-temperature deposition process in a vacuum. (2) The power efficiency of an organic EL device is given by [(π/voltage)×current efficiency], and the power efficiency is inversely proportional to the voltage, and thus the power efficiency should be high in order to reduce power consumption. Although an organic EL device comprising phosphorescent materials provides higher current efficiency (cd/A) than one comprising fluorescent materials, when the conventional materials such as BAlq or CBP are used as phosphorescent host materials, a significantly high driving voltage is necessary compared to an organic EL device using a fluorescent material. Thus, there is no merit in terms of power efficiency (lm/W). (3) Further, the operation lifetime of an organic EL device is short and luminous efficiency is still required to be improved.

International Patent Publication No. WO 2006/049013 discloses compounds for organic electroluminescent materials having a condensed bicyclic group as a backbone structure. However, it does not disclose a compound having a nitrogen-containing condensed bicyclic group, which is formed by condensing two 6-membered rings, a carbazolic group, and an aryl or heteroaryl group.

DISCLOSURE OF THE INVENTION

Technical Problem

The objective of the present invention is to provide a compound for organic electronic material, which has an excellent structure imparting high luminous efficiency and a long operation lifetime to a device, and having proper color coordination; and an organic electroluminescent device, which has high efficiency and a long lifetime, using said compounds.

Solution to Problem

The present inventors found that the above objective can be achieved by a compound represented by the following formula 1:

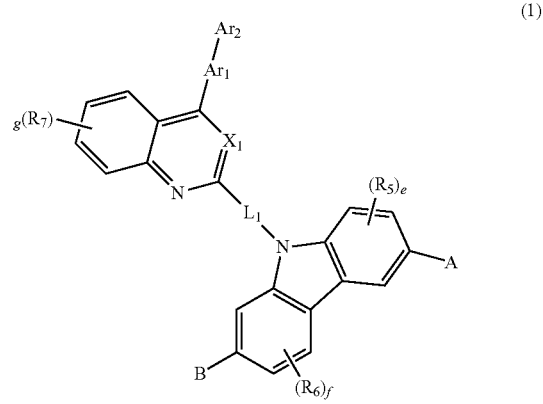

wherein
A represents hydrogen or

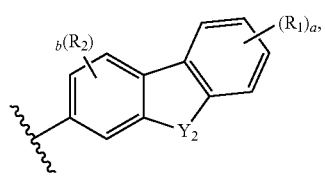

B represents hydrogen or

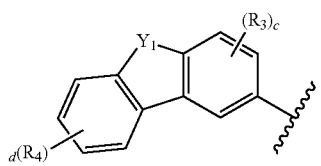

with the proviso that A and B are not simultaneously hydrogen;

$L_1$ represents a single bond, a substituted or unsubstituted 5- to 30-membered heteroarylene group, a substituted or unsubstituted (C6-C30)arylene group, or a substituted or unsubstituted (C6-C30)cycloalkylene group;

$X_1$ represents CH or N;

$Y_1$ and $Y_2$ each independently represent —O—, —S—, —$CR_8R_9$— or —$NR_{10}$—;

$Ar_1$ represents a single bond, a substituted or unsubstituted 5- to 30-membered heteroarylene group, a substituted or unsubstituted (C6-C30)arylene group, or a substituted or unsubstituted (C1-C30)alkylene group;

$Ar_2$ represents hydrogen, deuterium, a substituted or unsubstituted (C1-C30)alkyl group, a substituted or unsubstituted (C6-C30)aryl group, or a substituted or unsubstituted 3- to 30-membered heteroaryl group;

$R_1$ to $R_{10}$ each independently represent hydrogen, deuterium, a halogen, a substituted or unsubstituted (C1-C30)alkyl group, a substituted or unsubstituted (C6-C30)aryl group, a substituted or unsubstituted 3- to 30-membered heteroaryl group, a substituted or unsubstituted (C3-C30)cycloalkyl group, a substituted or unsubstituted 5- to 7-membered heterocycloalkyl group, a substituted or unsubstituted (C6-C30) aryl(C1-C30)alkyl group, a substituted or unsubstituted (C6-C30)aryl group fused with at least one (C3-C30)cycloalkyl group, a 5- to 7-membered heterocycloalkyl group fused with at least one substituted or unsubstituted (C6-C30)aromatic ring, a (C3-C30)cycloalkyl group fused with at least one substituted or unsubstituted (C6-C30)aromatic ring, —$NR_{11}R_{12}$, —$SiR_{13}R_{14}R_{15}$, —$SR_{16}$, —$OR_{17}$, a substituted or unsubstituted (C2-C30)alkenyl group, a substituted or unsubstituted (C2-C30)alkynyl group, a cyano group, a nitro group, or a hydroxyl group; or are linked to an adjacent substituent via a substituted or unsubstituted (C3-C30)alkylene or a (C3-C30)alkenylene group to form a mono- or polycyclic, alicyclic or aromatic ring whose carbon atom(s) may be replaced with at least one heteroatom selected from nitrogen, oxygen and sulfur;

$R_{11}$ to $R_{17}$ have the same definition as one of $R_1$ to $R_{10}$;

a, d and g each independently represent an integer of 1 to 4, where a, d or g is an integer of 2 or more, and each of $R_1$, each of $R_4$ or each of $R_7$ is the same or different;

b, c, e and f each independently represent an integer of 1 to 3, where b, c, e or f is an integer of 2 or more, and each of $R_2$, each of $R_3$, each of $R_5$ or each of $R_6$ is the same or different; and the heterocycloalkyl group and the heteroaryl(ene) group contain at least one heteroatom selected from B, N, O, S, P(=O), Si and P.

Advantageous Effects of Invention

The compounds for organic electronic material according to the present invention can manufacture an organic electroluminescent device which has high luminous efficiency and a long operation lifetime.

MODE FOR THE INVENTION

Hereinafter, the present invention will be described in detail. However, the following description is intended to explain the invention, and is not meant in any way to restrict the scope of the invention.

The present invention relates to a compound for organic electronic material represented by the above formula 1.

Herein, "(C1-C30)alkyl(ene)" is meant to be a linear or branched alkyl(ene) having 1 to 30 carbon atoms, in which the number of carbon atoms is preferably 1 to 20, more preferably 1 to 10, and includes methyl, ethyl, n-propyl, isopropyl, n-butyl, isobutyl, tert-butyl, etc.; "(C2-C30) alkenyl(ene)" is meant to be a linear or branched alkenyl(ene) having 2 to 30 carbon atoms, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc.; "(C2-C30)alkynyl" is a linear or branched alkynyl having 2 to 30 carbon atoms, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc.; "(C1-C30)alkoxy" is a linear or branched alkoxy having 1 to 30 carbon atoms, in which the number of carbon atoms is preferably 1 to 20, more preferably 1 to 10, and includes methoxy, ethoxy, propoxy, isopropoxy, 1-ethylpropoxy, etc.; "(C3-C30)cycloalkyl" is a mono- or polycyclic hydrocarbon having 3 to 30 carbon atoms, in which the number of carbon atoms is preferably 3 to 20, more preferably 3 to 7, and includes cyclopropyl, cyclobutyl, cyclopentyl, cyclohexyl, etc.; "(C6-C30)cycloalkylene" is one formed by removing a hydrogen from cycloalkyl having 6 to 30, preferably 6 to 20, more preferably 6 or 7 carbon atoms; and "5- to 7-membered heterocycloalkyl" is a cycloalkyl having at least one heteroatom selected from B, N, O, S, P(=O), Si and P, preferably N, O and S, and 5 to 7 ring backbone atoms, and includes tetrahydrofuran, pyrrolidine, thiolan, tetrahydropyran, etc.; "(C6-C30)aryl(ene)" is a monocyclic or fused ring derived from an aromatic hydrocarbon having 6 to 30 carbon atoms, in which the number of carbon atoms is preferably 6 to 20, more preferably 6 to 12, and includes phenyl, biphenyl, terphenyl, naphthyl, fluorenyl, phenanthrenyl, anthracenyl, indenyl, triphenylenyl, pyrenyl, tetracenyl, perylenyl, chrysenyl, naphthacenyl, fluoranthenyl, etc. Further, "3- to 30-membered heteroaryl(ene)" is an aryl having at least one, preferably 1 to 4 heteroatom selected from the group consisting of B, N, O, S, P(=O), Si and P, and 3 to 30 ring backbone atoms; is a monocyclic ring or fused ring condensed with at least one benzene ring; has preferably 5 to 21, more preferably 5 to 12 ring backbone atoms; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc. "Halogen" includes F, Cl, Br and I.

Herein, "substituted" in the expression "substituted or unsubstituted" means that a hydrogen atom in a certain functional group is replaced with another atom or group, i.e., a substituent. Substituents of the substituted (C1-C30)alkyl group, the substituted (C2-C30)alkenyl group, the substituted (C2-C30)alkynyl group, the substituted (C6-C30)cycloalkylene group, the substituted (C3-C30)cycloalkyl group, the substituted 5- to 7-membered heterocycloalkyl group, the substituted (C6-C30)aryl(ene) group, the substituted 5- to 30-membered heteroaryl(ene) group and the substituted aromatic ring in said $L_1$, $Ar_1$, $Ar_2$, $R_1$ to $R_{10}$ and $R_{11}$ to $R_{17}$ groups are each independently at least one selected from the group consisting of deuterium, a halogen, a (C1-C30)alkyl substituted or unsubstituted with a halogen, a (C6-C30)aryl, a 3- to 30-membered heteroaryl substituted or unsubstituted with a (C6-C30)aryl, a 5- to 7-membered heterocycloalkyl group, a 5- to 7-membered heterocycloalkyl group fused with at least one (C6-C12)aromatic ring, a (C3-C30)cycloalkyl group, a (C6-C30)cycloalkyl group fused with at least one (C6-C12) aromatic ring, $R_aR_bR_cSi-$, a (C2-C30)alkenyl group, a (C2-C30)alkynyl group, a cyano group, a carbazolyl group, $-NR_dR_e$, $-BR_fR_g$, $-PR_hR_i$, $-P(=O)R_jR_k$, a (C6-C30) aryl(C1-C30)alkyl group, a (C1-C30)alkyl(C6-C30)aryl group, $R_1Z-R_mC(=O)-$, $R_mC(=O)O-$, a carboxyl group, a nitro group and a hydroxyl group, wherein $R_a$ to $R_l$ each independently represent a (C1-C30)alkyl group, a (C6-C30)aryl group or a 3- to 30-membered heteroaryl group, or are linked to an adjacent substituent via a substituted or unsubstituted (C3-C30)alkylene or a (C3-C30)alkenylene group to form a mono- or polycyclic, alicyclic or aromatic ring whose carbon atom(s) may be replaced with at least one heteroatom selected from nitrogen, oxygen and sulfur; Z represents S or O; and $R_m$ represents a (C1-C30)alkyl group, a (C1-C30)alkoxy group, a (C6-C30)aryl group or a (C6-C30) aryloxy group.

In the above formula 1, L1 is preferably a single bond, a substituted or unsubstituted 5- to 12-membered heteroarylene group, or a substituted or unsubstituted (C6-C12) arylene group, more preferably one selected from group consisting of a single bond, phenylene, naphthylene, biphenylene, terphenylene, anthrylene, andenylene, fluorenylene, phenanthrylene, triphenylenylene, pyrenylene, phenylenylene, chrysenylene, naphthasenylene, fluorantenyl, furylene, thiophenylene, pyrrolylene, imidazolylene, pyrazolylene, thiazolylene, thiadiazolylene, isothiazolylene, isoxazolylene, oxazolylene, oxadiazolylene, triazinylene, tetrazinylene, triazolylene, tetrazolylene, furazanylene, pyridylene, pyrazinylene, pyrimidinylene, pyridazinylene, benzofuranylene, benzothiophenylene, isobenzofuranylene, benzoimidazolylene, benzothiazolylene, benzoisothiazolylene, benzoisoxazolylene, benzooxazolylene, isoindolylene, indolylene, indazolylene, benzothiadiazolylene, quinolylene, isoquinolylene, cinnolinylene, quinazolinylene, quinoxalinylene, carbazolylene, phenanthridinylene, benzodioxolylene, dibenzofuranylene and dibenzothiophenylene.

In the above formula 1, $Ar_1$ is preferably a single bond, a substituted or unsubstituted 5- to 21-membered heteroarylene group, or a substituted or unsubstituted (C6-C20) arylene group; and $Ar_2$ is preferably hydrogen, deuterium, a substituted or unsubstituted (C1-C10)alkyl group, a substituted or unsubstituted (C6-C20)aryl group, or a substituted or unsubstituted 5- to 21-membered heteroaryl group.

More specifically,

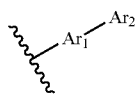

is selected from the following structures, but is not limited thereto:

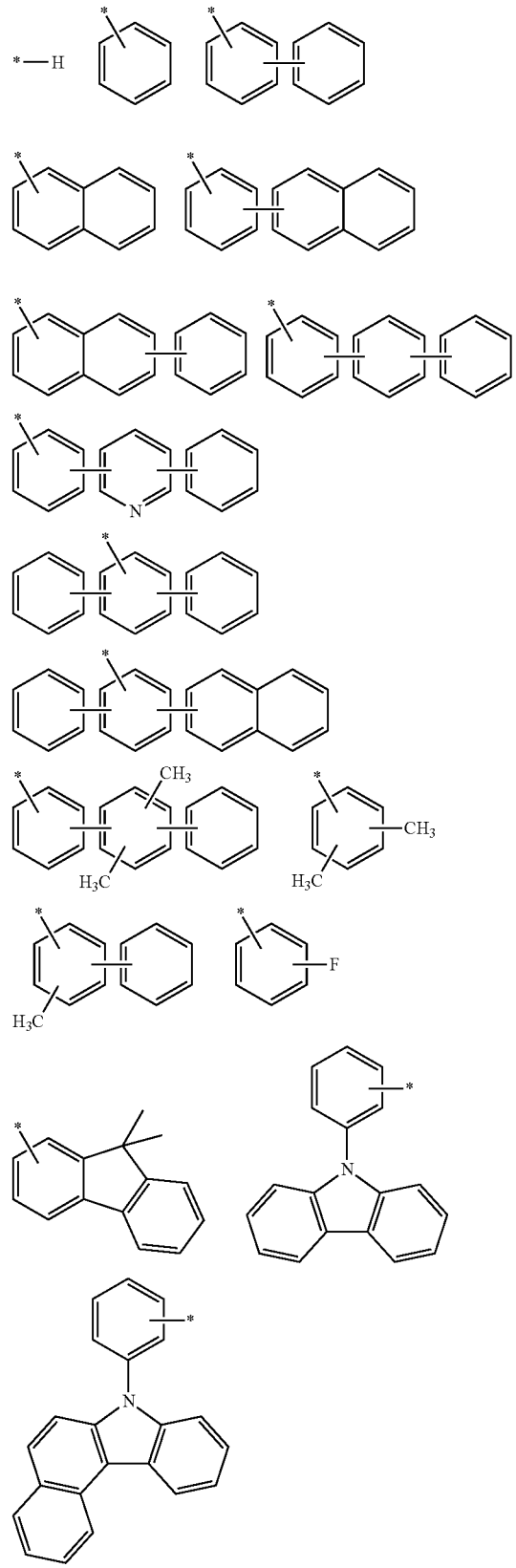

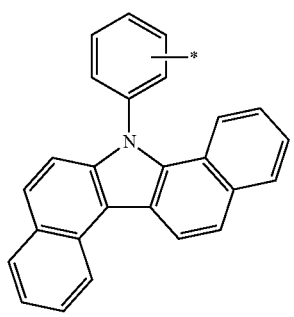
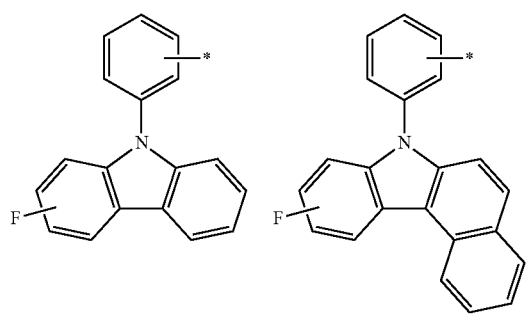
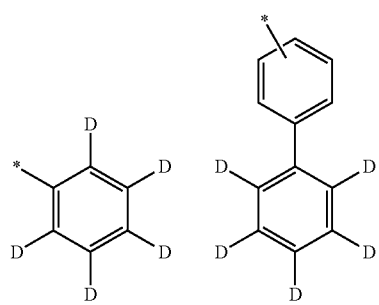
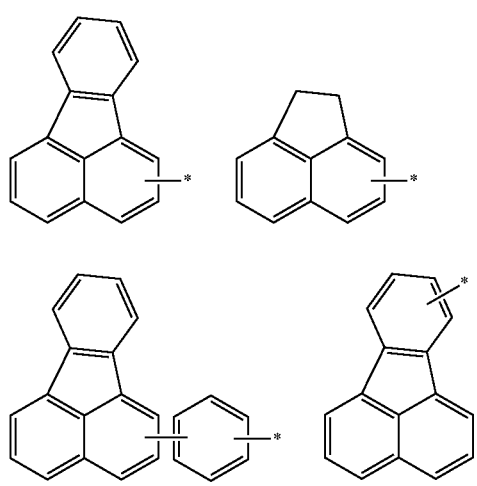
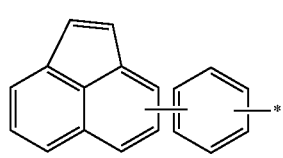

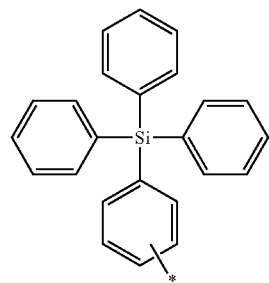
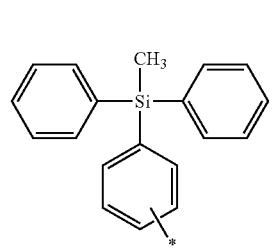
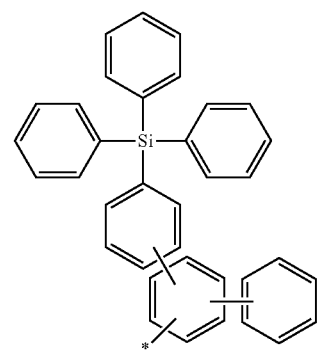
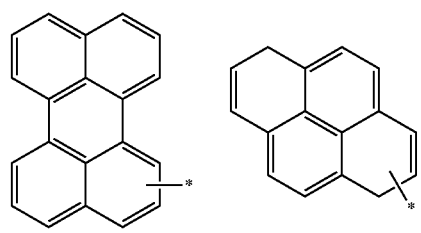

In the above formula 1, $R_1$ to $R_{10}$ are each independently preferably hydrogen, deuterium, a substituted or unsubstituted (C1-C10) alkyl group, a substituted or unsubstituted (C6-C12) aryl group, or a substituted or unsubstituted 5- to 12-membered heteroaryl group; more preferably, $R_1$ to $R_7$ are hydrogen, $R_8$ and $R_9$ is a substituted or unsubstituted (C1-C10)alkyl group, and $R_{10}$ is a substituted or unsubstituted (C6-C12)aryl group.

The representative compounds of the present invention include the following, but are not limited thereto:

C-1
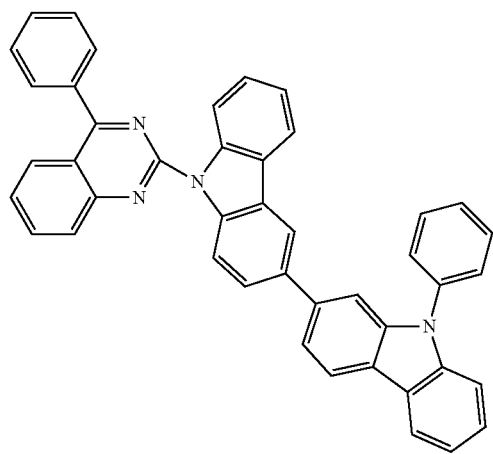
C-2
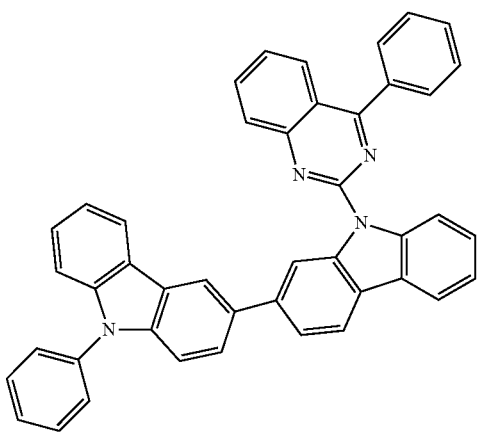
C-3
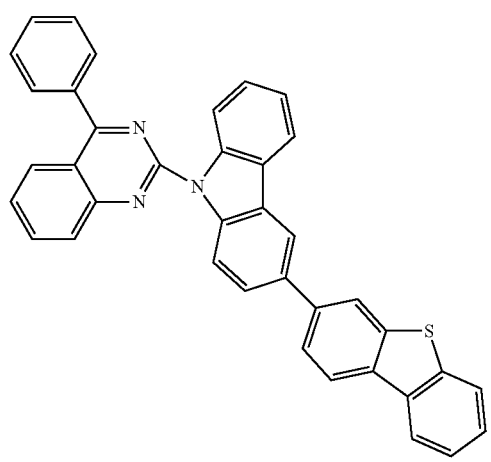
C-4
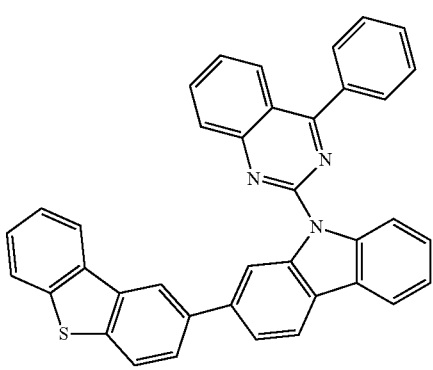
C-5
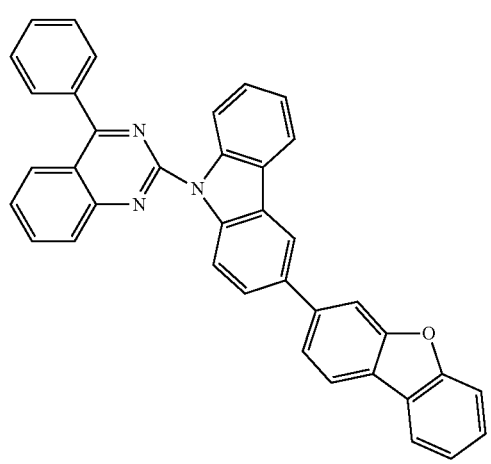
C-6
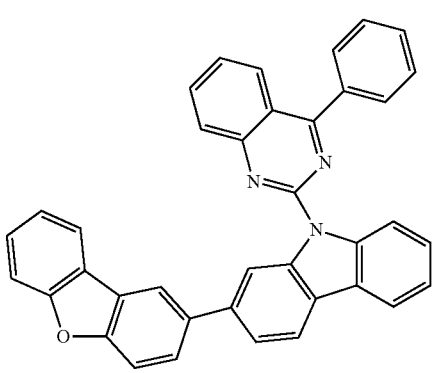

-continued
C-7
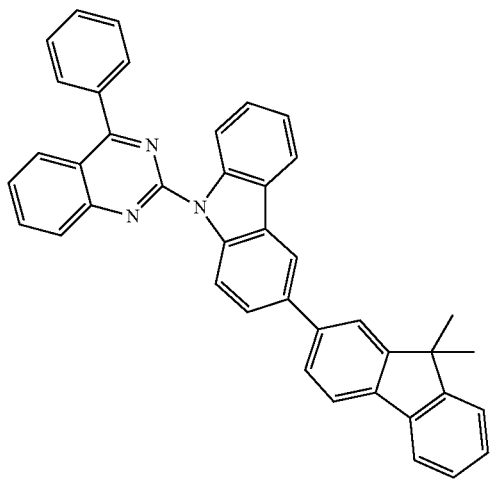
C-8
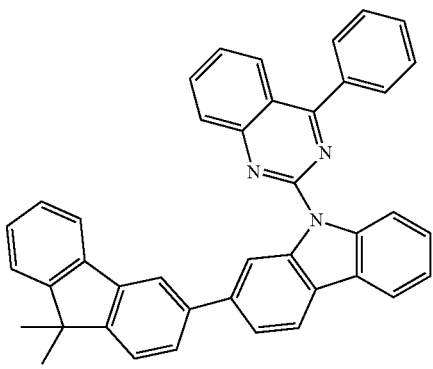
C-9
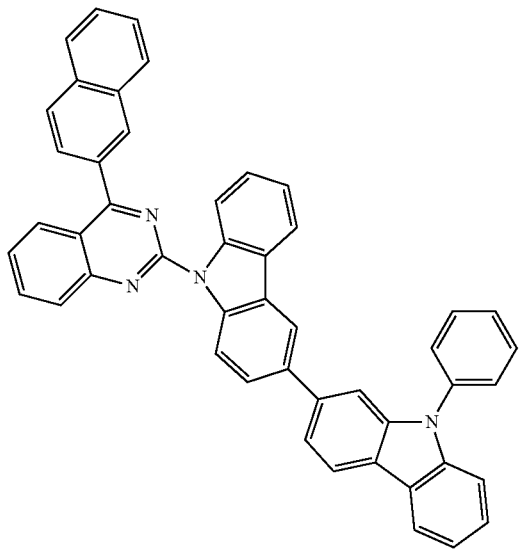
C-10
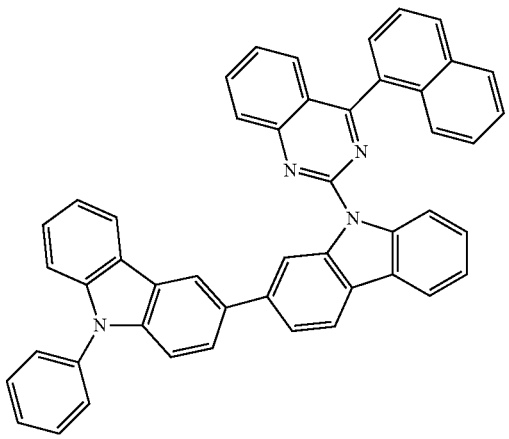
C-11
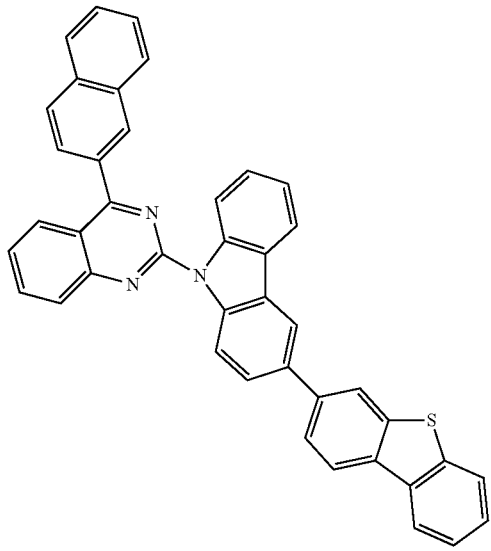
C-12
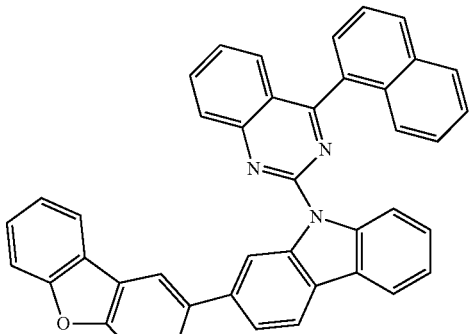

-continued
C-13
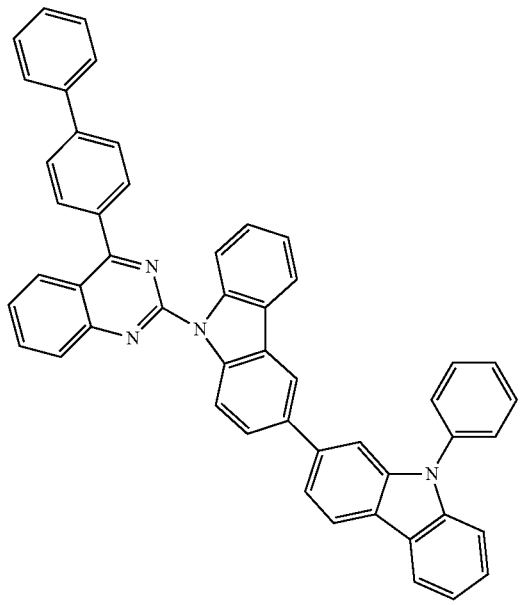
C-14
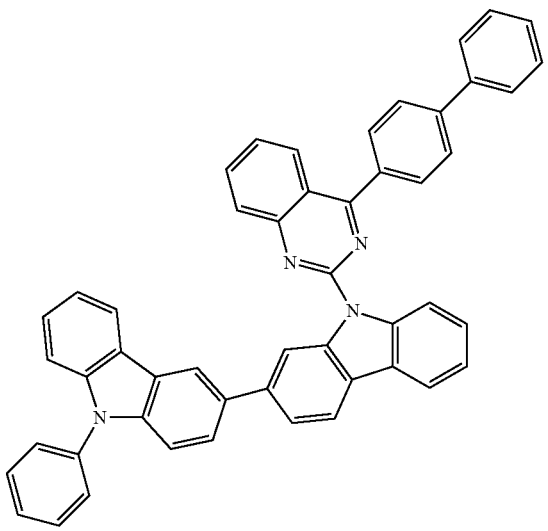
C-15
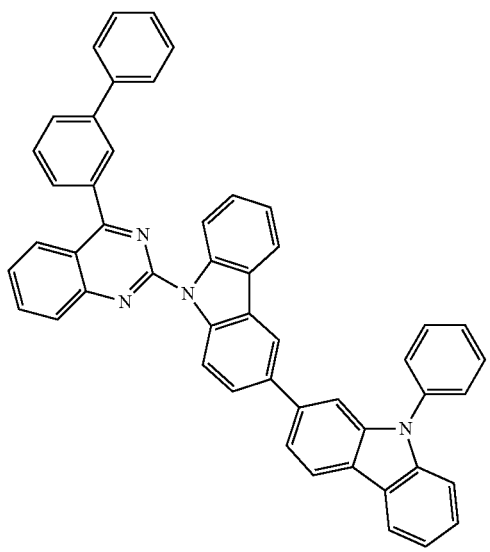
C-16
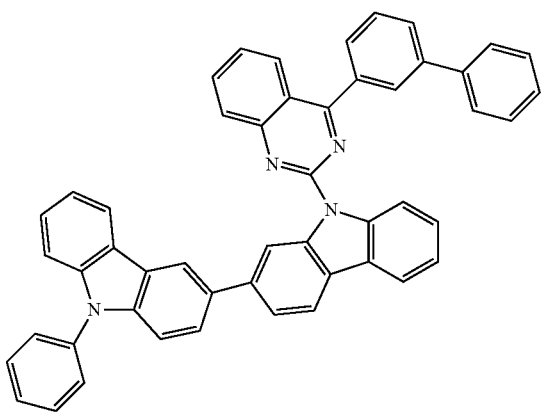
C-17
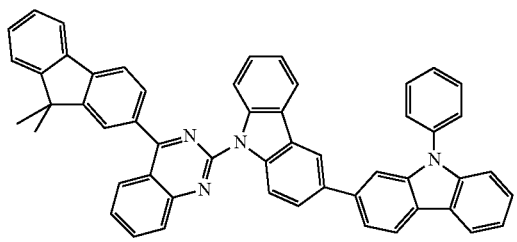
C-18
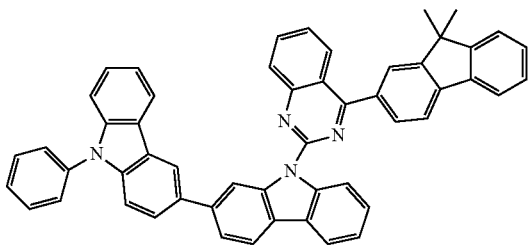

-continued
C-19
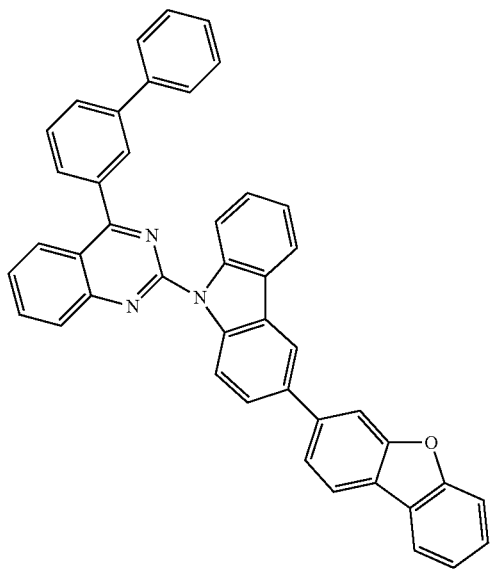
C-20
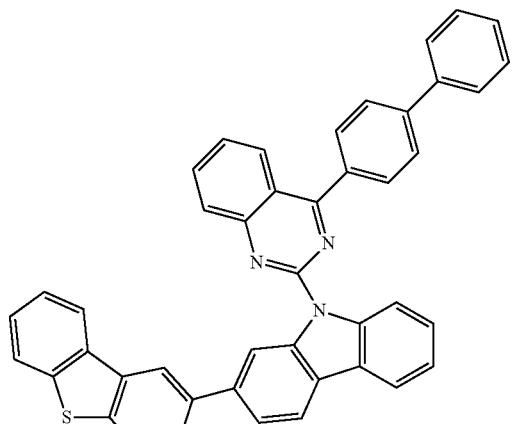
C-21
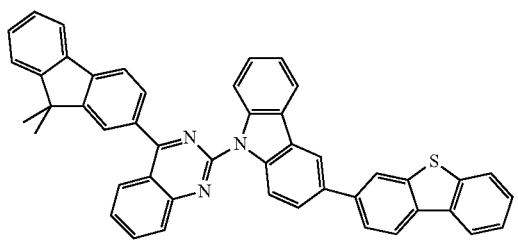
C-22
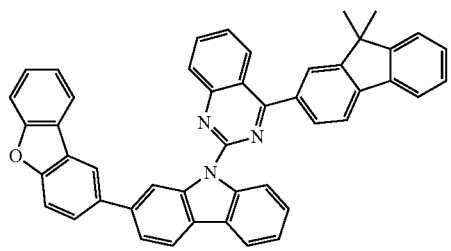
C-23
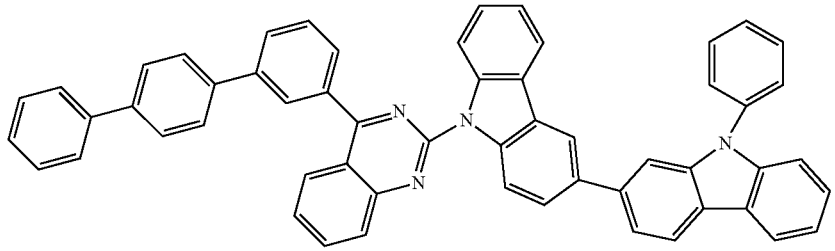
C-24
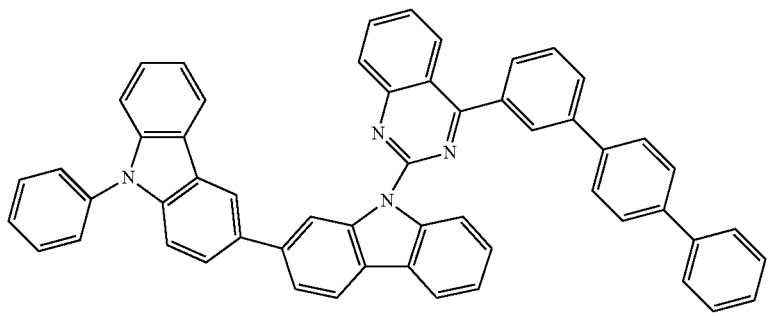
C-25
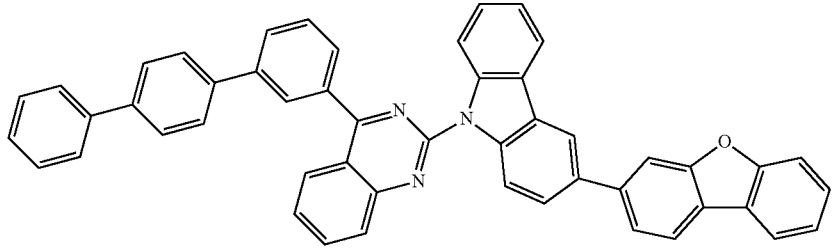

-continued
C-26
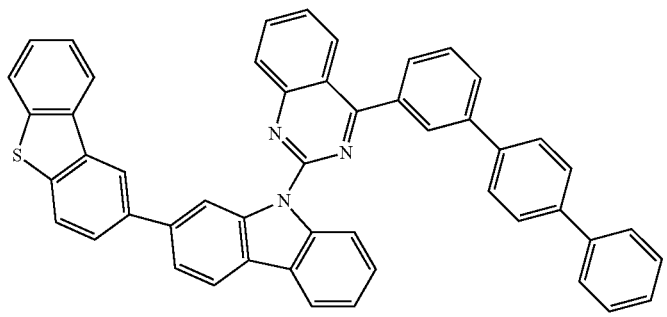
C-27
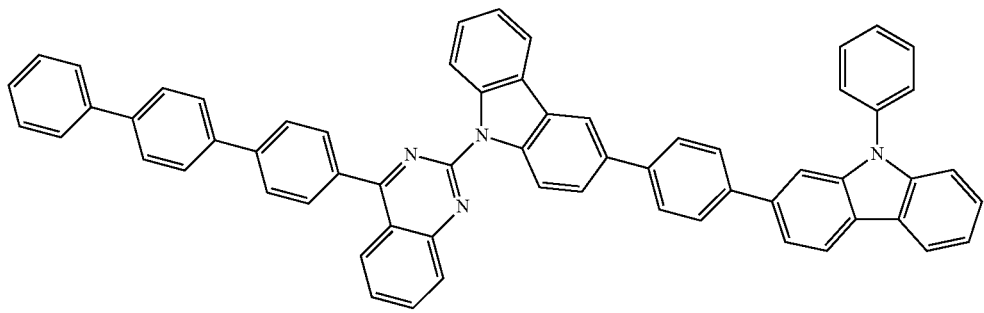
C-28
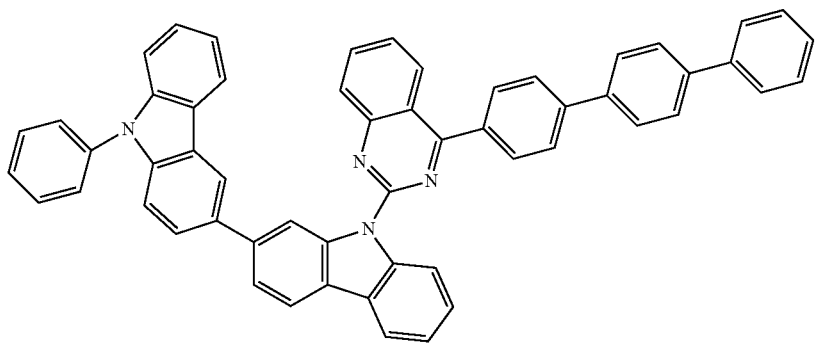
C-29
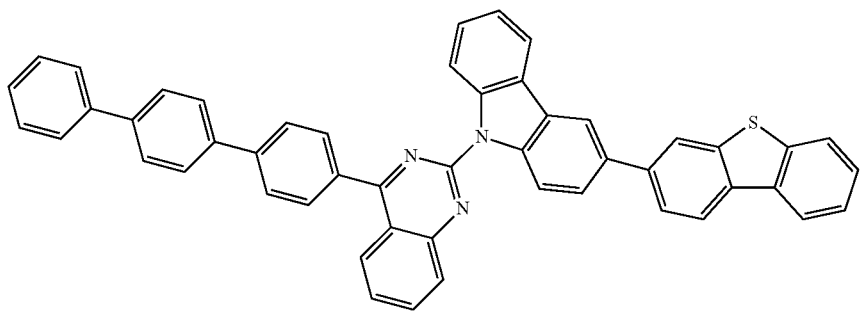
C-30
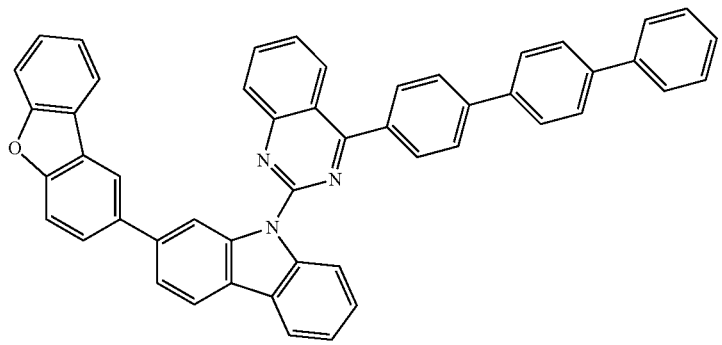

-continued
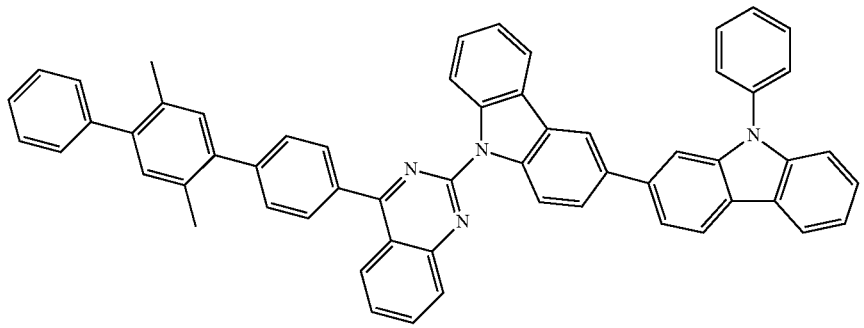
C-31
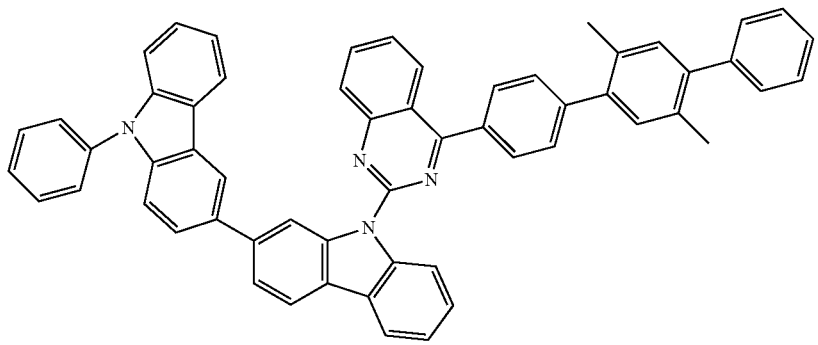
C-32
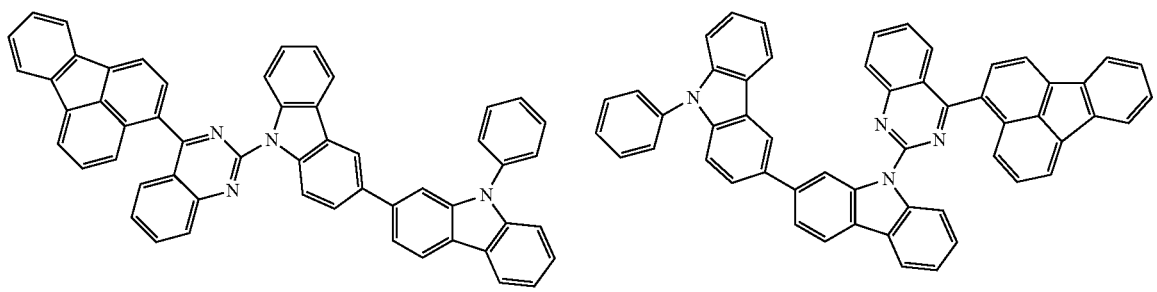
C-33          C-34
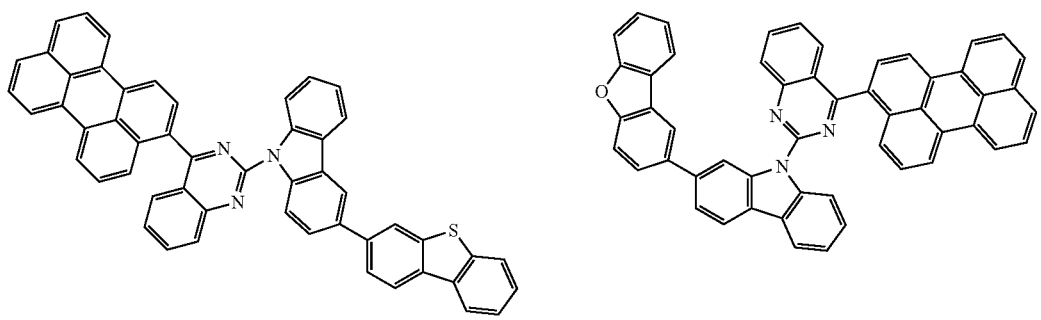
C-35          C-36

-continued
C-37
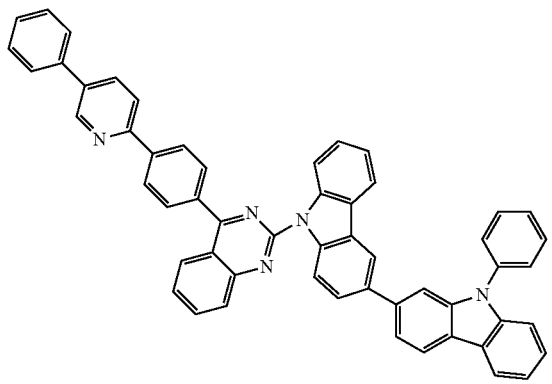
C-38
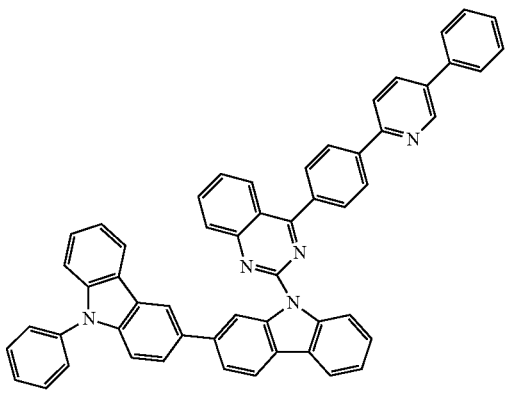
C-39
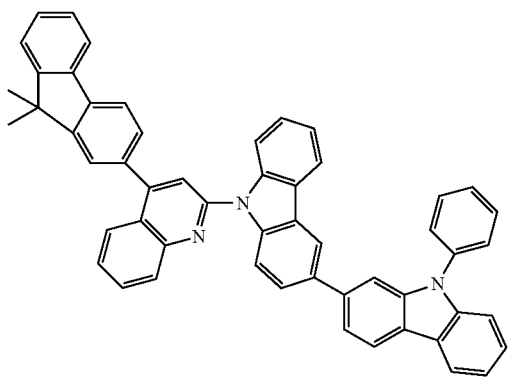
C-40
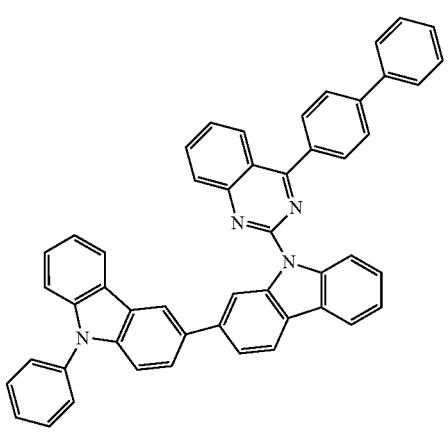
C-41
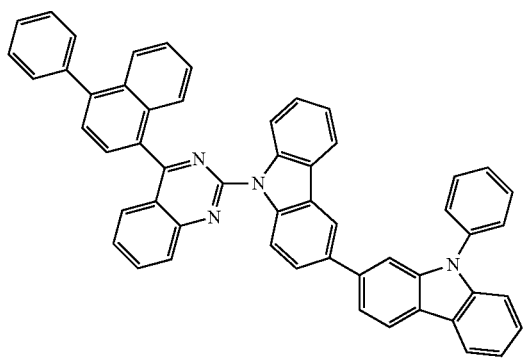
C-42
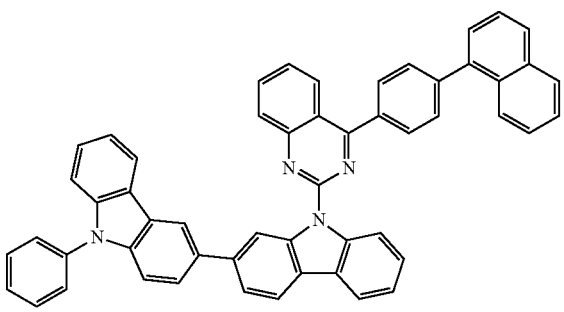
C-43
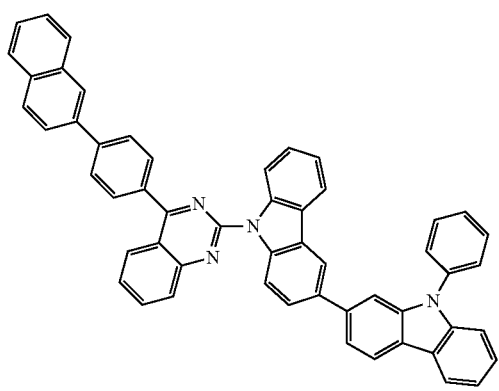
C-44
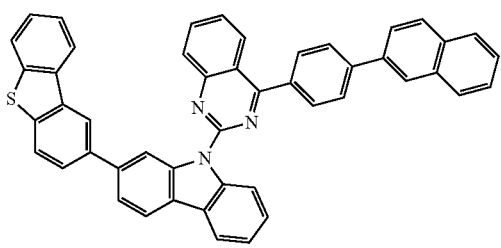

-continued
C-45
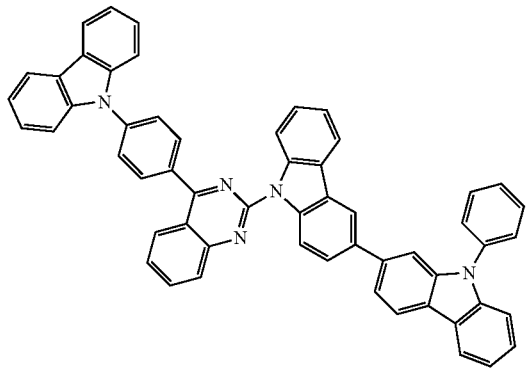
C-46
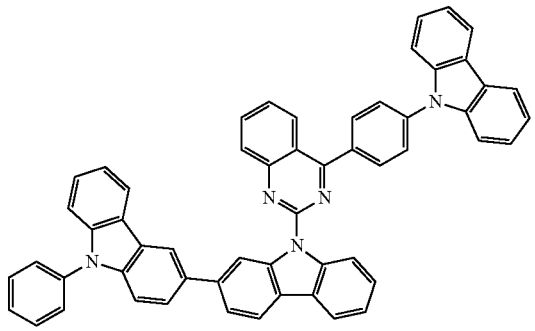
C-47
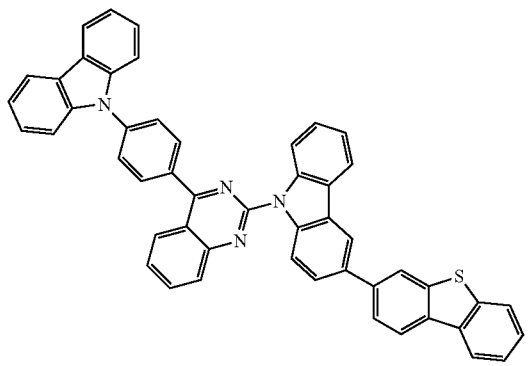
C-48
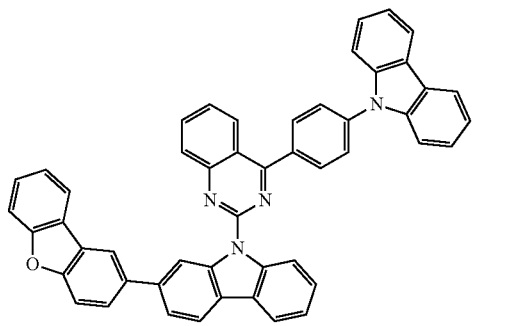
C-49
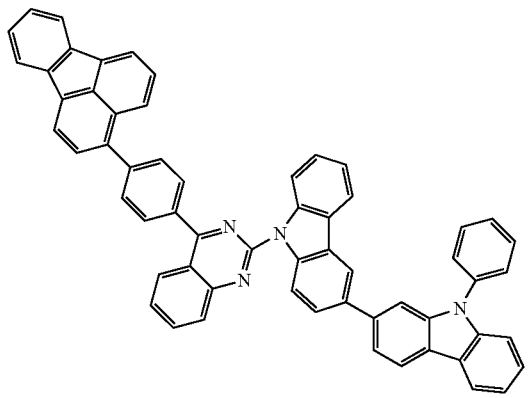
C-50
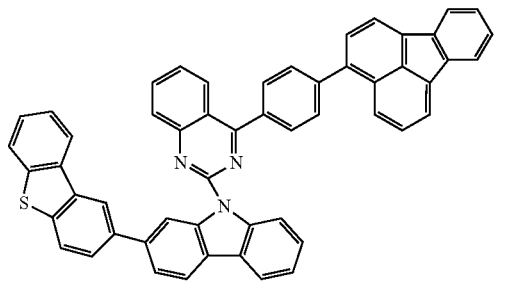
C-51
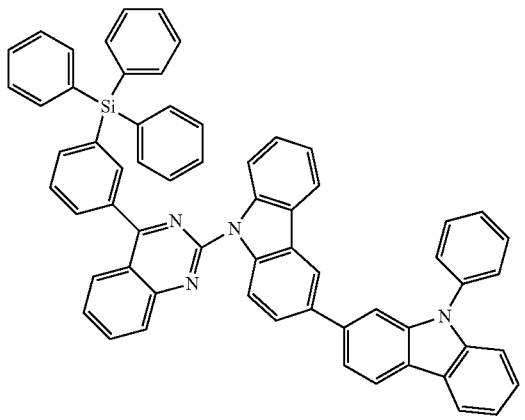
C-52
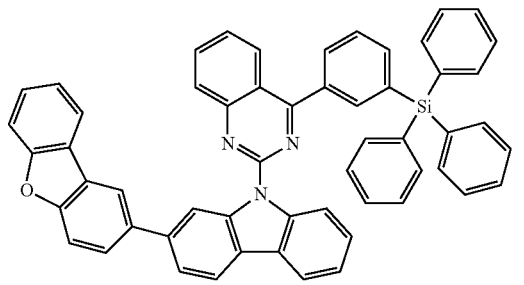

-continued
C-53
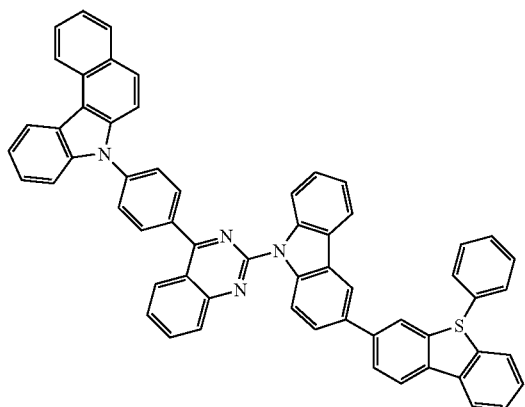
C-54
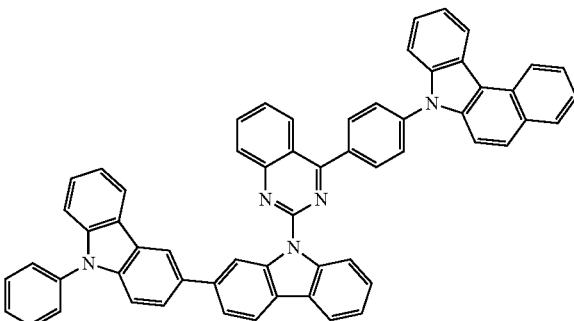
C-55
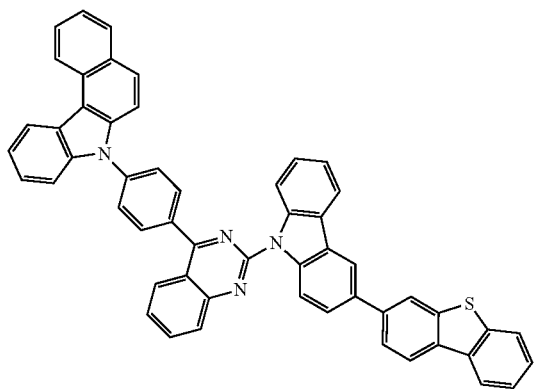
C-56
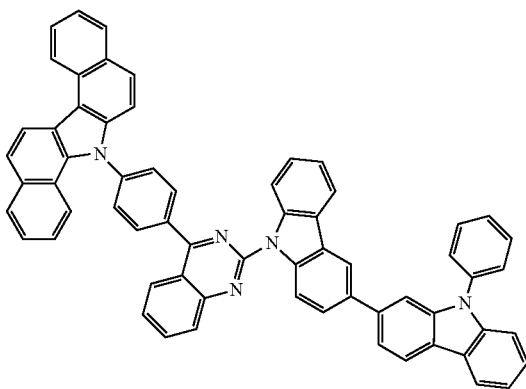
C-57
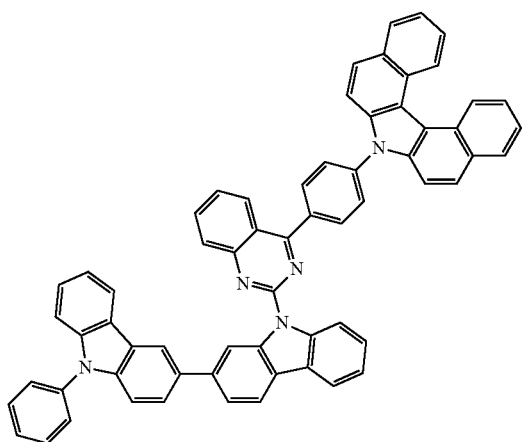
C-58
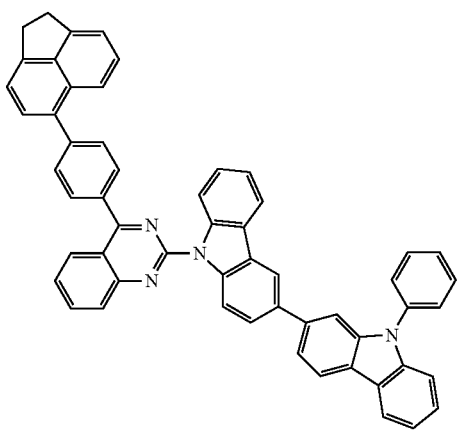

-continued
C-59
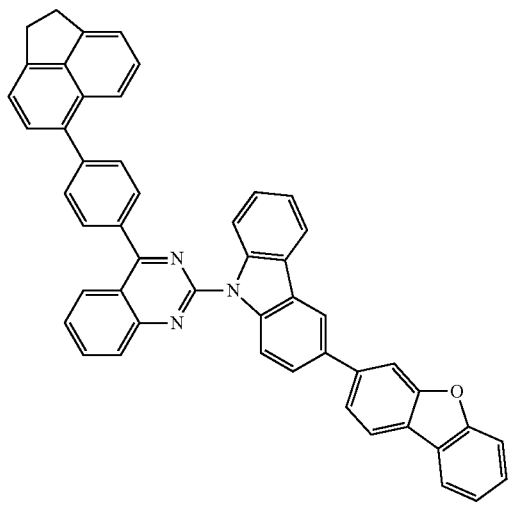
C-60
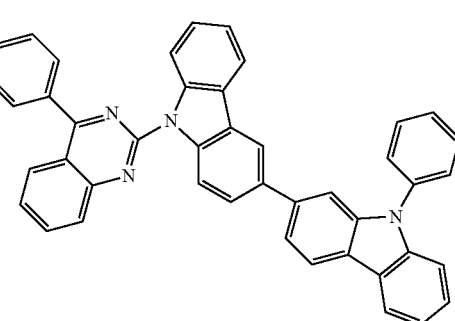
C-61
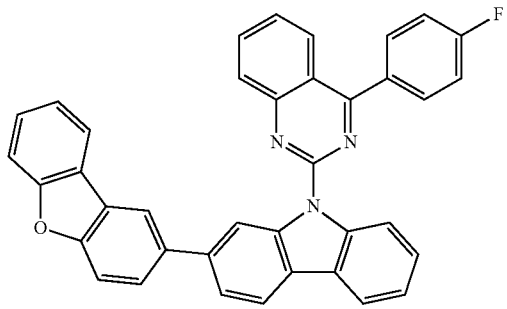
C-62
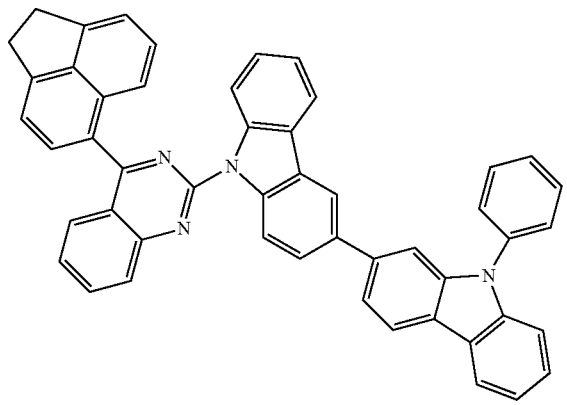
C-63
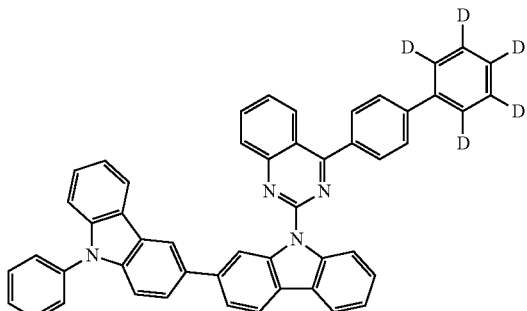
C-64
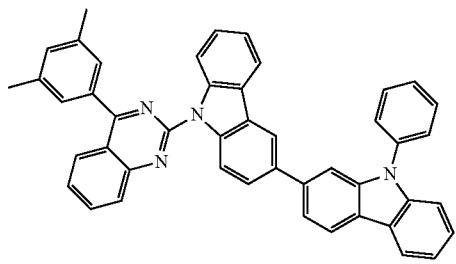
C-65
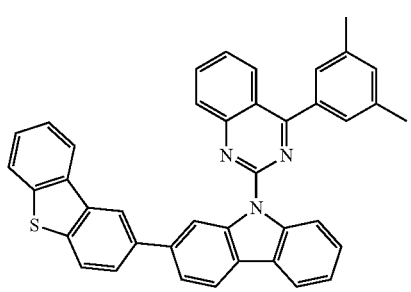
C-66
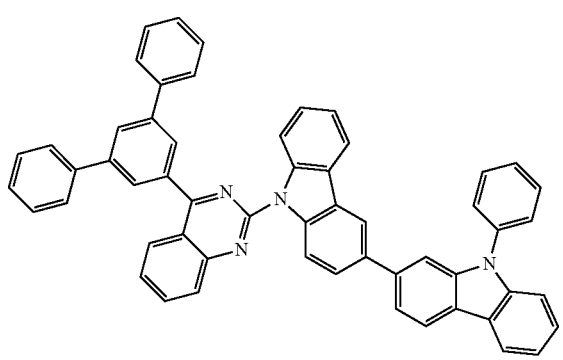

-continued
C-67
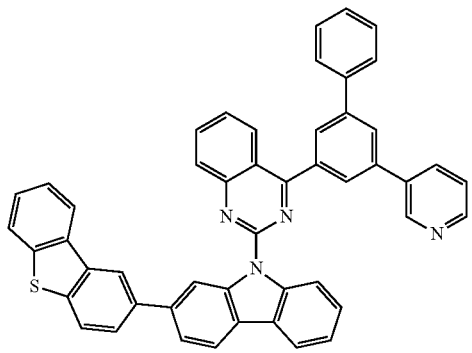
C-68
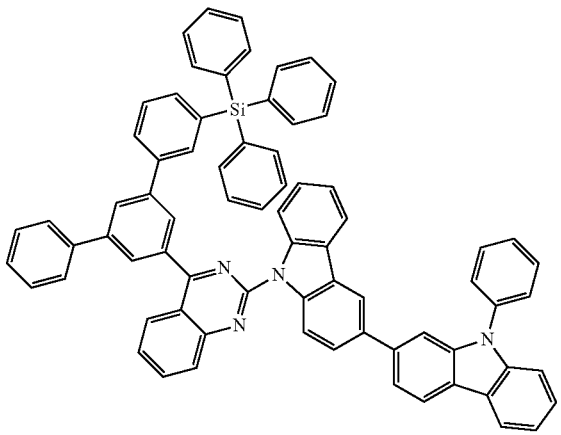
C-69
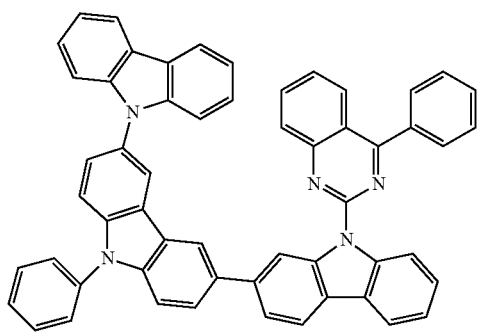
C-70
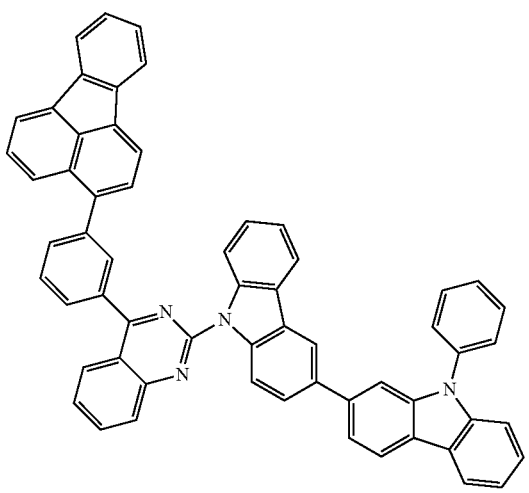
C-71
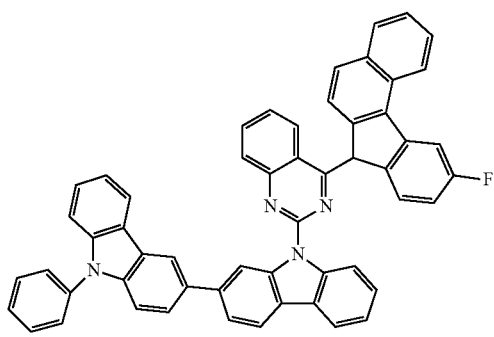
C-72
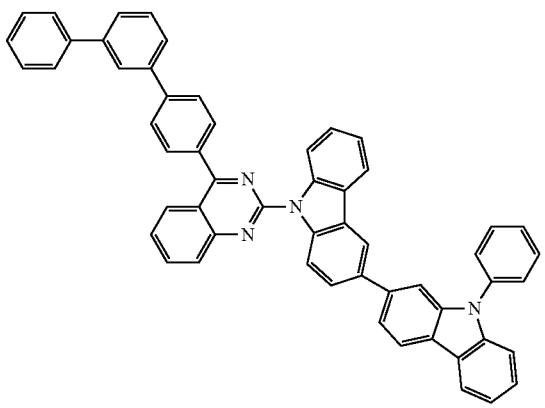

-continued
C-73
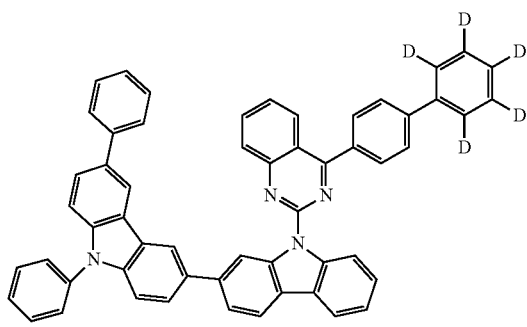
C-74
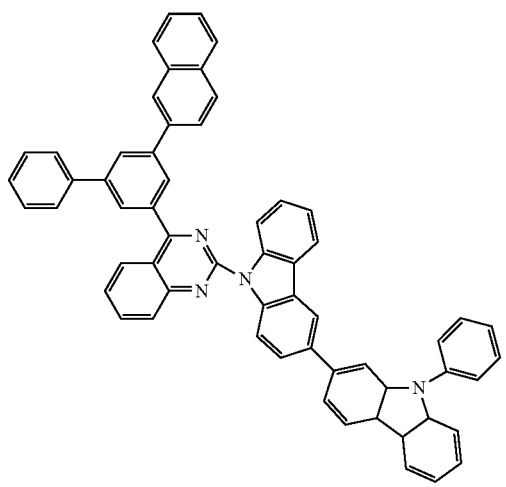
C-75
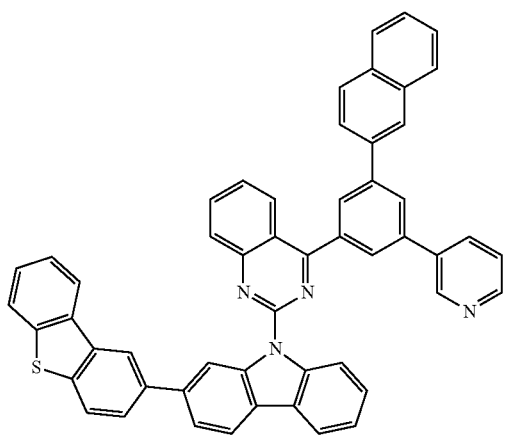
C-76
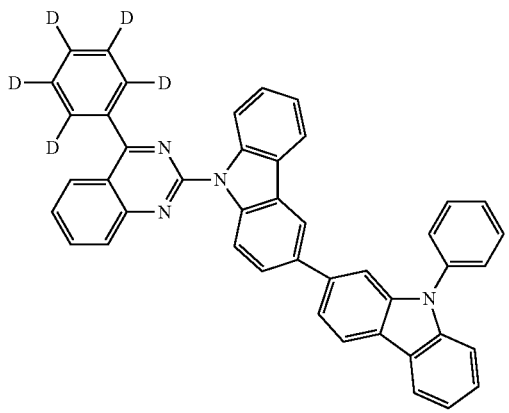
C-77
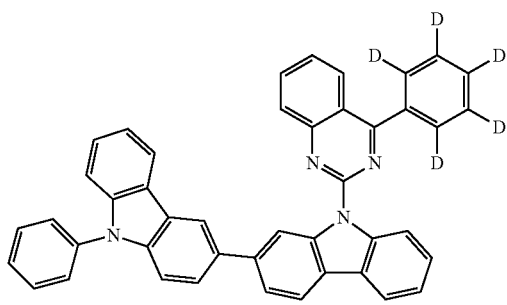
C-78
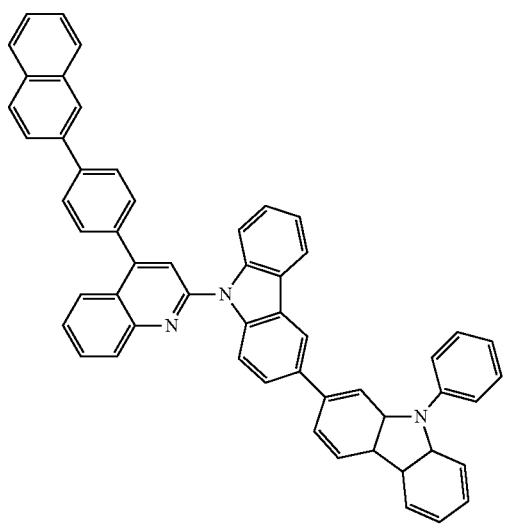

-continued
C-79
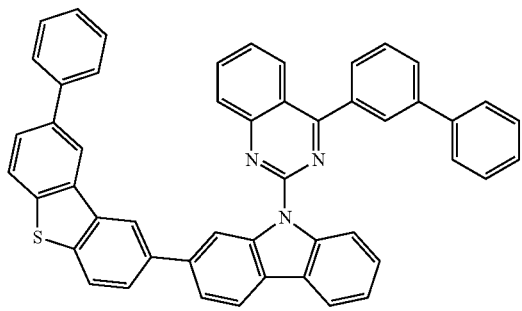
C-80
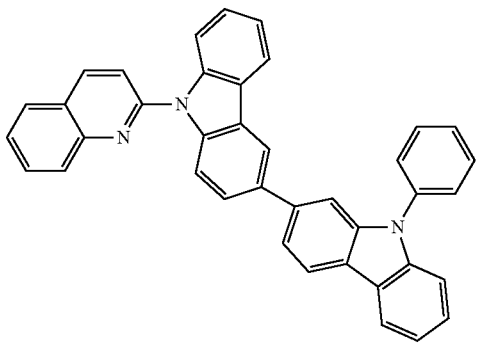
C-81
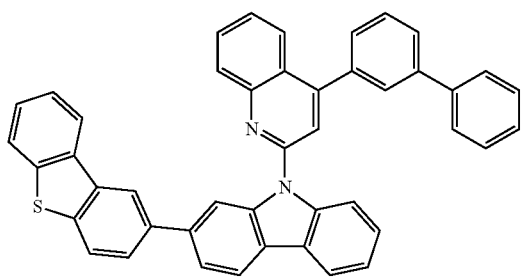
C-82
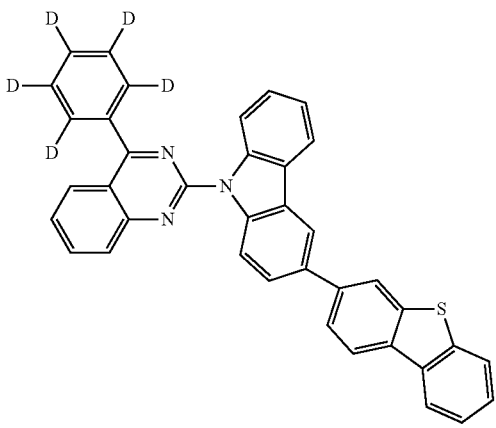
C-83
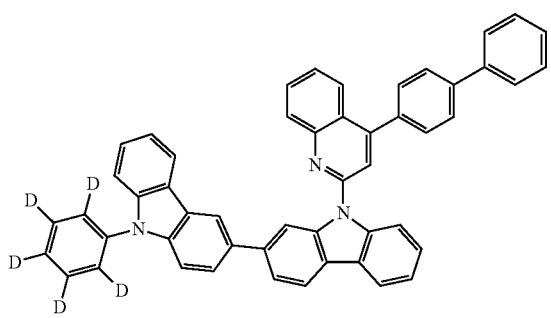
C-84
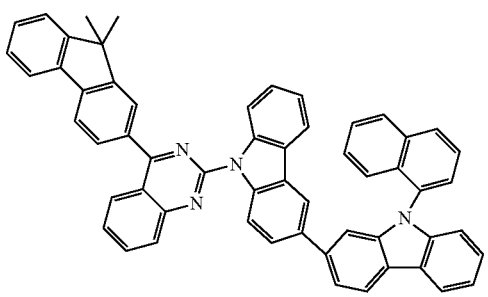
C-85
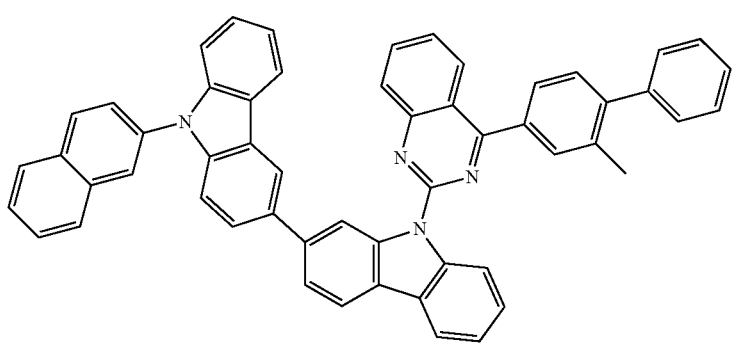

-continued
C-86
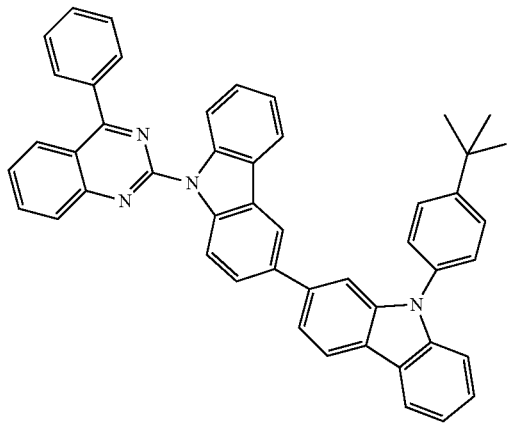
C-87
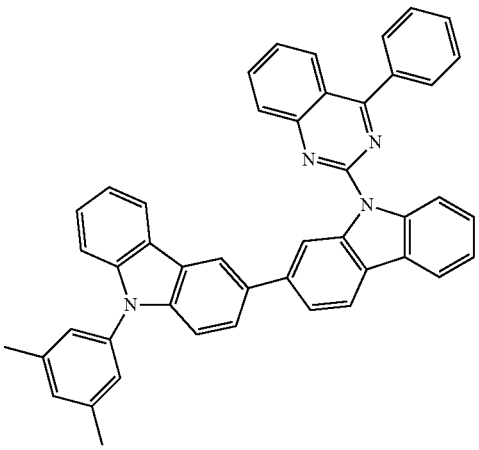
C-88
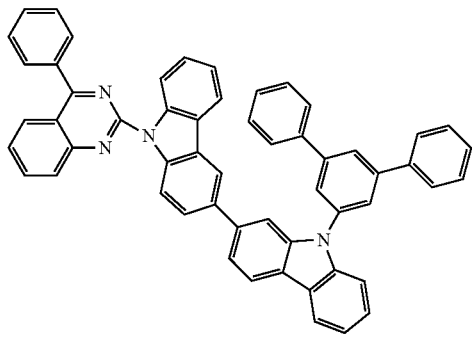
C-89
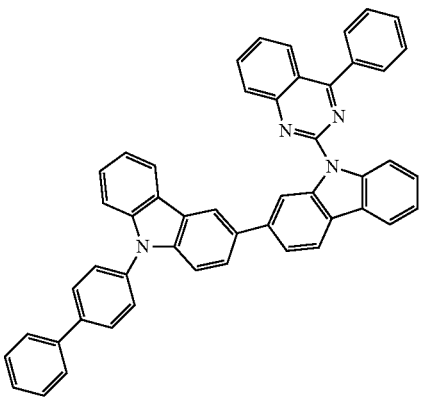
C-90
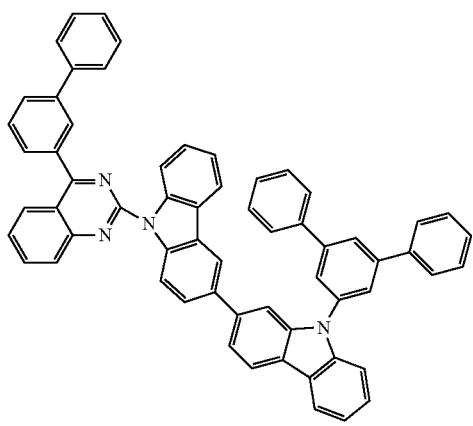
C-91
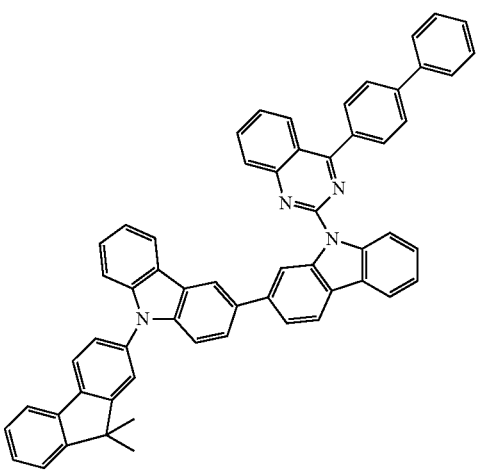

-continued
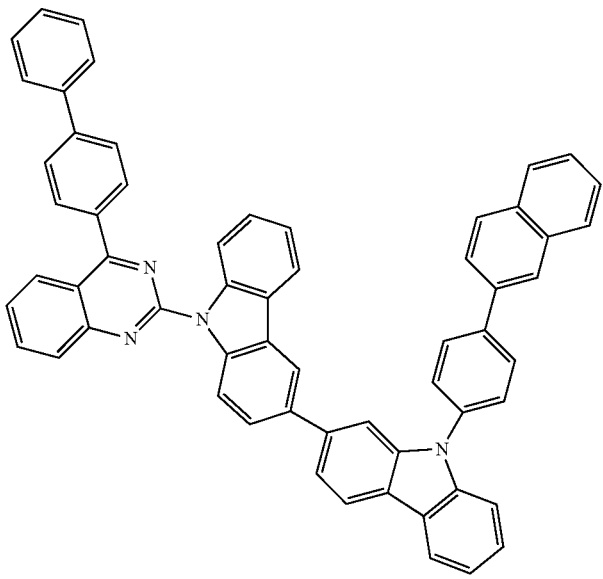
C-92
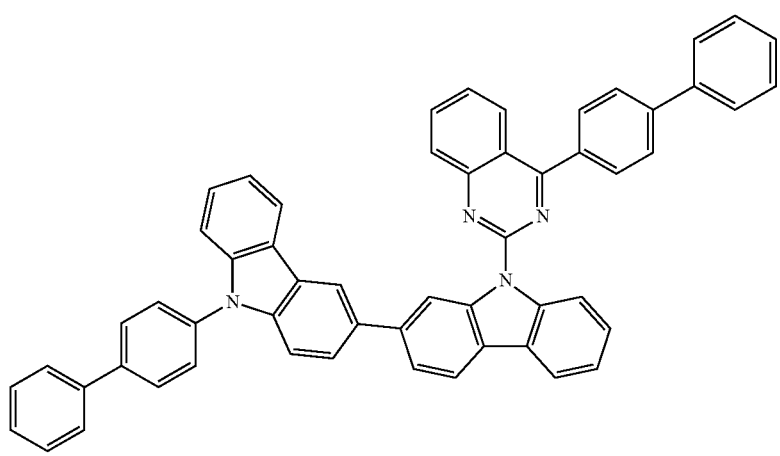
C-93
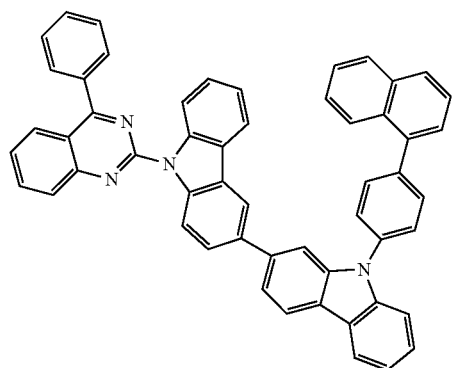
C-94
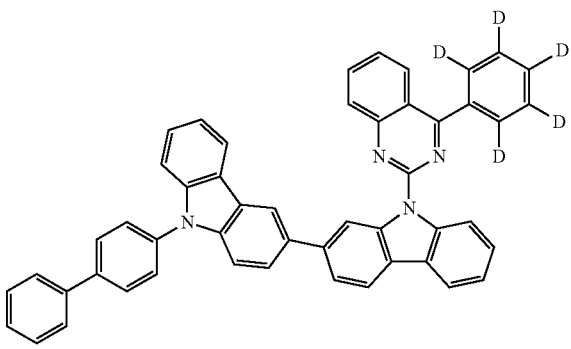
C-95

-continued
C-96
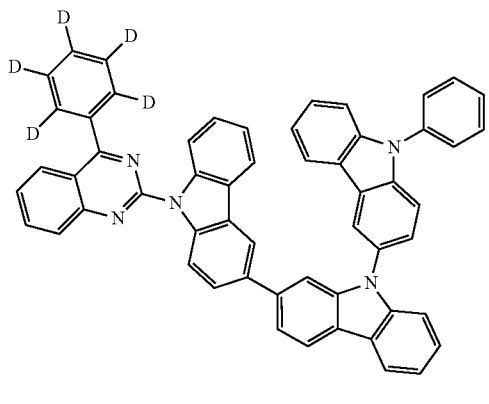
C-97
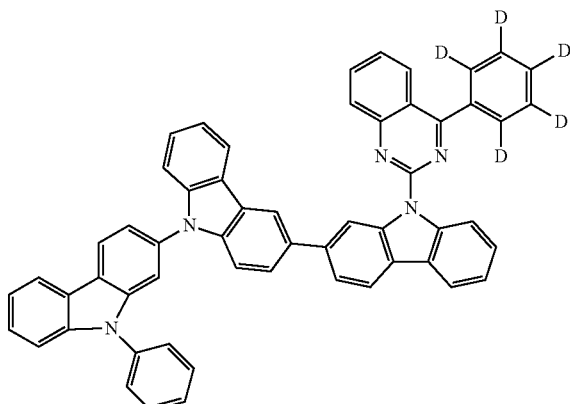
C-98
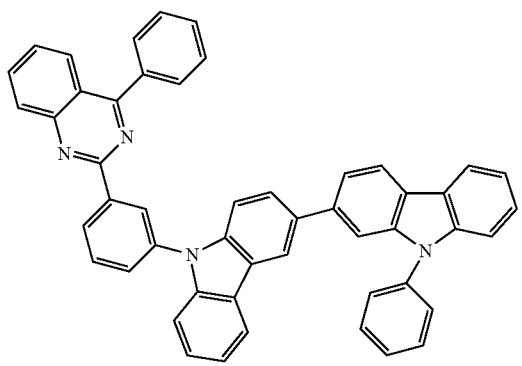
C-99
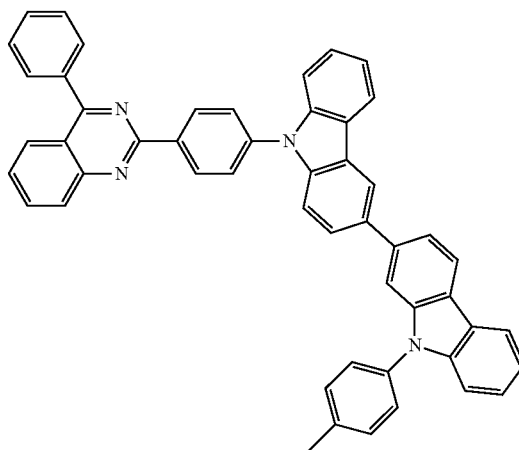
C-100
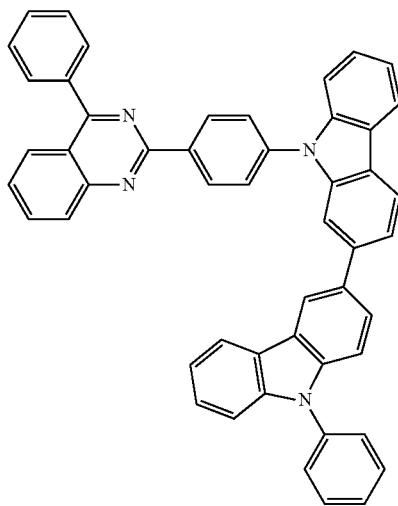
C-101
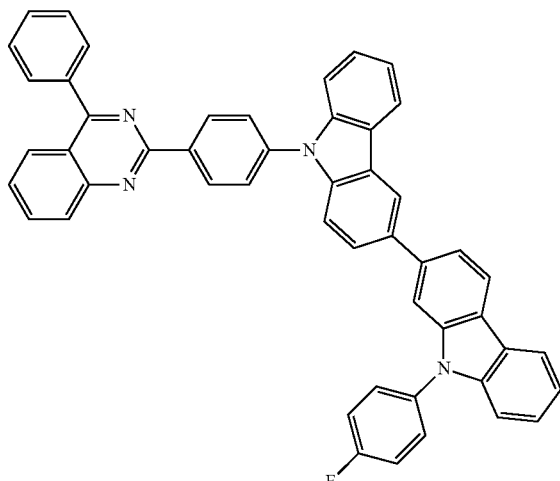

-continued
C-102
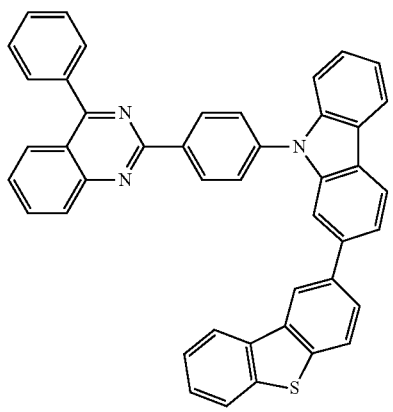
C-103
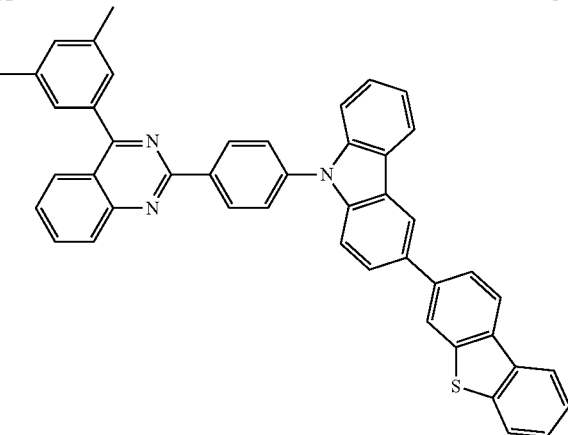
C-104
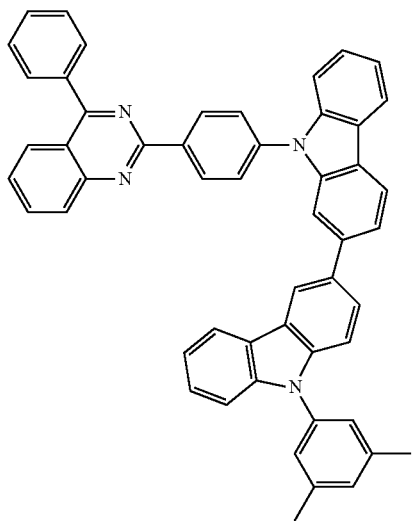
C-105
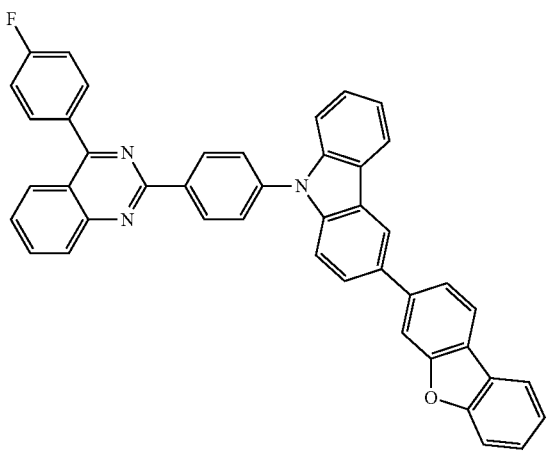
C-106
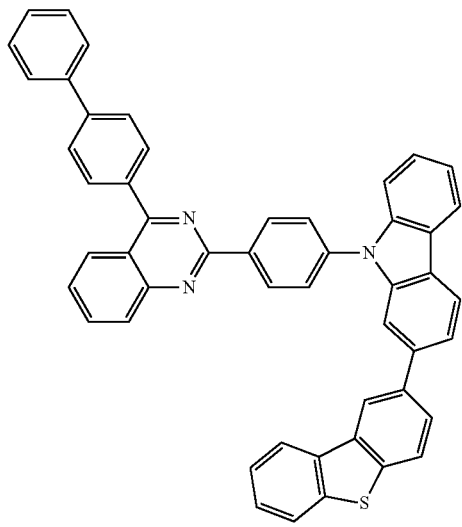
C-107
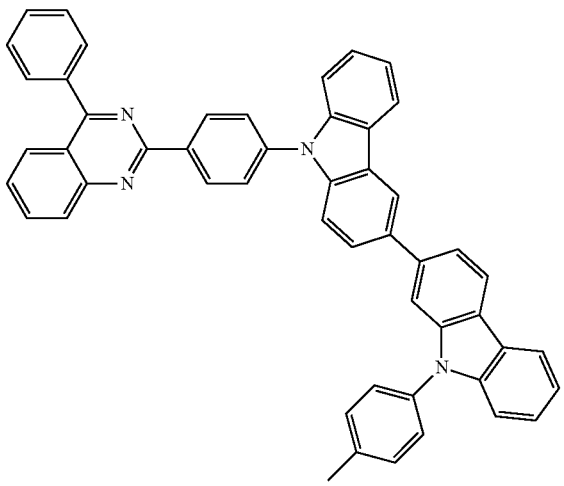

C-108
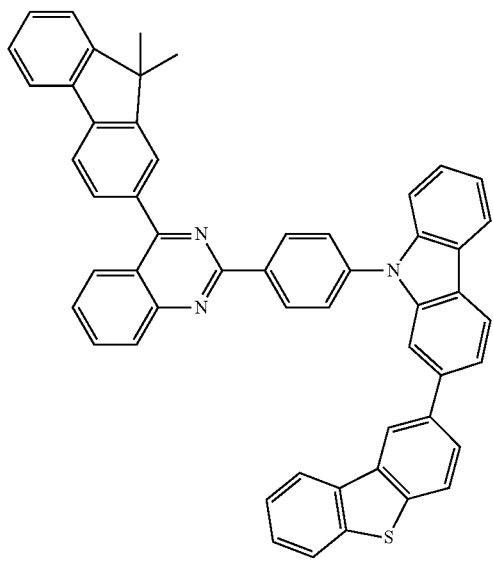
C-109
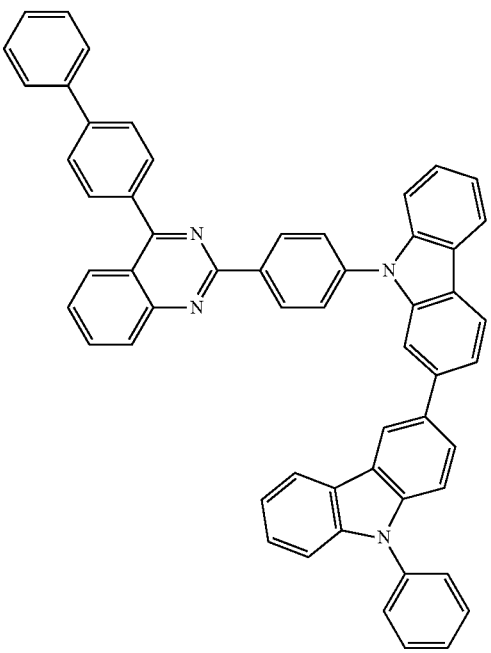
C-110
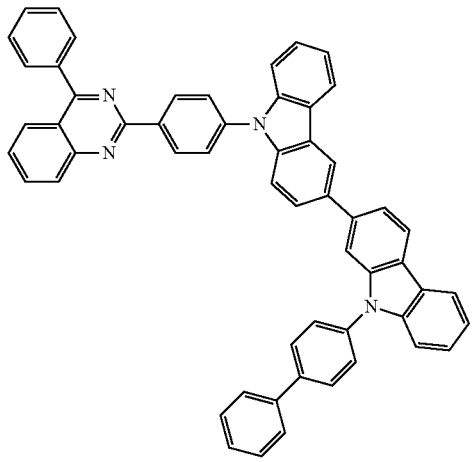
C-111
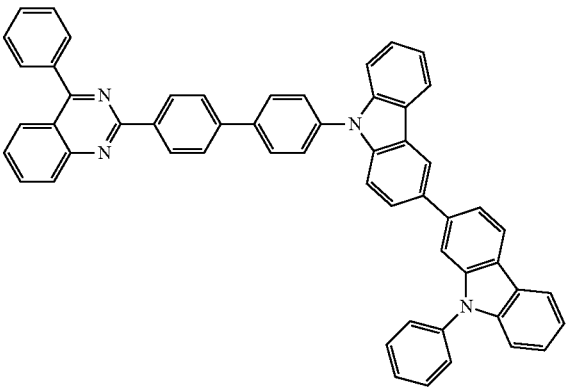
C-112
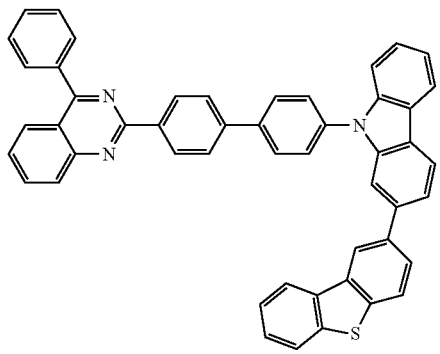
C-113
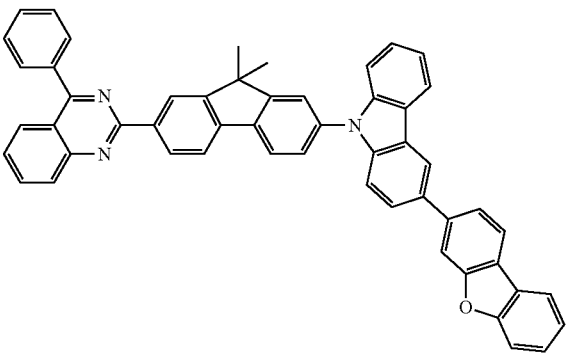

-continued
C-114
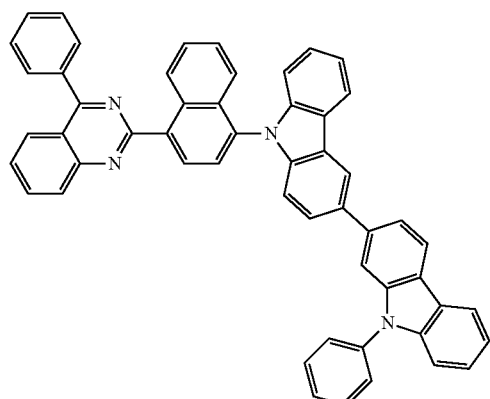
C-115
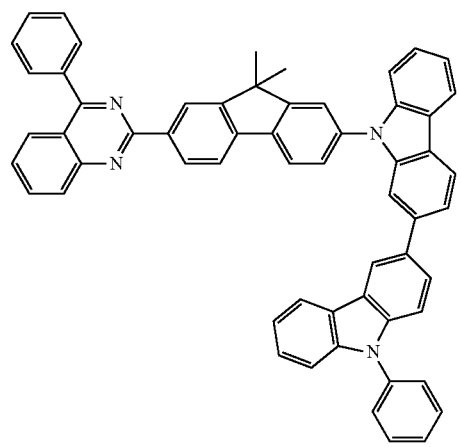
C-116
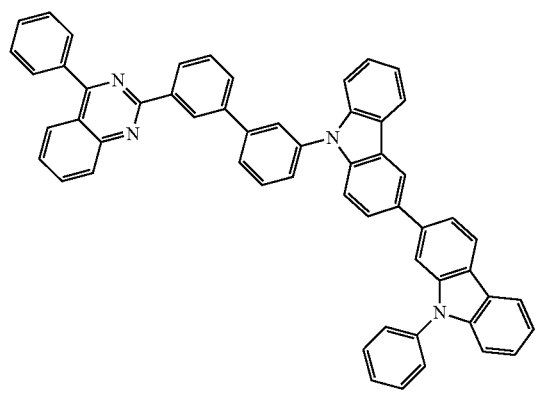
C-117
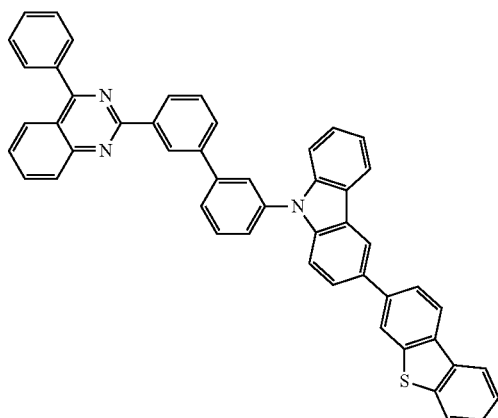
C-118
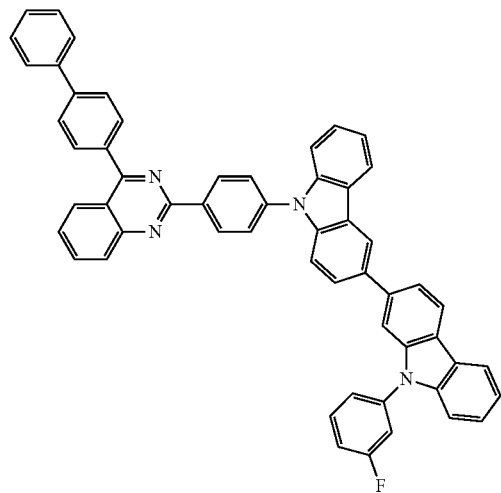
C-119
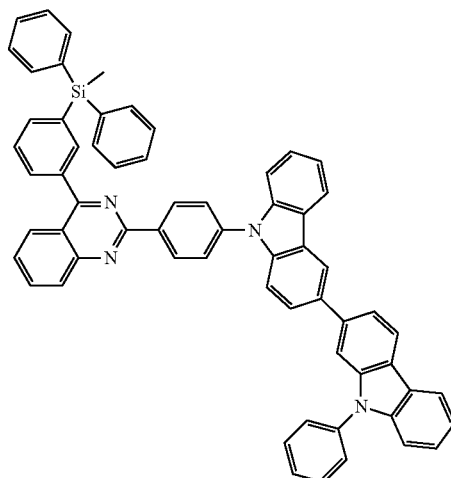

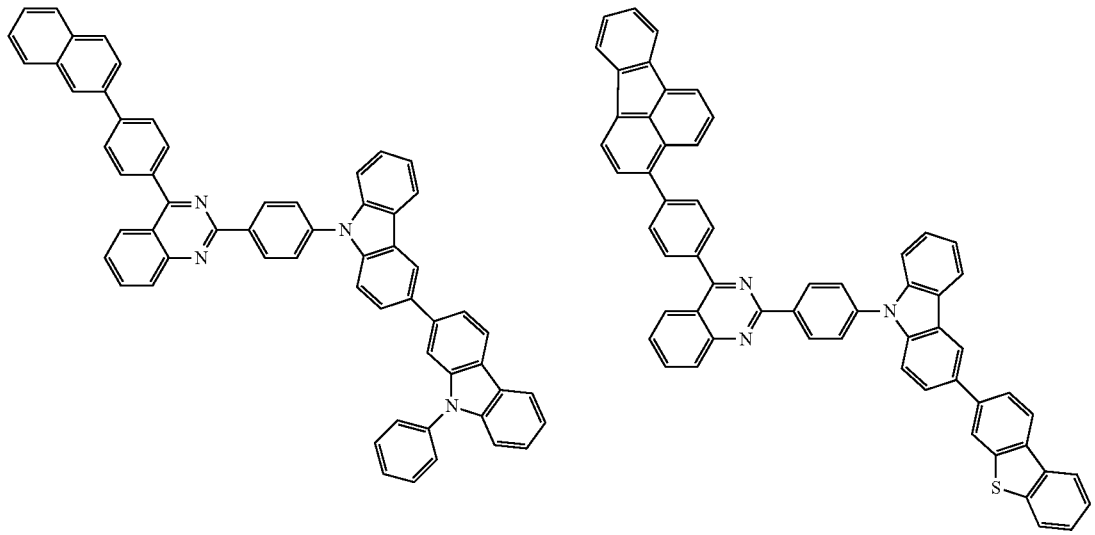
The compounds for organic electronic materials according to the present invention can be prepared by well-known methods in the art, for example, according to the following reaction schemes 1 or 2.
[Reaction Scheme 1]
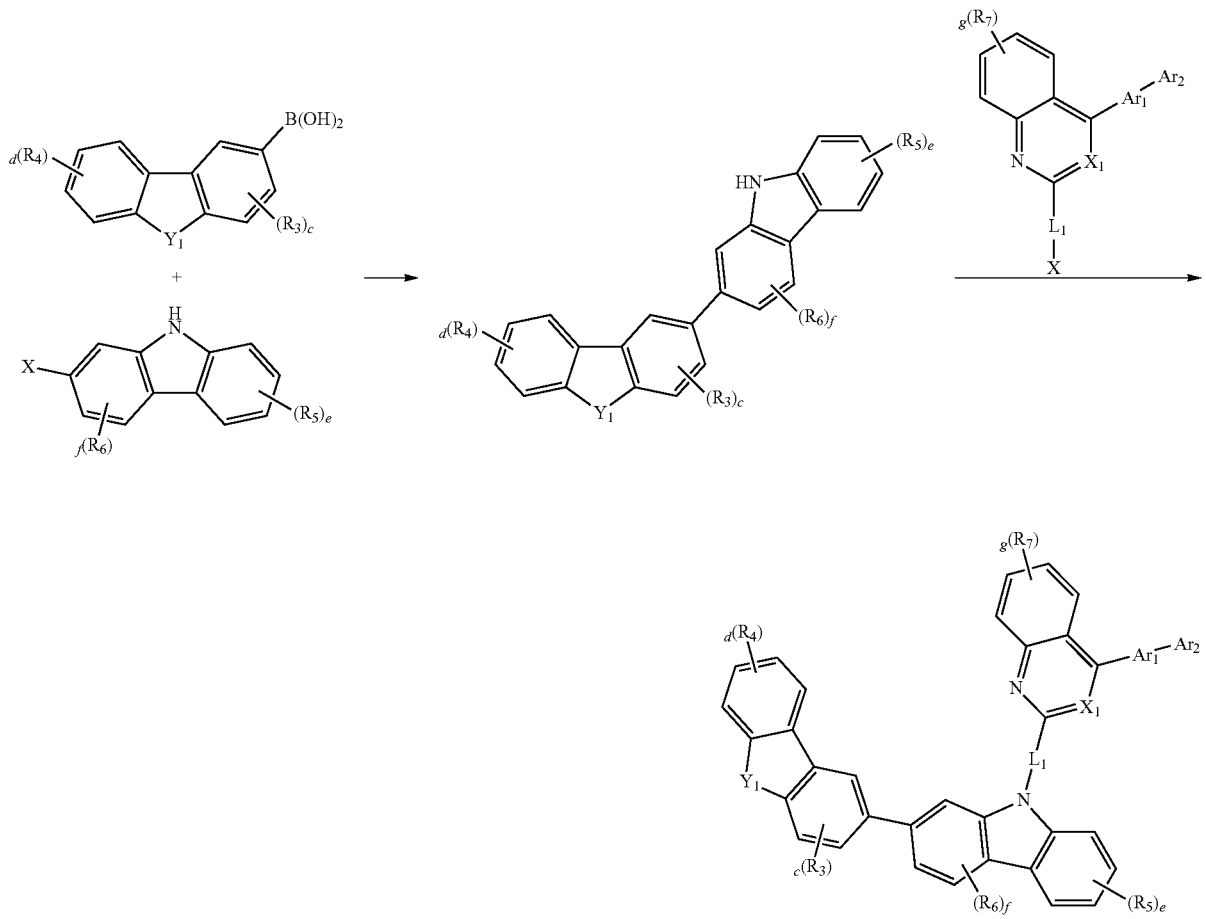

[Reaction Scheme 2]

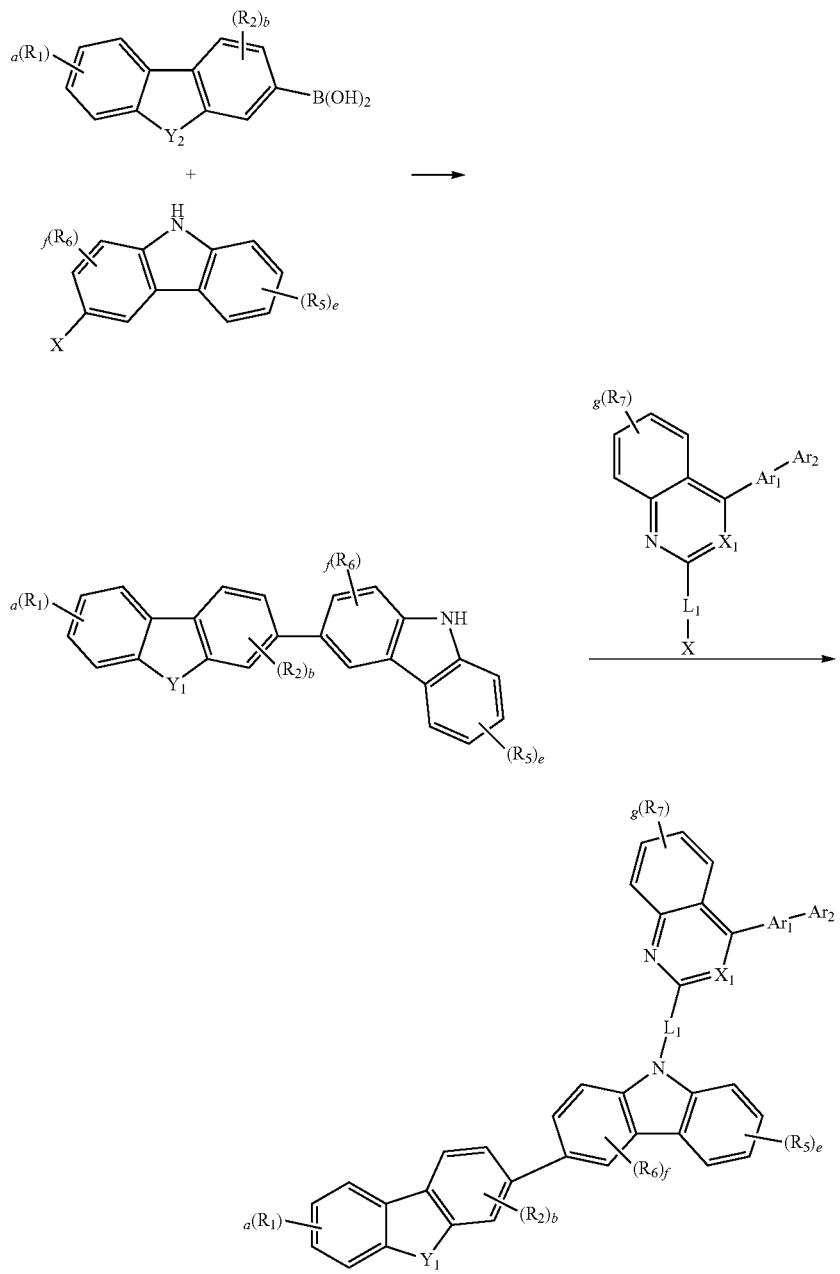

wherein $R_1$ to $R_7$, $Ar_1$, $Ar_2$, $Y_1$, $Y_2$, $X_1$, $L_1$, a, b, c, d, e, f and g are as defined in formula 1 above, and X represents a halogen.

Another embodiment of the present invention provides an organic electroluminescent device comprising the compound of formula 1. Said organic electroluminescent device comprises a first electrode, a second electrode, and at least one organic layer between said first and second electrodes. Said organic layer comprises at least one compound of formula 1 according to the present invention. Further, said organic layer comprises a light-emitting layer in which the compound of formula 1 is comprised as a host material.

Where the compound of formula 1 is comprised as a host material in the light-emitting layer, said light-emitting layer further comprises at least one phosphorescent dopant. In the organic electroluminescent device of the present invention, said phosphorescent dopant is not particularly limited, but may be selected from compounds represented by the following formula 2:

$$M^1 L^{101} L^{102} L^{103} \tag{2}$$

wherein $M^1$ is selected from the group consisting of Ir, Pt, Pd and Os; $L^{101}$, $L^{102}$ and $L^{103}$ are each independently selected from the following structures:

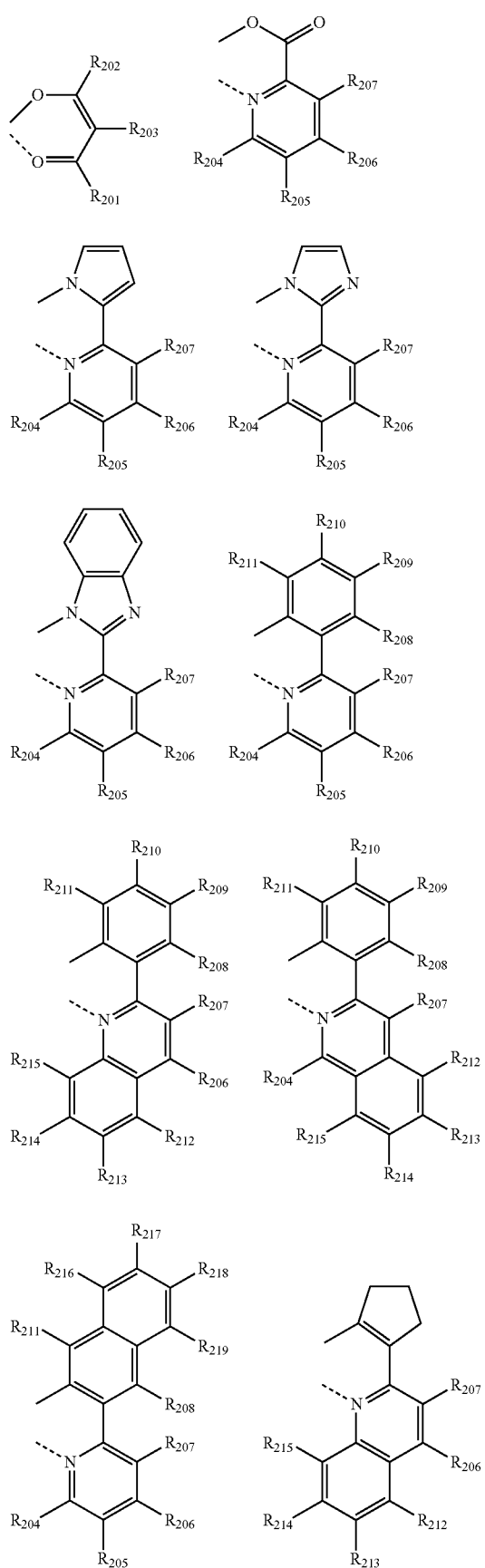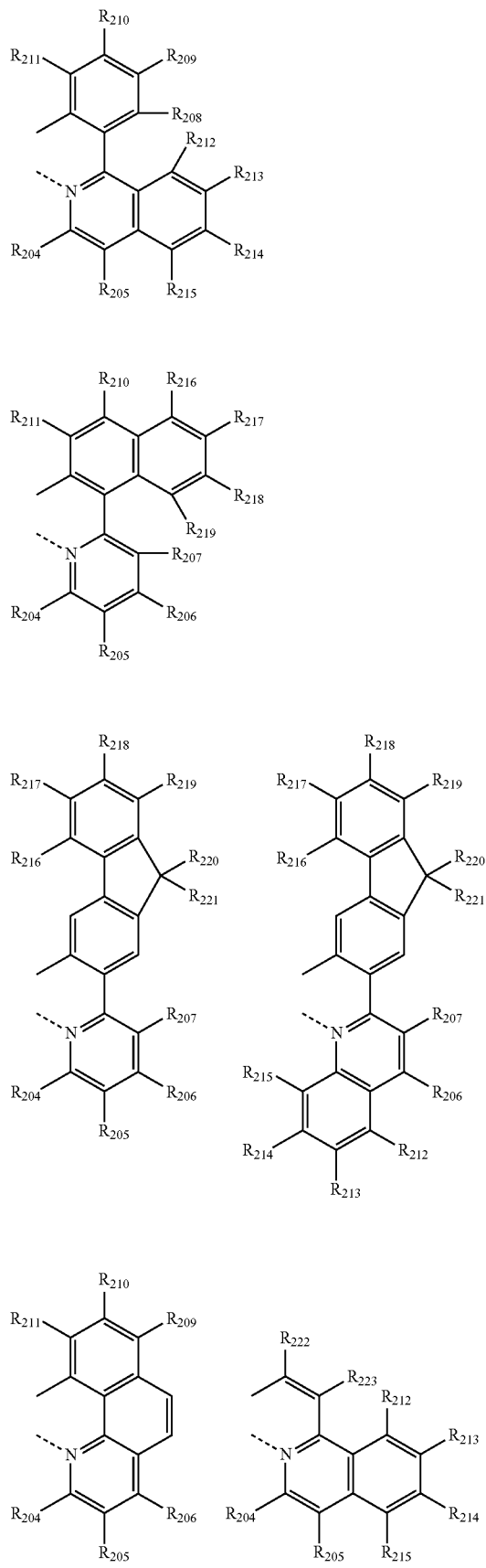

-continued

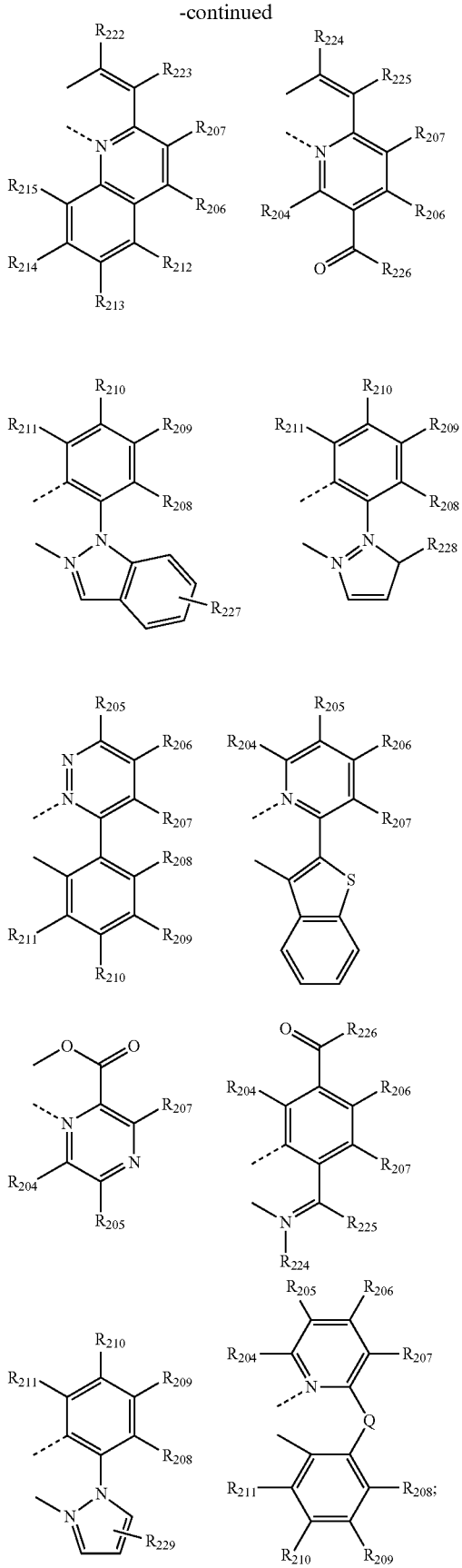

$R_{201}$ to $R_{203}$ each independently represent hydrogen, deuterium, a (C1-C30)alkyl group unsubstituted or substituted with halogen(s), a (C6-C30)aryl group unsubstituted or substituted with (C1-C30)alkyl group(s), or a halogen;

$R_{204}$ to $R_{219}$ each independently represent hydrogen, deuterium, a substituted or unsubstituted (C1-C30)alkyl group, a substituted or unsubstituted (C1-C30)alkoxy group, a substituted or unsubstituted (C3-C30)cycloalkyl group, a substituted or unsubstituted (C2-C30)alkenyl group, a substituted or unsubstituted (C6-C30)aryl group, a substituted or unsubstituted mono- or di-(C1-C30)alkylamino group, a substituted or unsubstituted mono- or di-(C6-C30)arylamino group, $SF_5$, a substituted or unsubstituted tri(C1-C30)alkylsilyl group, a substituted or unsubstituted di(C1-C30)alkyl (C6-C30)arylsilyl group, a substituted or unsubstituted tri (C6-C30)arylsilyl group, a cyano group or a halogen;

$R_{220}$ to $R_{223}$ each independently represent hydrogen, deuterium, a (C1-C30)alkyl group unsubstituted or substituted with halogen(s), or a (C6-C30)aryl group unsubstituted or substituted with (C1-C30)alkyl group(s);

$R_{224}$ and $R_{225}$ each independently represent hydrogen, deuterium, a substituted or unsubstituted (C1-C30)alkyl group, a substituted or unsubstituted (C6-C30)aryl group, or a halogen, or $R_{224}$ and $R_{225}$ may be linked to each other via a (C3-C12)alkylene group or (C3-C12)alkenylene group with or without a fused ring, to form a mono- or polycyclic, alicyclic or aromatic ring;

$R_{226}$ represents a substituted or unsubstituted (C1-C30) alkyl group, a substituted or unsubstituted (C6-C30)aryl group, a substituted or unsubstituted 5- or 30-membered heteroaryl group or a halogen;

$R_{227}$ to $R_{229}$ each independently represent hydrogen, deuterium, a substituted or unsubstituted (C1-C30)alkyl group, a substituted or unsubstituted (C6-C30)aryl group or a halogen;

Q represents

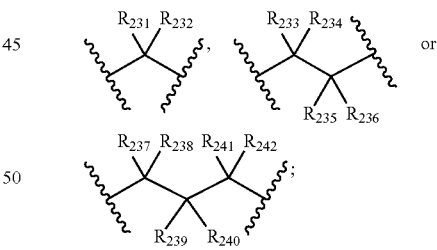

$R_{231}$ to $R_{242}$ each independently represent hydrogen, deuterium, a (C1-C30)alkyl group unsubstituted or substituted with halogen(s), a (C1-C30)alkoxy group, a halogen, a substituted or unsubstituted (C6-C30)aryl group, a cyano group, or a substituted or unsubstituted (C5-C30)cycloalkyl group, or each of $R_{231}$ to $R_{242}$ may be linked to an adjacent substituent via (C2-C30)alkylene group or (C2-C30)alkenylene group to form a Spiro ring or a fused ring or may be linked to $R_{207}$ or $R_{208}$ via a (C2-C30)alkylene group or (C2-C30)alkenylene group to form a saturated or unsaturated fused ring.

The dopants of formula 2 include the following, but are not limited thereto:

D-1
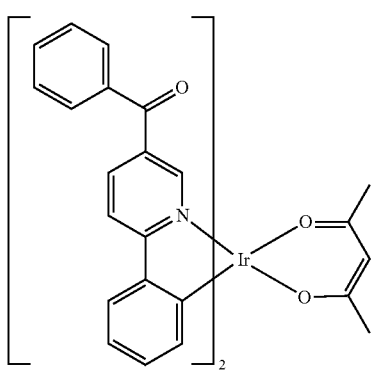
D-2
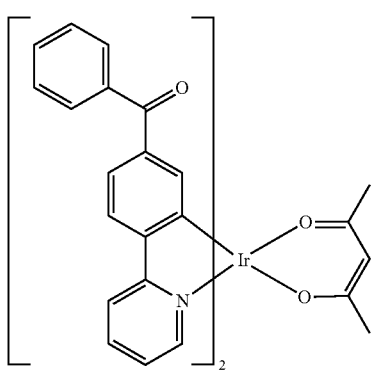
D-3
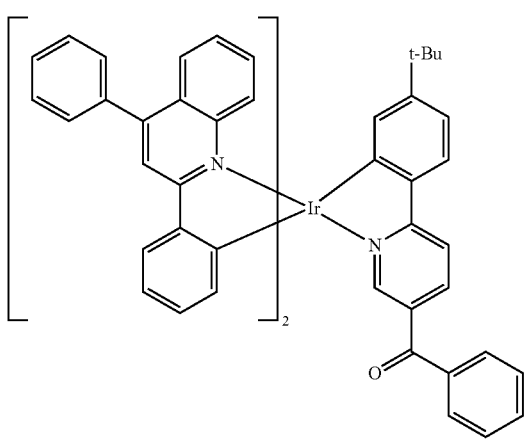
D-4
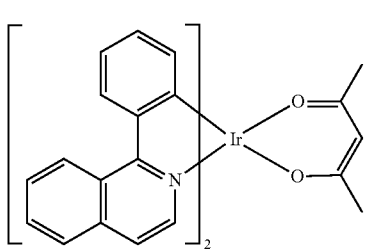
D-5
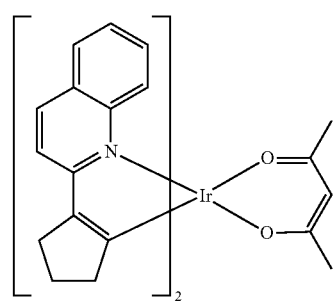
D-6
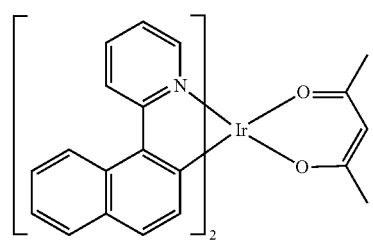
D-7
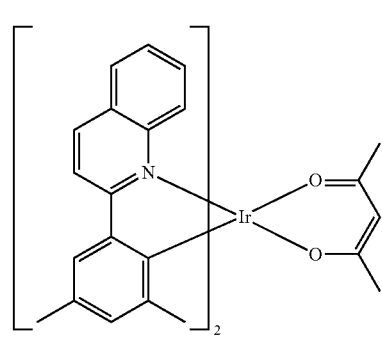
D-8
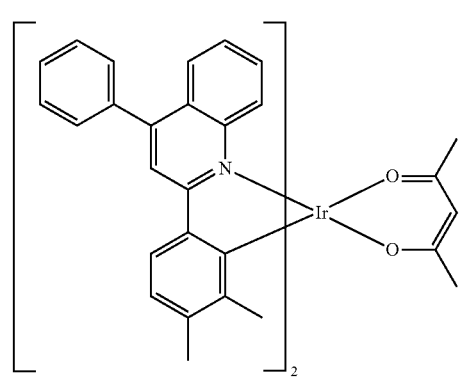
D-9
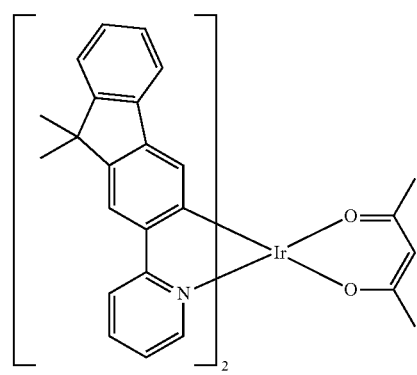

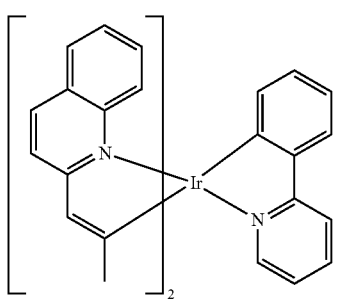
D-10
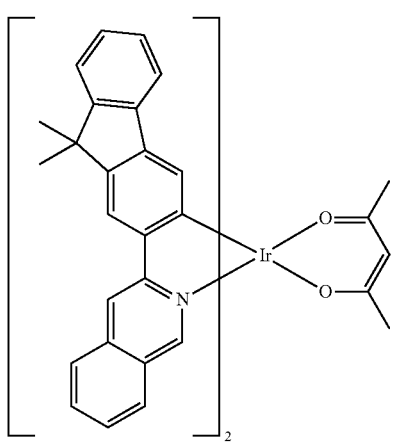
D-11
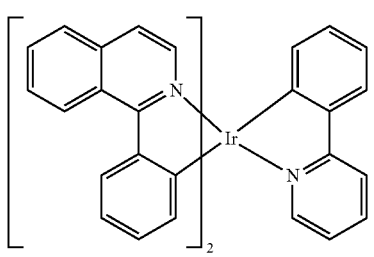
D-12
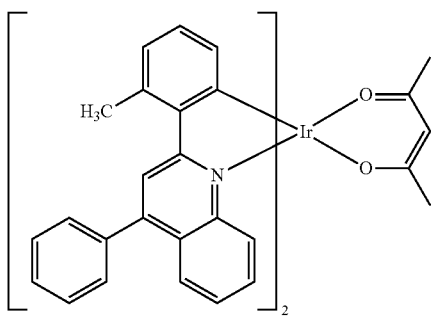
D-13
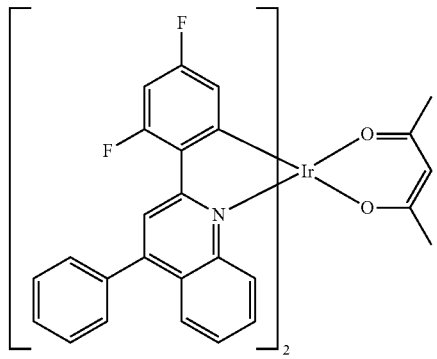
D-14
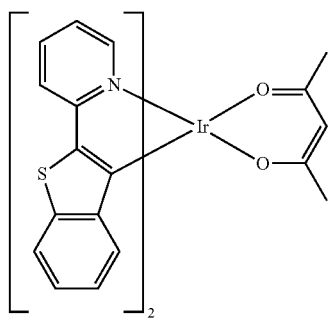
D-15
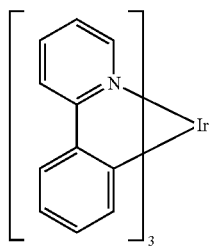
D-16
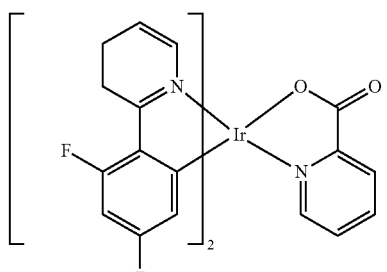
D-17
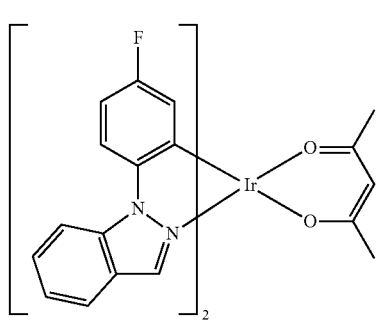
D-18

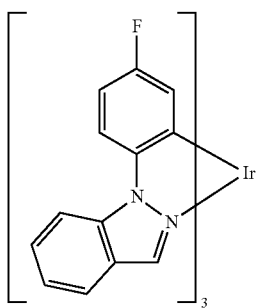
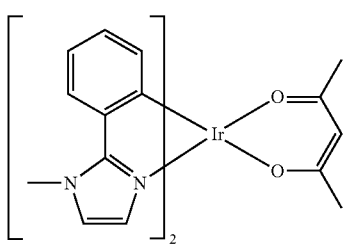
D-20
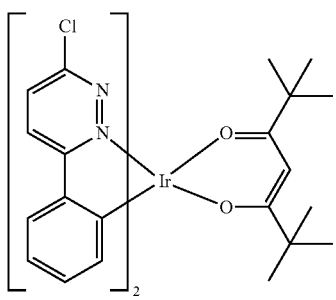
D-21
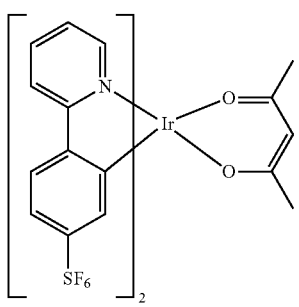
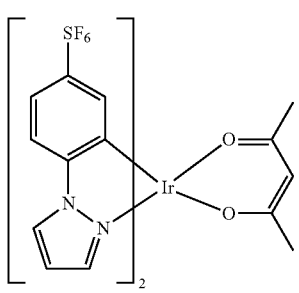
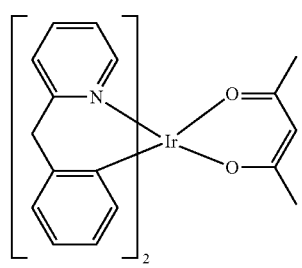
D-19
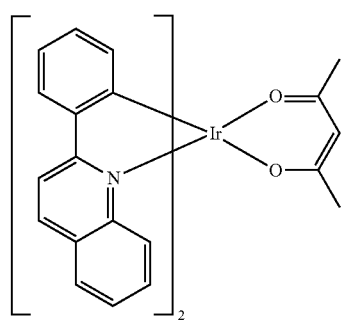
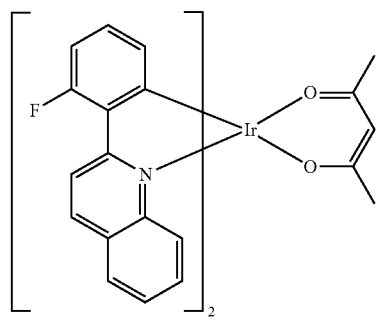
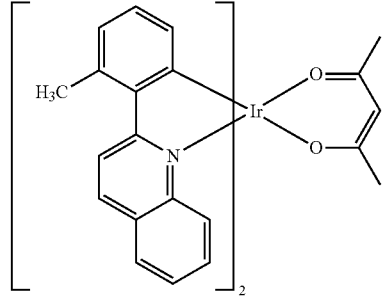
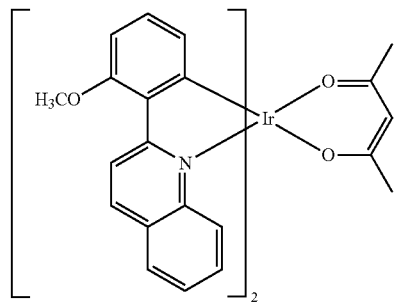
D-24
D-25
D-26
D-27
D-22
D-23
D-28

D-29 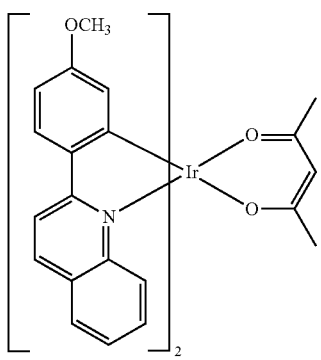

D-30 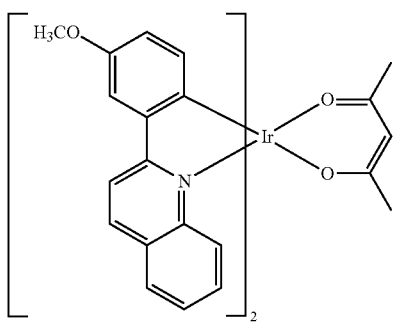

D-31 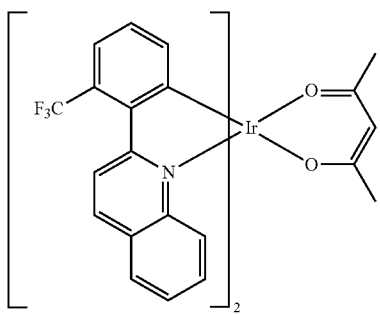

D-32 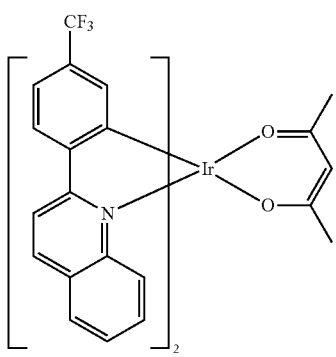

D-33 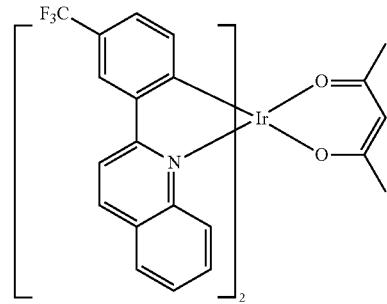

D-34 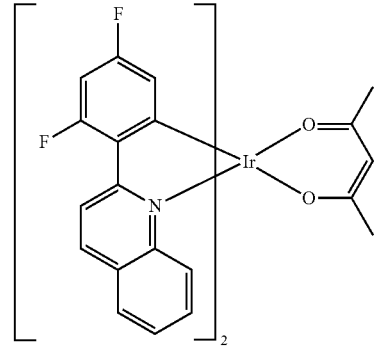

D-35 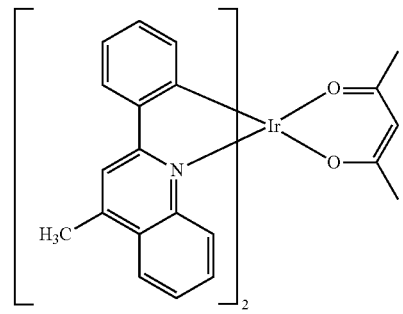

D-36 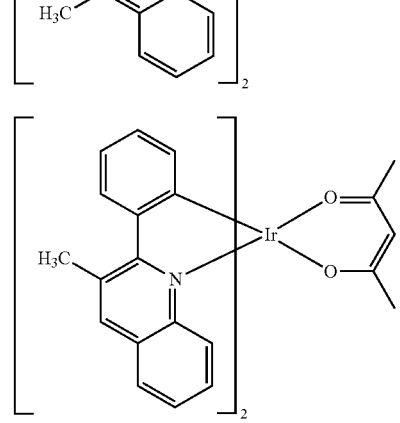

The organic electroluminescent device according to the present invention may further comprise, in addition to the organic electroluminescent compound according to the present invention, at least one compound selected from the group consisting of arylamine-based compounds and styrylarylamine-based compounds.

In the organic electroluminescent device according to the present invention, the organic layer may further comprise at least one metal selected from the group consisting of metals of Group 1, metals of Group 2, transition metals of the $4^{th}$ period, transition metals of the $5^{th}$ period, lanthanides and organic metals of d-transition elements of the Periodic Table, or at least one complex compound comprising said metal. The organic layer may comprise a light-emitting layer and a charge generating layer.

The organic electroluminescent device according to the present invention may emit a white light by further comprising at least one light-emitting layer which comprises a blue electroluminescent compound, a red electroluminescent compound or a green electroluminescent compound, in addition to said organic layer comprising the compound according to the present invention.

Preferably, in the organic electroluminescent device according to the present invention, at least one layer (hereinafter, "a surface layer") selected from a chalcogenide layer, a metal halide layer and a metal oxide layer may be placed on an inner surface(s) of one or both electrode(s). Specifically, it is preferred that a chalcogenide (includes oxides) layer of silicon or aluminum is placed on an anode surface of an electroluminescent medium layer, and a metal halide layer or metal oxide layer is placed on a cathode surface of an electroluminescent medium layer. Such a surface layer provides operation stability for the organic electroluminescent device. Preferably, said chalcogenide includes $SiO_x(1{\leq}X{\leq}2)$, $AlO_x$ $(1{\leq}X{\leq}1.5)$, SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

Preferably, in the organic electroluminescent device according to the present invention, a mixed region of an electron transport compound and an reductive dopant, or a mixed region of a hole transport compound and an oxidative dopant may be placed on at least one surface of a pair of electrodes. In this case, the electron transport compound is reduced to an anion, and thus it becomes easier to inject and transpor electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge generating layer to prepare an electroluminescent device having two or more electroluminescent layers and emitting a white light.

Hereinafter, the compound for organic electronic material, the preparation method of the compound, and the luminescent properties of the device comprising the compound of the present invention will be explained in detail with reference to the following examples:

Preparation Example 1

Preparation of Compound C-14

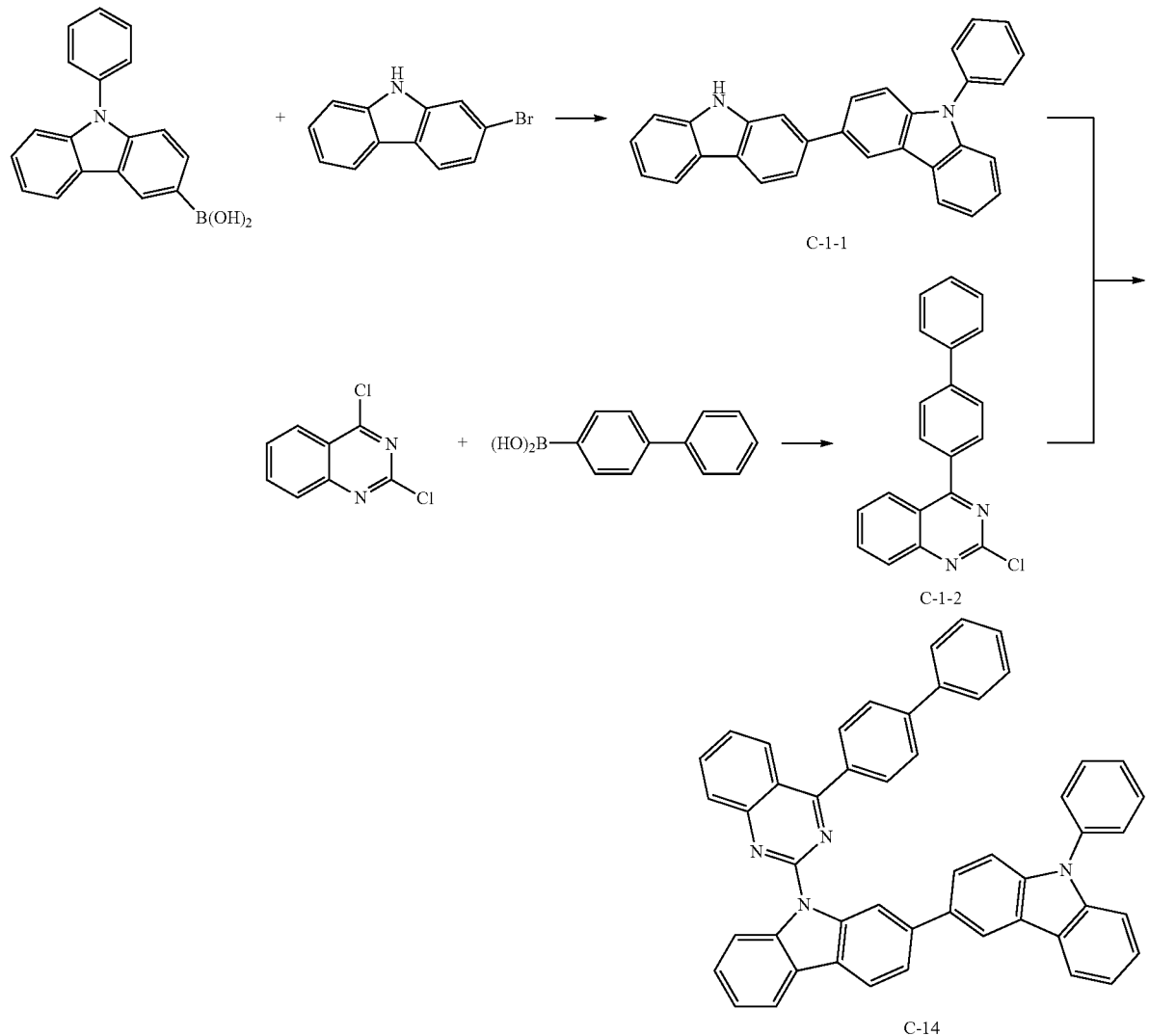

Preparation of Compound C-1-1

9-phenyl-9H-carbazol-3-yl boronic acid (10.1 g, 40.63 mmol), 2-bromo-9H-carbazole (14 g, 48.76 mmol), $K_2CO_3$ (13.5 g, 97.52 mmol) and $Pd(PPh_3)_4$ (2.35 g, 2.03 mmol) were added to a mixture of toluene 200 mL, EtOH 50 mL and purified water 50 mL. After stirring the reaction mixture for 3 hours at 95° C., the mixture was cooled to room temperature. An aqueous layer was removed from the mixture by a gravity separation. The obtained organic layer was concentrated, was triturated with methylene chloride (MC), and then was filtered to produce compound C-1-1 (11.9 g, 72%).

Preparation of Compound C-1-2

After dissolving 2,4-dichloroquinazoline (30 g, 151 mmol), biphenyl boronic acid (9.2 g, 75.3 mmol), $Pd(PPh_3)_4$ (2.6 g, 2.3 mmol) and $Na_2CO_3$ (16 g, 150 mmol) in a mixture of toluene (300 mL) and distilled water (75 mL), the reaction mixture was stirred for 2 hours at 90° C. The resulting organic layer was distillated under reduced pressure, and then was triturated with MeOH. The obtained solid was dissolved in MC, was filtered through silica, and then was triturated with MC and hexane to produce compound C-1-2 (9.3 g, 51.4%).

Preparation of Compound C-14

After suspending compound C-1-1 (5.3 g, 14.7 mmol) and compound C-1-2 (5 g, 15.8 mmol) in DMF 80 mL, 60% NaH (948 mg, 22 mmol) was added to the mixture at room temperature. The obtained reaction mixture was stirred for 12 hours. After adding purified water (1 L), the mixture was filtered under reduced pressure. The obtained solid was triturated with MeOH/ethyl acetate, was dissolved in MC, was filtered through silica, and then was triturated with MC/n-hexane to obtain compound C-14 (5 g, 51.5%).

MS/FAB found 689; calculated 688.82

Example 1

Production of an OLED Device Using the Compound According to the Present Invention A transparent electrode indium tin oxide (ITO) thin film (15 Ω/sq) on a glass substrate for an organic light-emitting diode (OLED) device (Samsung Corning, Republic of Korea) was subjected to an ultrasonic washing with trichloroethylene, acetone, ethanol and distilled water, sequentially, and then was stored in isopropanol. Then, the ITO substrate was mounted on a substrate holder of a vacuum vapor depositing apparatus. N1-(naphthalen-2-yl)-N4,N4-bis(4-(naphthalen-2-yl(phenyl)annino)phenyl)-N1-phenylbenzene-1,4-diamine was introduced into a cell of said vacuum vapor depositing apparatus, and then the pressure in the chamber of said apparatus was controlled to $10^{-6}$ torr. Thereafter, an electric current was applied to the cell to evaporate the above introduced material, thereby forming a hole injection layer having a thickness of 60 nm on the ITO substrate. Then, N,N'-di(4-biphenyl)-N,N'-di(4-biphenyl)-4,4'-diaminobiphenyl was introduced into another cell of said vacuum vapor depositing apparatus, and was evaporated by applying electric current to the cell, thereby forming a hole transport layer having a thickness of 20 nm on the hole injection layer. Thereafter, compound C-14 was introduced into one cell of the vacuum vapor depositing apparatus, as a host material, and compound D-7 was introduced into another cell as a dopant. The two materials were evaporated at different rates and were deposited in a doping amount of 4 to 20 wt % to form a light-emitting layer having a thickness of 30 nm on the hole transport layer. Then, 9,10-di(1-naphthyl)-2-(4-phenyl-1-phenyl-1H-benzo[d]imidazole)anthracene was introduced into one cell and lithium quinolate was introduced into another cell. The two materials were evaporated at different rates and were deposited in a doping amount of 30 to 70 wt % to form an electron transport layer having a thickness of 30 nm on the light-emitting layer. Then, after depositing lithium quinolate as an electron injection layer having a thickness of 1 to 2 nm on the electron transport layer, an Al cathode having a thickness of 150 nm was deposited by another vacuum vapor deposition apparatus on the electron injection layer. Thus, an OLED device was produced. All the material used for producing the OLED device were those purified by vacuum sublimation at $10^{-6}$ torr.

The produced OLED device showed red emission having a luminance of 1,020 cd/m² and a current density of 8.2 mA/cm² at a driving voltage of 4.2V. Further, the minimum time taken to be reduced to 90% of the luminance at a luminance of 5,000 nit was 130 hours.

Comparative Example 1

Production of an OLED Device Using Conventional Electroluminescent Compounds An OLED device was produced in the same manner as that of Example 1, except that a light-emitting layer having a thickness of 30 nm was deposited on the hole transport layer by using 4,4'-N,N'-dicarbazol-biphenyl (CBP) as a host material and $(piq)_2Ir(acac)$ [bis-(1-phenylisoquinolyl)iridium(III) acetylacetonate] as a dopant and that a hole blocking layer having a thickness of 10 nm was deposited by using aluminum(III) bis(2-methyl-8-quinolinato)-4-phenylphenolate.

The produced OLED device showed red emission having a luminance of 1,000 cd/m² and a current density of 12.5 mA/cm² at a driving voltage of 5.5V. Further, the minimum time taken to be reduced to 90% of the luminance at a luminance of 5,000 nit was 15 hours.

The compounds of the present invention have superior luminescent properties than the conventional materials. Further, the device using the compounds according to the present invention as a host material has a low driving voltage and can improve power consumption. Therefore, the present invention can manufacture a device that has high luminous efficiency and a long operation lifetime.

The invention claimed is:
1. A compound represented by the following formula 1:

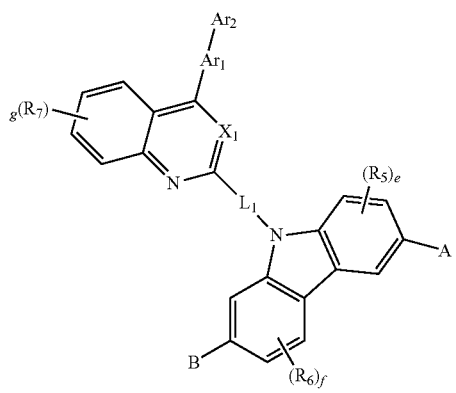

(1)

wherein
A represents hydrogen or

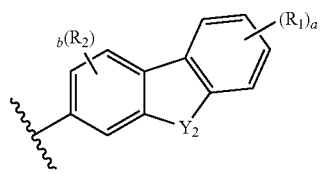

B represents hydrogen or

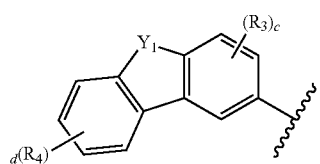

with the proviso that A and B are not hydrogen simultaneously;
$L_1$ represents a single bond, a substituted or unsubstituted 5- to 30-membered heteroarylene group, a substituted or unsubstituted (C6-C30)arylene group, or a substituted or unsubstituted (C6-C30)cycloalkylene group;
$X_1$ represents N;
$Y_1$ and $Y_2$ each independently represent —O—, —S—, —$CR_8R_9$— or —$NR_{10}$—;
$Ar_1$ represents a single bond, a substituted or unsubstituted 5- to 30-membered heteroarylene group, a substituted or unsubstituted (C6-C30)arylene group, or a substituted or unsubstituted (C1-C30)alkylene group;
$Ar_2$ represents hydrogen, deuterium, a substituted or unsubstituted (C1-C30)alkyl group, a substituted or unsubstituted (C6-C30)aryl group, or a substituted or unsubstituted 3- to 30-membered heteroaryl group;
$R_1$ to $R_{10}$ each independently represent hydrogen, deuterium, a halogen, a substituted or unsubstituted (C1-C30)alkyl group, a substituted or unsubstituted (C6-C30)aryl group, a substituted or unsubstituted 3- to 30-membered heteroaryl group, a substituted or unsubstituted (C3-C30)cycloalkyl group, a substituted or unsubstituted 5- to 7-membered heterocycloalkyl group, a substituted or unsubstituted (C6-C30)aryl(C1-C30)alkyl group, a substituted or unsubstituted (C6-C30)aryl group fused with at least one (C3-C30)cycloalkyl group, a 5- to 7-membered heterocycloalkyl group fused with at least one substituted or unsubstituted (C6-C30)aromatic ring, a (C3-C30)cycloalkyl group fused with at least one substituted or unsubstituted (C6-C30)aromatic ring, —$NR_{11}R_{12}$, —$SiR_{13}R_{14}R_{15}$, —$SR_{16}$, —$OR_{17}$, a substituted or unsubstituted (C2-C30)alkenyl group, a substituted or unsubstituted (C2-C30)alkynyl group, a cyano group, a nitro group, or a hydroxyl group; or are linked to an adjacent substituent via a substituted or unsubstituted (C3-C30)alkylene or a (C3-C30)alkenylene group to form a mono- or polycyclic, alicyclic or aromatic ring whose carbon atom(s) may be replaced with at least one heteroatom selected from nitrogen, oxygen and sulfur;
$R_{11}$ to $R_{17}$ have the same definition as one of $R_1$ to $R_{10}$;
a, d and g each independently represent an integer of 1 to 4, where a, d or g is an integer of 2 or more, and each of $R_1$, each of $R_4$ or each of $R_7$ is the same or different;
b, c, e and f each independently represent an integer of 1 to 3, where b, c, e or f is an integer of 2 or more, and each of $R_2$, each of $R_3$, each of $R_5$ or each of $R_6$ is the same or different; and
the heterocycloalkyl group and the heteroaryl(ene) group contain at least one heteroatom selected from B, N, O, S, P(=O), Si and P.

2. The compound according to claim 1, characterized in that substituents of the substituted (C1-C30)alkyl group, the substituted (C2-C30)alkenyl group, the substituted (C2-C30)alkynyl group, the substituted (C6-C30)cycloalkylene group, the substituted (C3-C30)cycloalkyl group, the substituted 5- to 7-membered heterocycloalkyl group, the substituted (C6-C30)aryl(ene) group, the substituted 5- to 30-membered heteroaryl(ene) group and the substituted aromatic ring in said $L_1$, $Ar_1$, $Ar_2$, $R_1$ to $R_{10}$ and $R_{11}$ to $R_{17}$ groups each independently are at least one selected from the group consisting of deuterium, a halogen, a (C1-C30)alkyl substituted or unsubstituted with a halogen, a (C6-C30)aryl, a 3- to 30-membered heteroaryl substituted or unsubstituted with a (C6-C30)aryl, a 5- to 7-membered heterocycloalkyl group, a 5- to 7-membered heterocycloalkyl group fused with at least one (C6-C12)aromatic ring, a (C3-C30)cycloalkyl group, a (C6-C30) cycloalkyl group fused with at least one (C6-C12)aromatic ring, $R_aR_bR_cSi$—, a (C2-C30)alkenyl group, a (C2-C30)alkynyl group, a cyano group, a carbazolyl group, —$NR_dR_e$, —$BR_fR_g$, —$PR_hR_i$, —P(=O)$R_jR_k$, a (C6-C30)aryl(C1-C30)alkyl group, a (C1-C30)alkyl(C6-C30)aryl group, $R_1Z$—$R_mC$(=O)—, $R_mC$(=O)O—, a carboxyl group, a nitro group and a hydroxyl group,
wherein $R_a$ to $R_1$ each independently represent a (C1-C30)alkyl group, a (C6-C30)aryl group or a 3- to 30-membered heteroaryl group, or are linked to an adjacent substituent via a substituted or unsubstituted (C3-C30)alkylene or a (C3-C30)alkenylene group to form a mono- or polycyclic, alicyclic or aromatic ring whose carbon atom(s) may be replaced with at least one heteroatom selected from nitrogen, oxygen and sulfur; Z represents S or O; and $R_m$ represents a (C1-C30)alkyl group, a (C1-C30)alkoxy group, a (C6-C30)aryl group or a (C6-C30)aryloxy group.

3. The compound according to claim 1, characterized in that X1 represents N; and L1 is selected from the group consisting of a single bond, phenylene, naphthylene, biphenylene, terphenylene, anthrylene, andenylene, fluorenylene, phenanthrylene, triphenylenylene, pyrenylene, phenylenylene, chrysenylene, naphthasenylene, fluorantenyl, furylene, thiophenylene, pyrrolylene, imidazolylene, pyrazolylene, thiazolylene, thiadiazolylene, isothiazolylene, isoxazolylene, oxazolylene, oxadiazolylene, triazinylene, tetrazinylene, triazolylene, tetrazolylene, furazanylene, pyridylene, pyrazinylene, pyrimidinylene, pyridazinylene, benzofuranylene, benzothiophenylene, isobenzofuranylene, benzoimidazolylene, benzothiazolylene, benzoisothiazolylene, benzoisoxazolylene, benzooxazolylene, isoindolylene, indolylene, indazolylene, benzothiadiazolylene, quinolylene, isoquinolylene, cinnolinylene, quinazolinylene, quinoxalinylene, carbazolylene, phenanthridinylene, benzodioxolylene, dibenzofuranylene and dibenzothiophenylene.

4. The compound according to claim 1, characterized in that

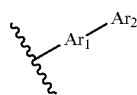

is selected from the following structures:

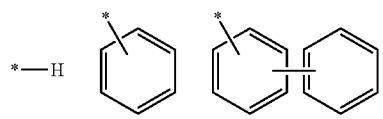

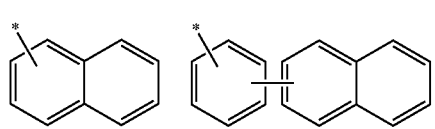

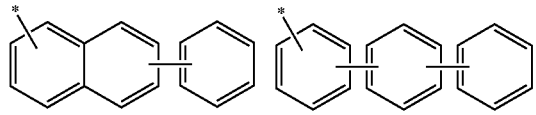

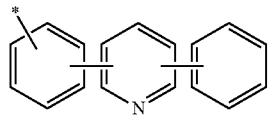

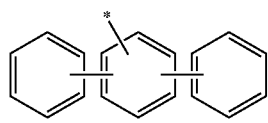

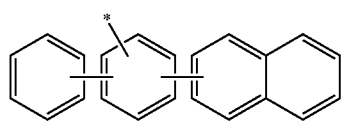

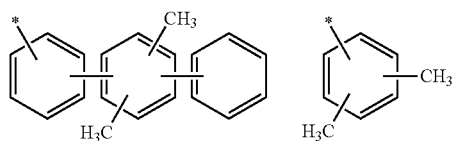

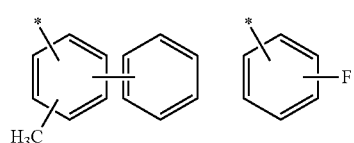

-continued

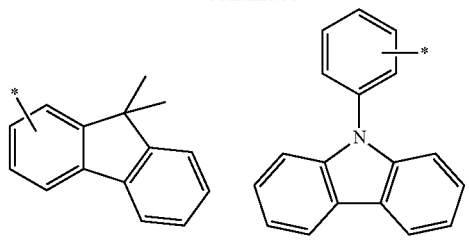

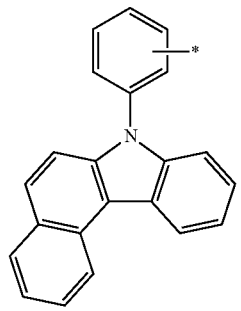

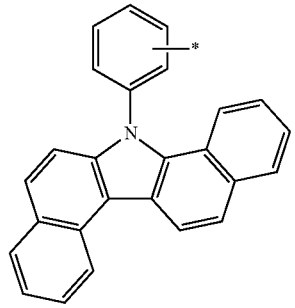

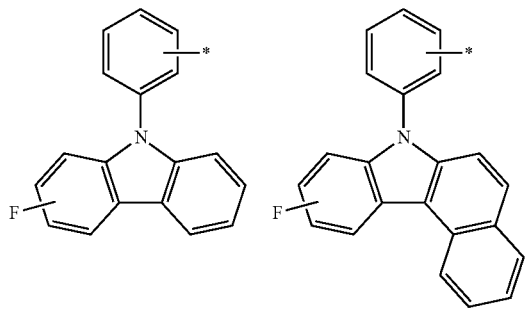

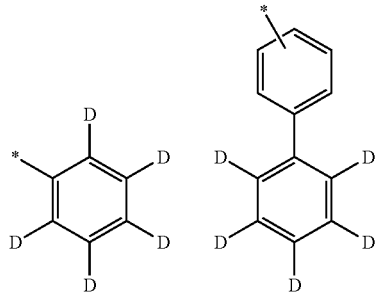

71
-continued
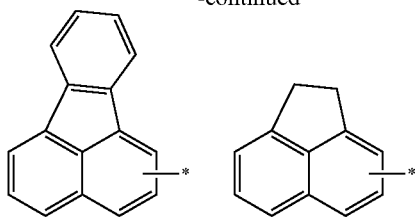
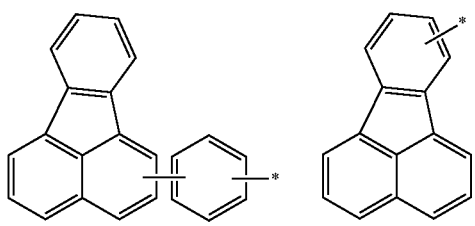
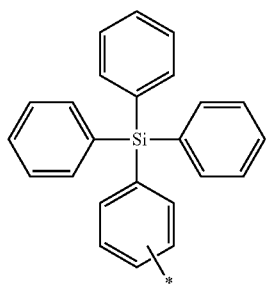
72
-continued
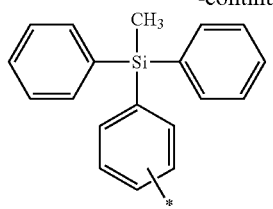
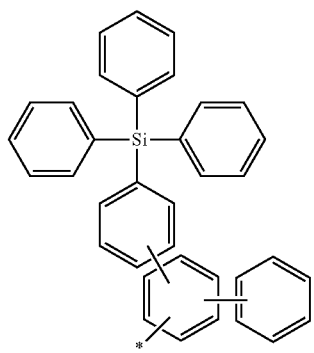
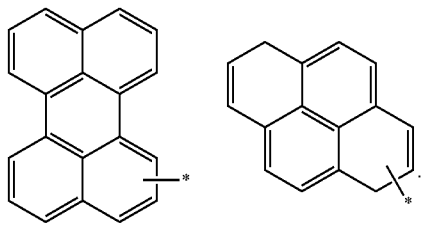
5. A compound selected from the group consisting of:
C-1
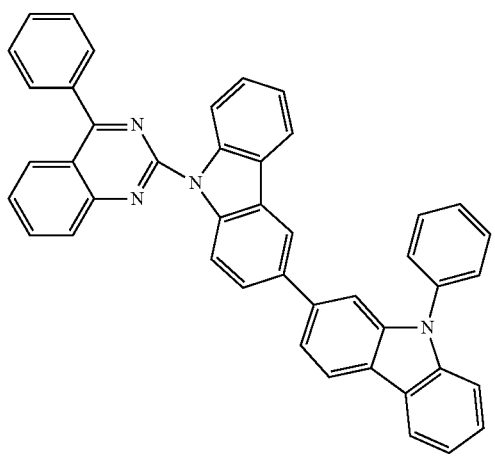
C-2
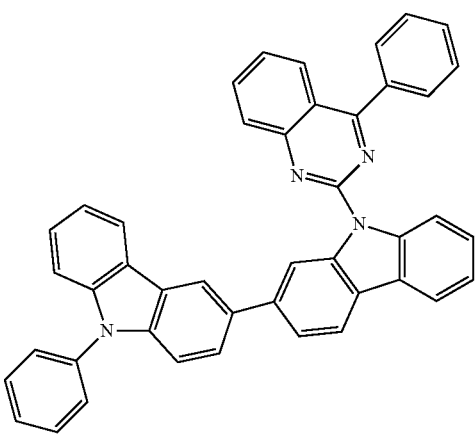

-continued
C-3
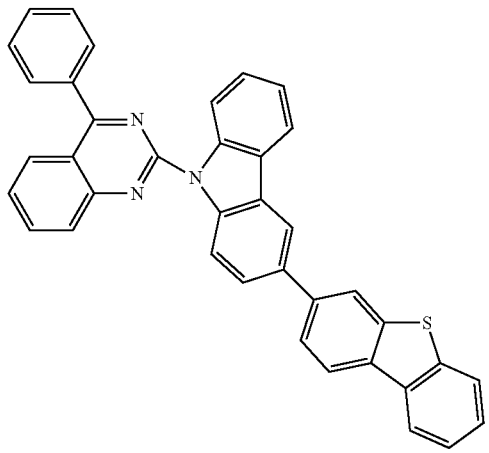
C-4
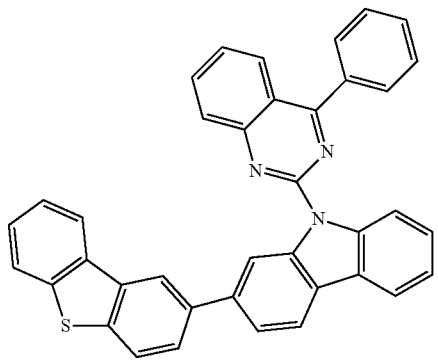
C-5
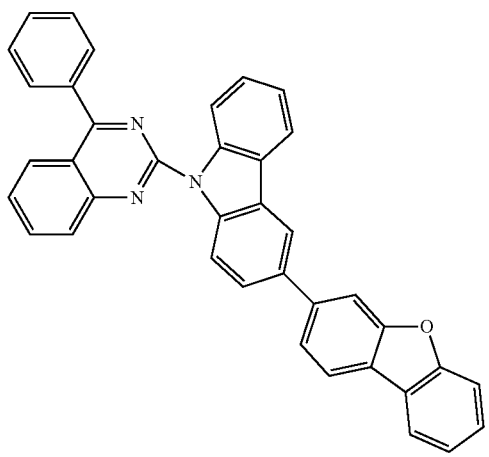
C-6
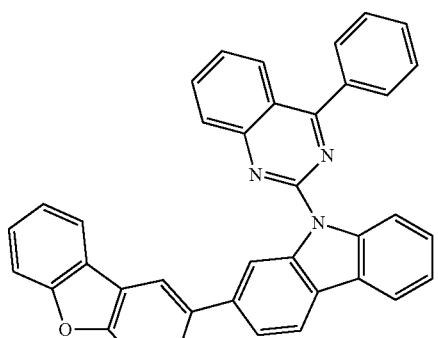
C-7
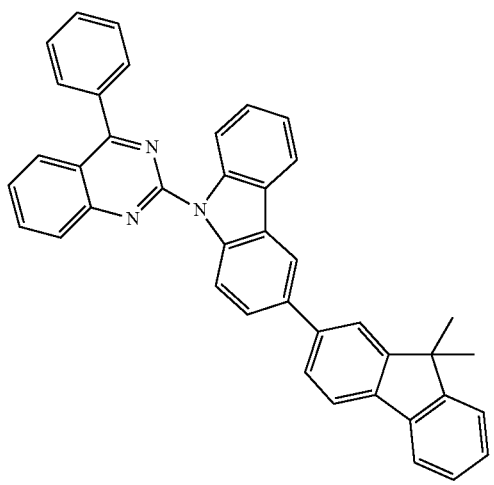
C-8
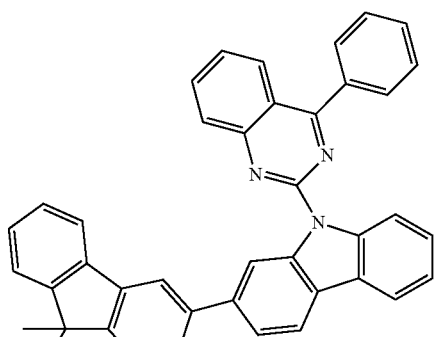

-continued
C-9
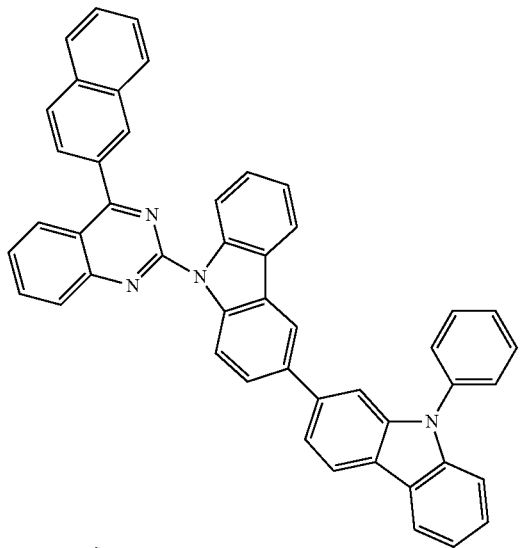
C-10
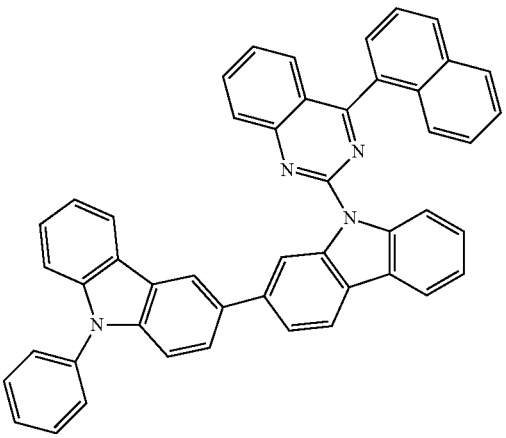
C-11
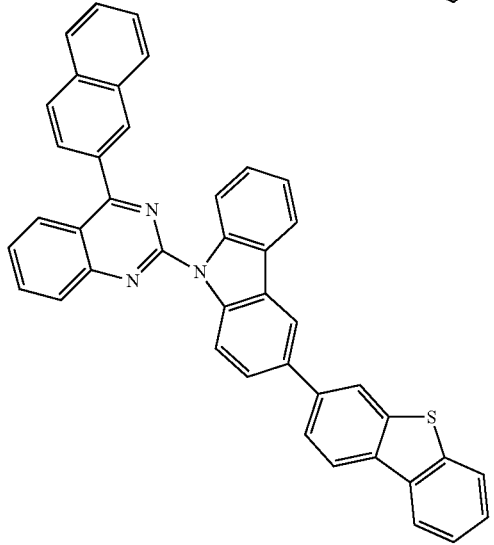
C-12
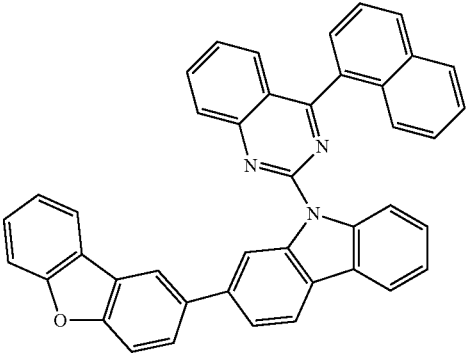
C-13
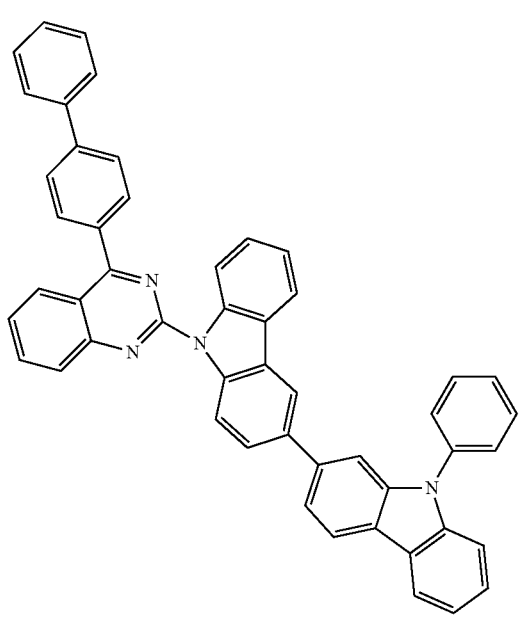
C-14
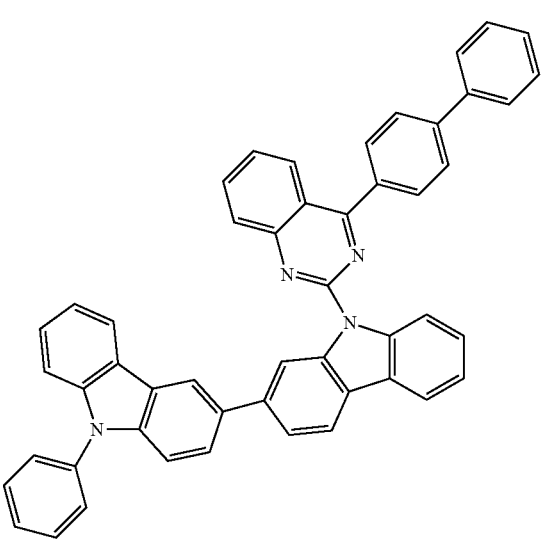

-continued
C-15
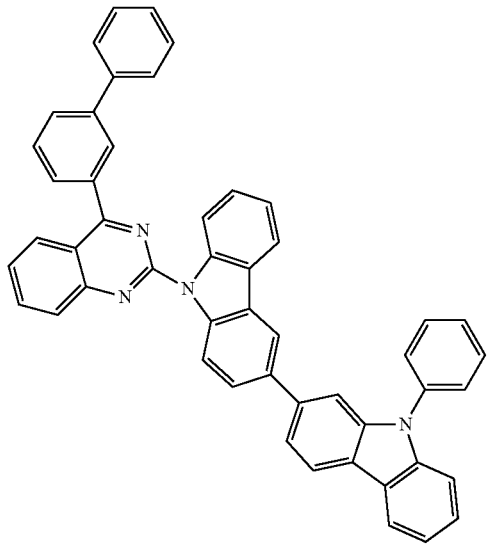
C-16
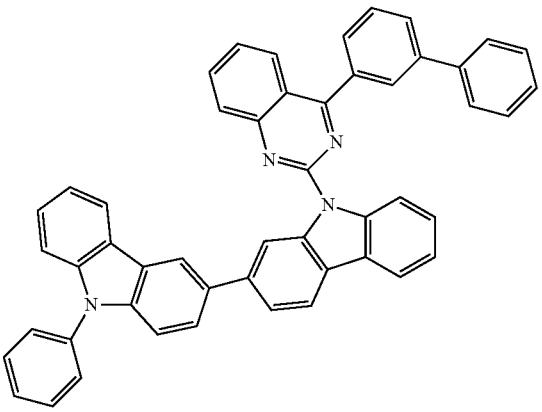
C-17
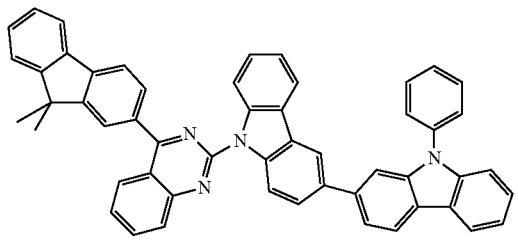
C-18
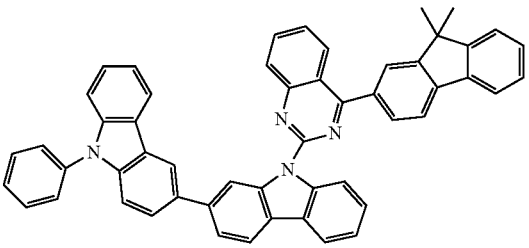
C-19
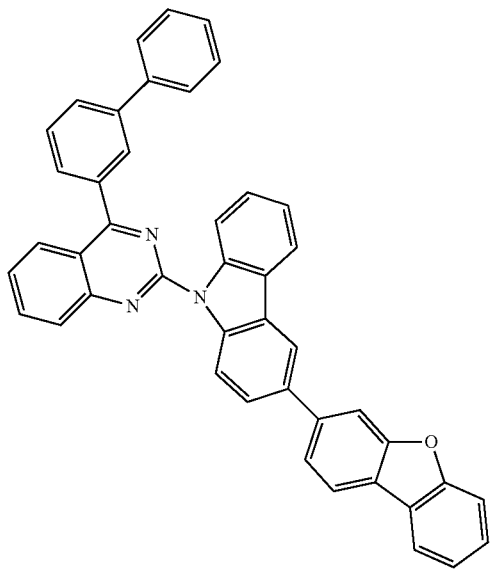
C-20
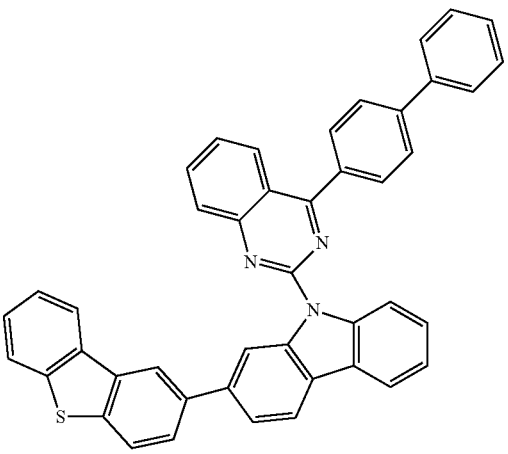
C-21
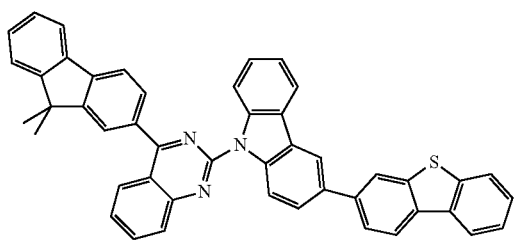
C-22
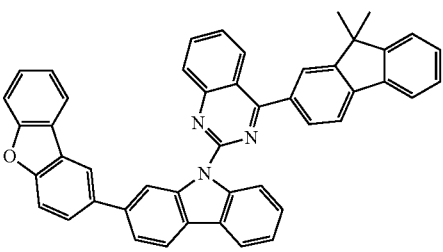

-continued
C-23
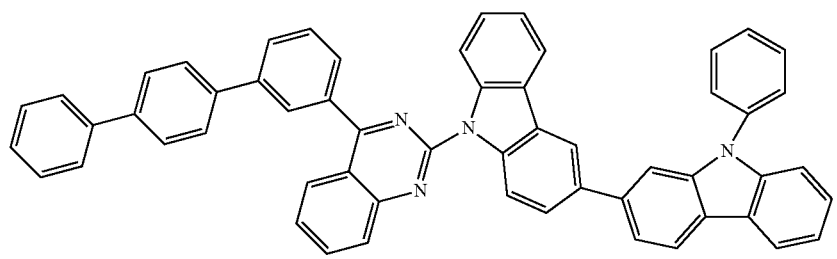
C-24
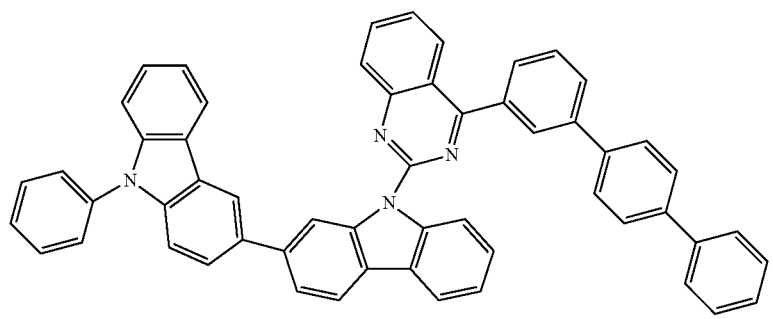
C-25
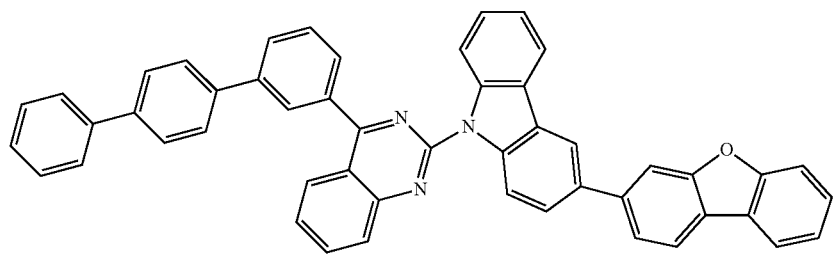
C-26
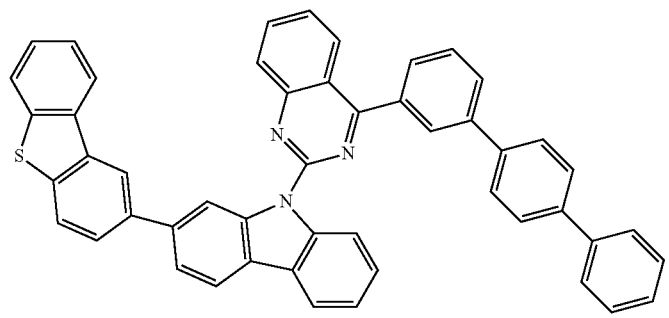
C-27
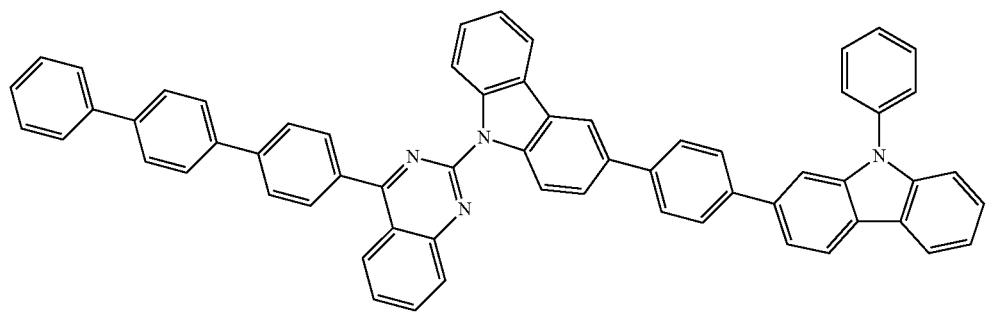

-continued
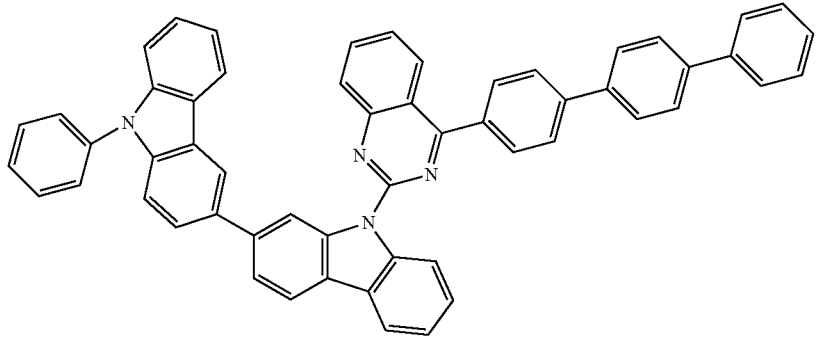
C-28
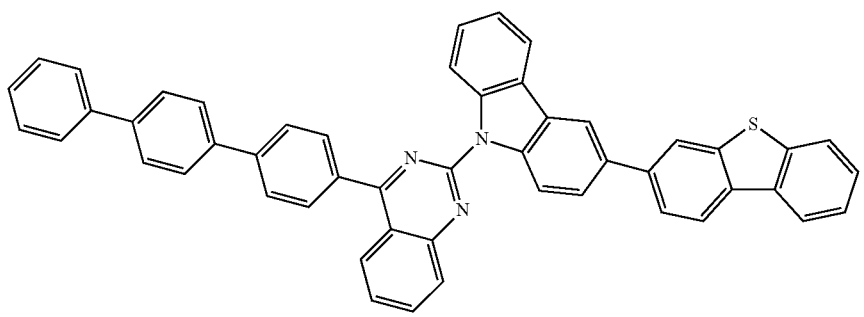
C-29
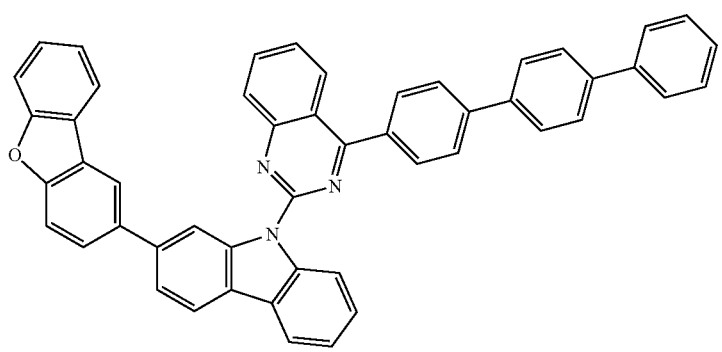
C-30
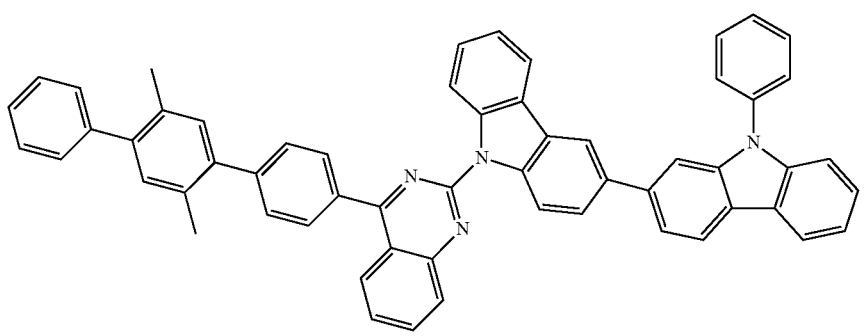
C-31

-continued
C-32
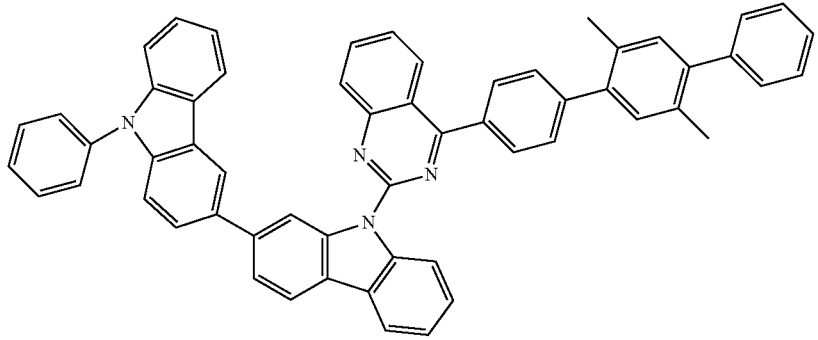
C-33 C-34
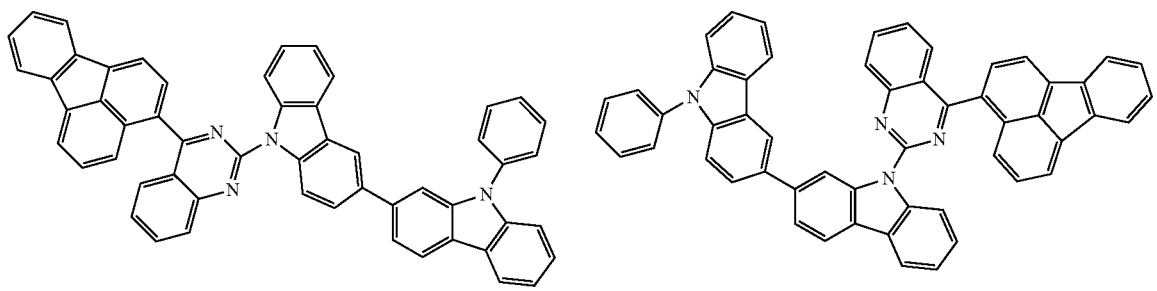
C-35 C-36
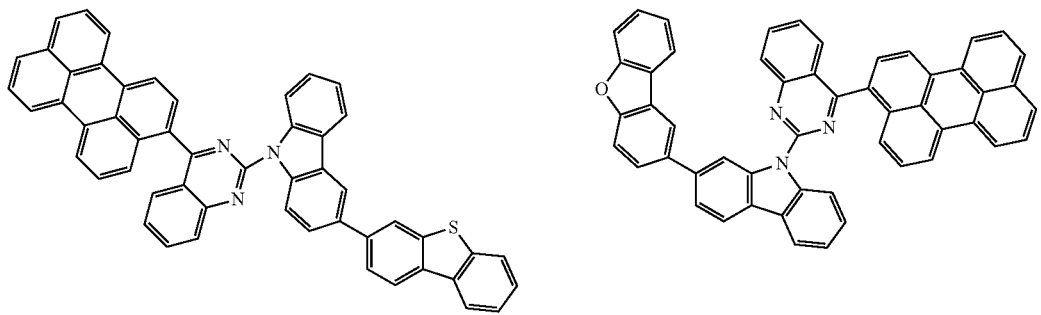
C-37 C-38
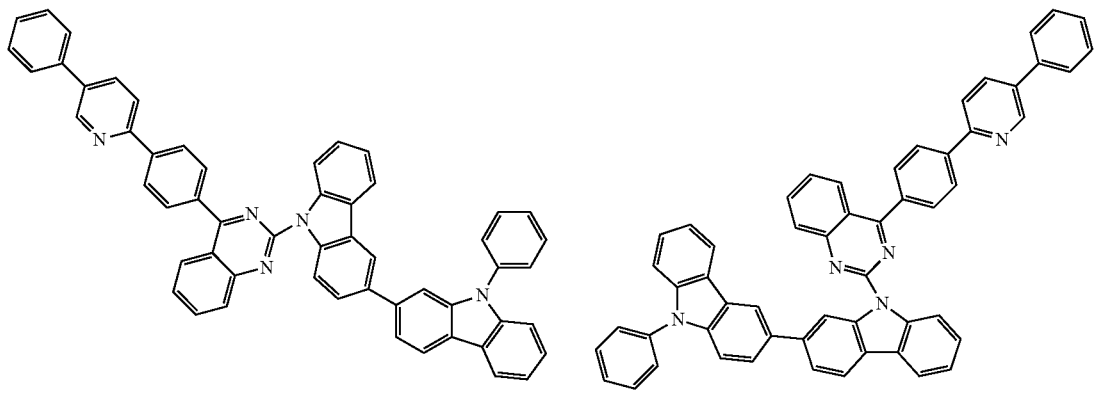

-continued
C-45
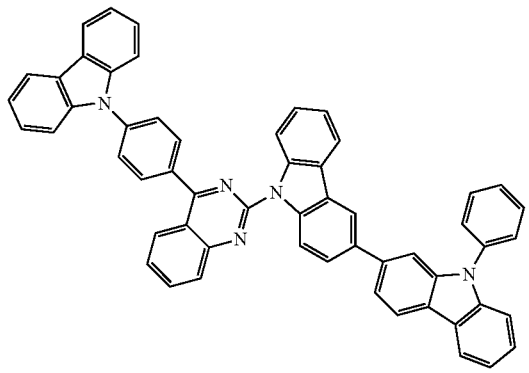
C-46
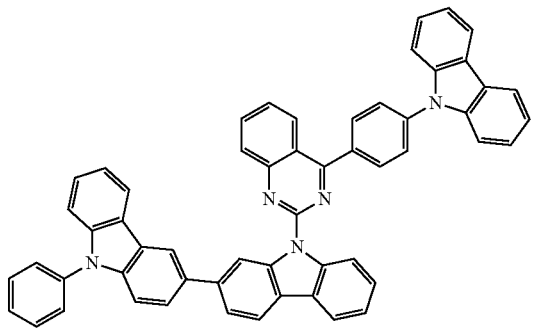
C-47
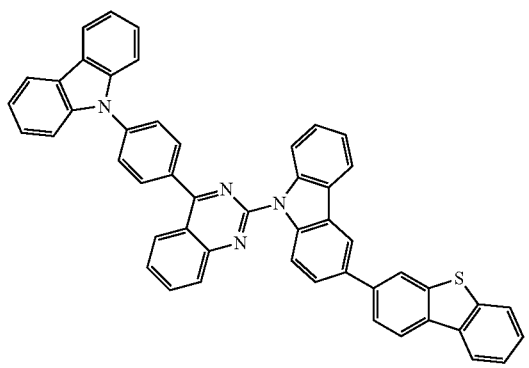
C-48
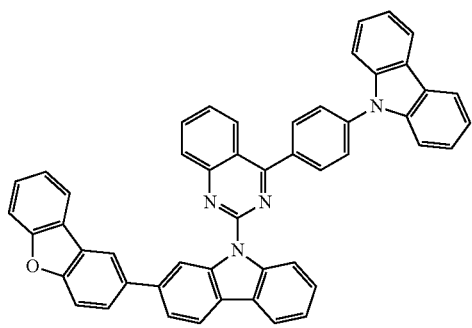
C-49
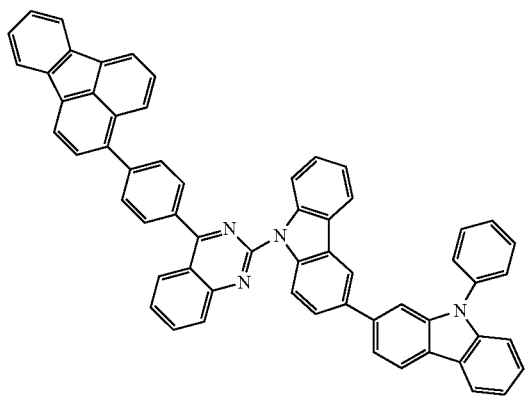
C-50
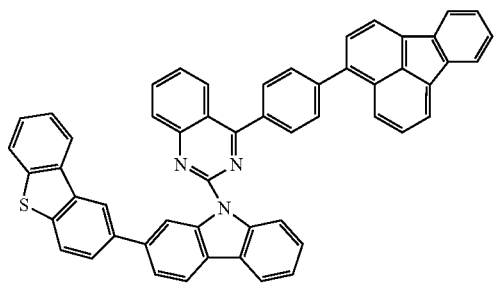
C-51
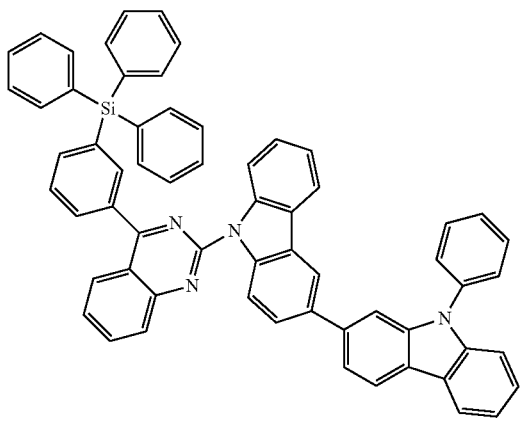
C-52
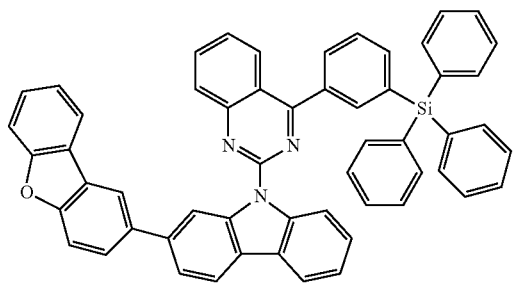

-continued
C-53
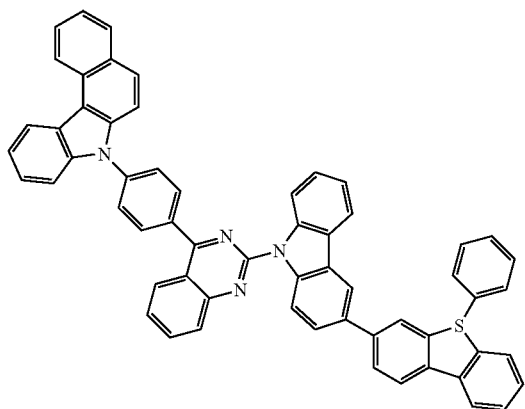
C-54
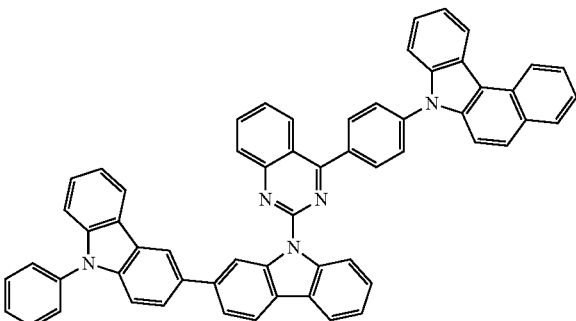
C-55
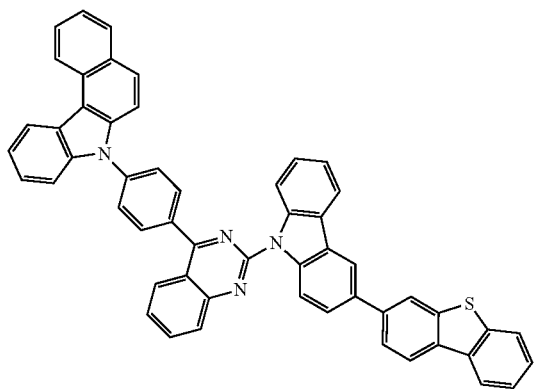
C-56
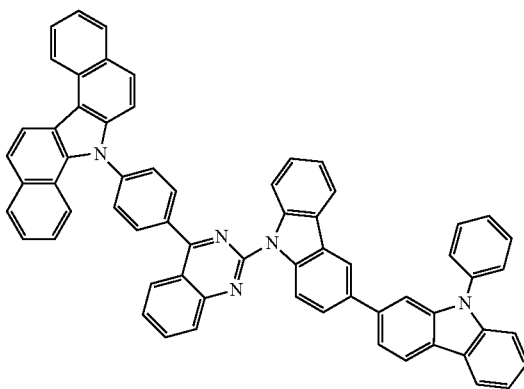
C-57
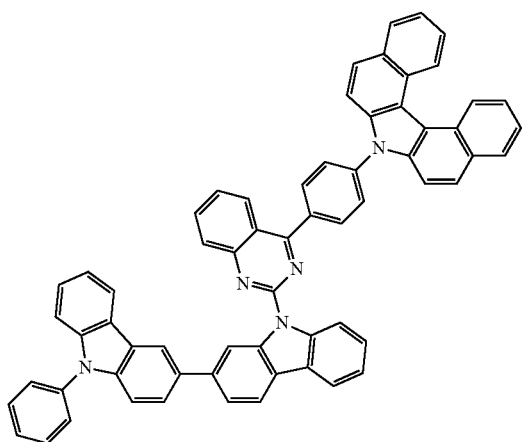
C-58
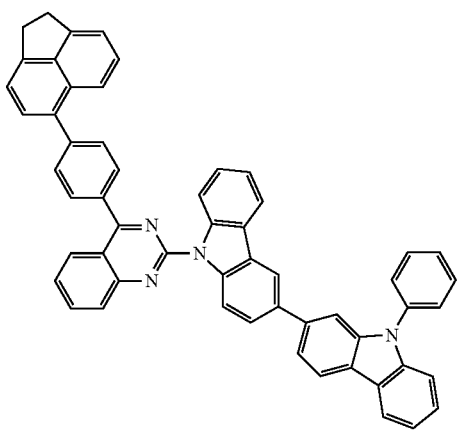

-continued
C-59
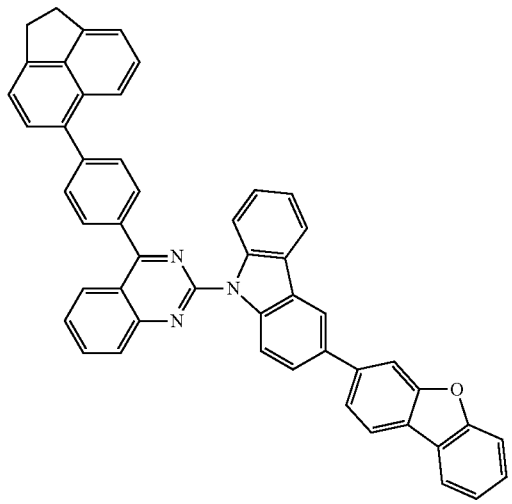
C-60
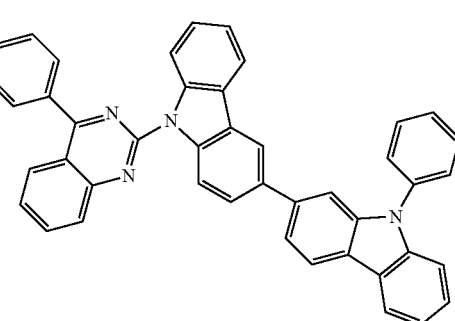
C-61
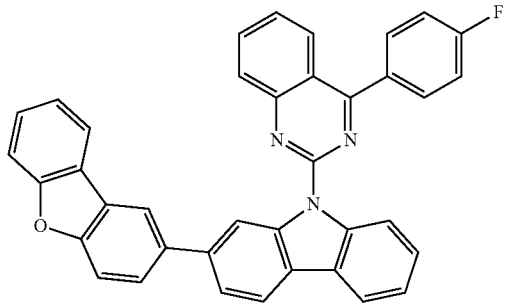
C-62
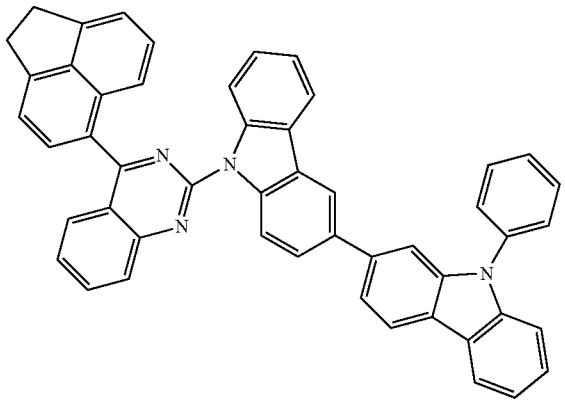
C-63
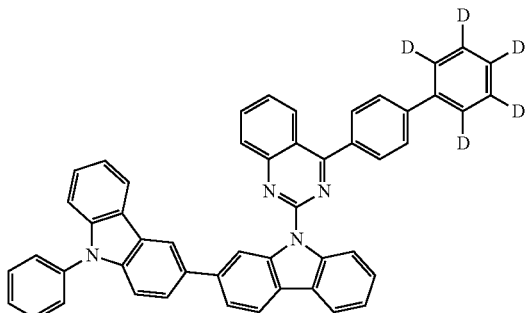
C-64
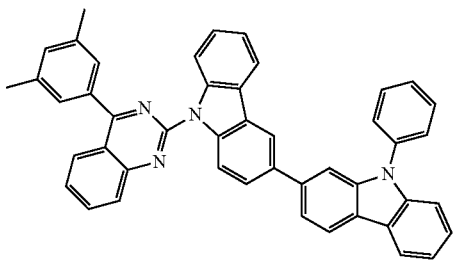
C-65
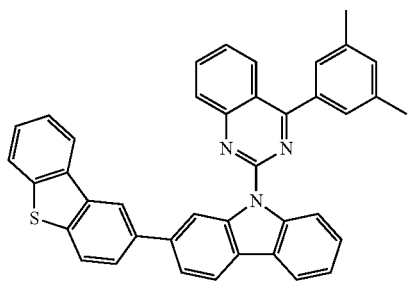
C-66
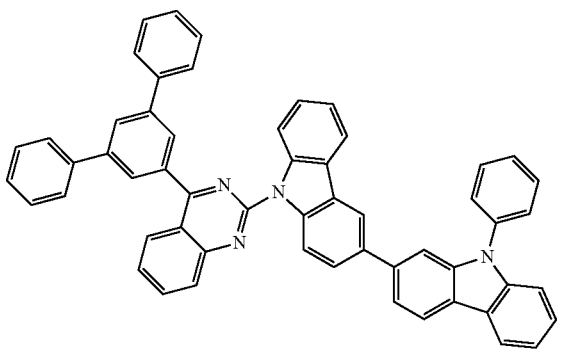

-continued
C-67
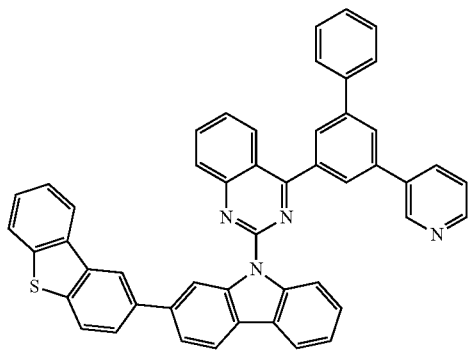
C-68
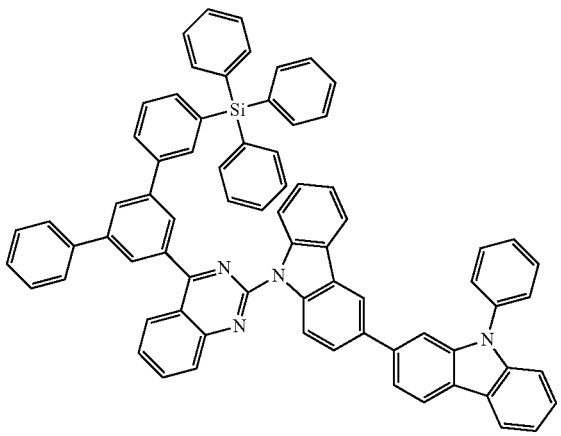
C-69
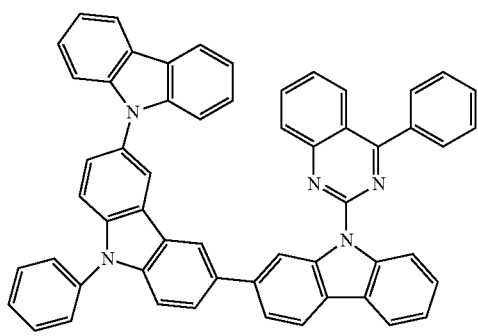
C-70
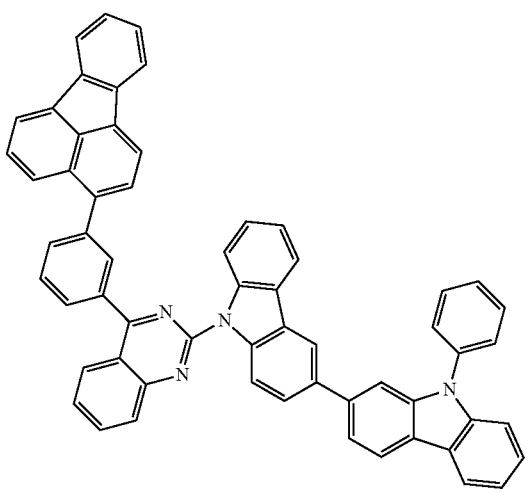
C-71
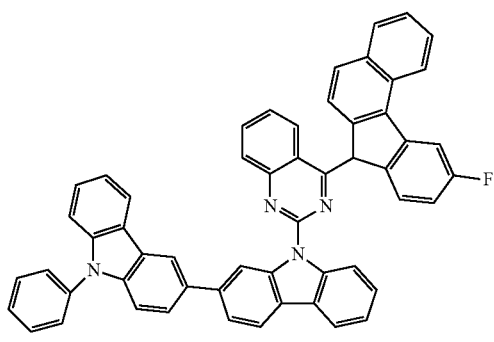
C-72
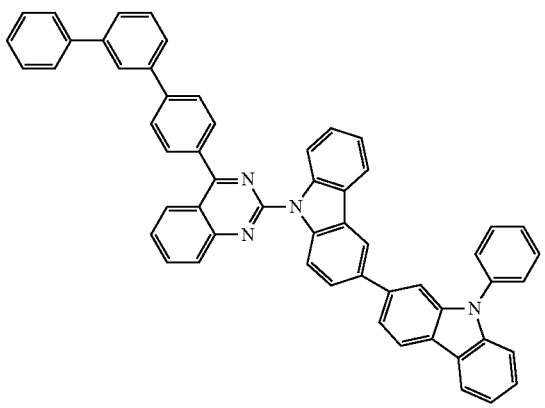

-continued
C-73
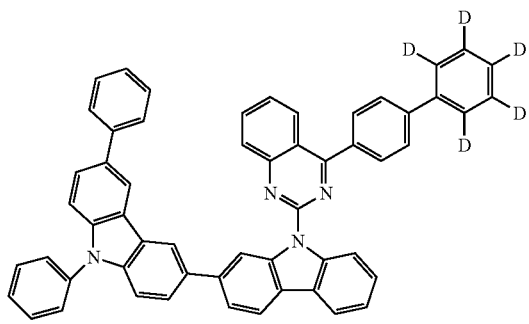
C-74
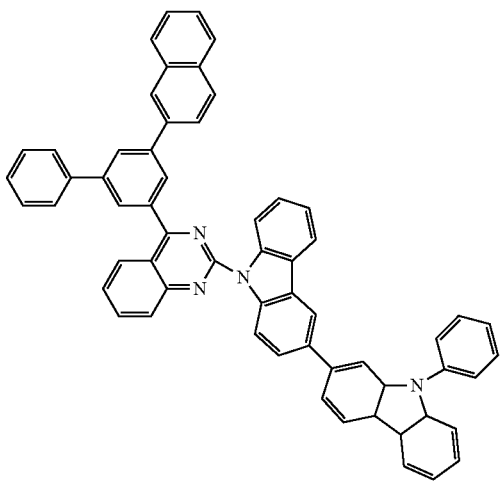
C-75
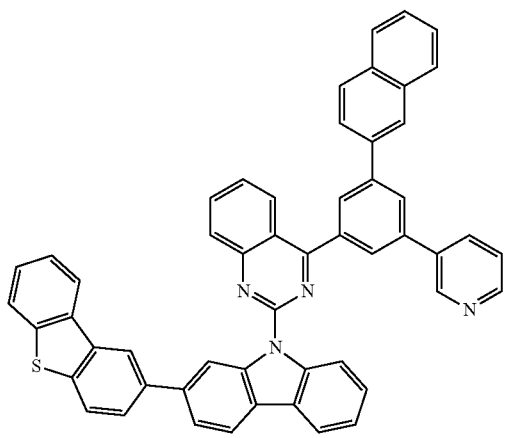
C-76
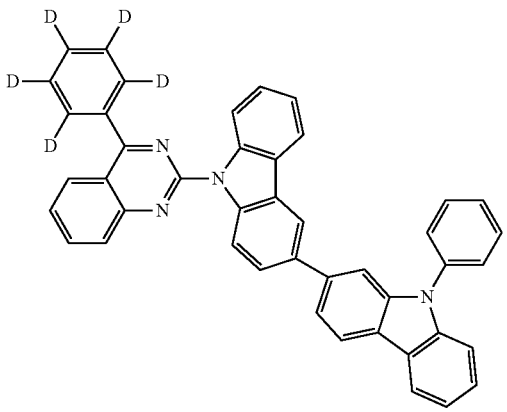
C-77
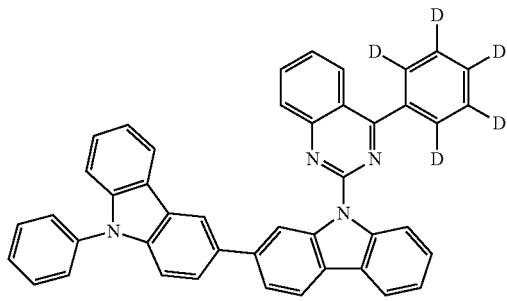
C-79
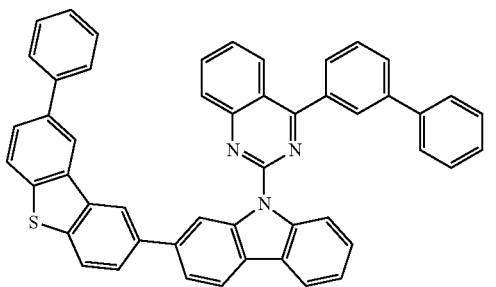
C-82
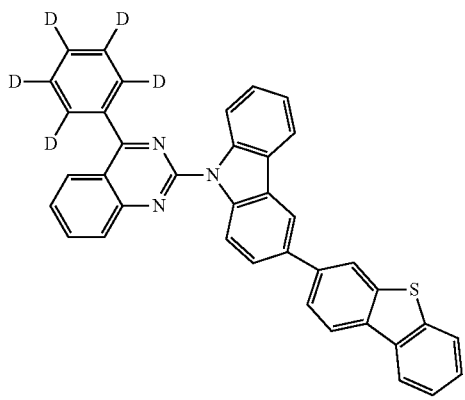
C-84
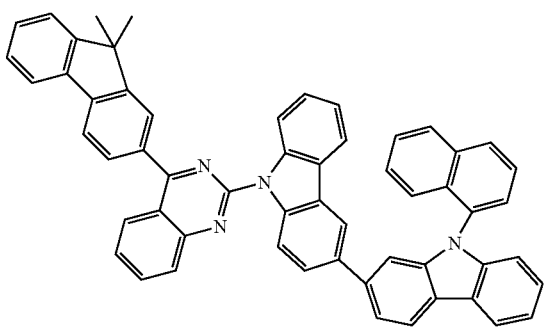

C-85
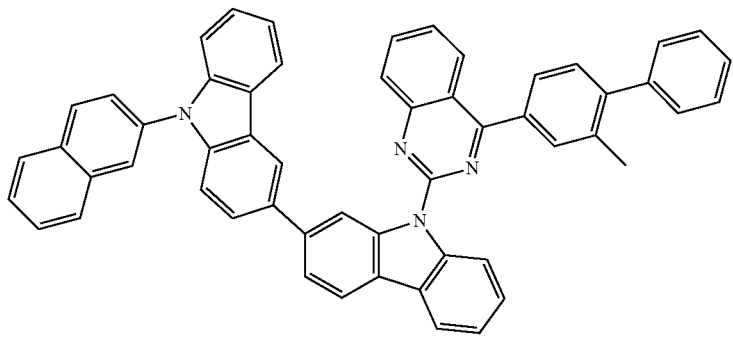
C-86
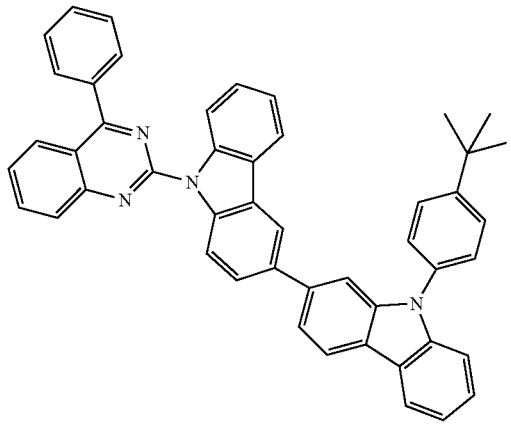
C-87
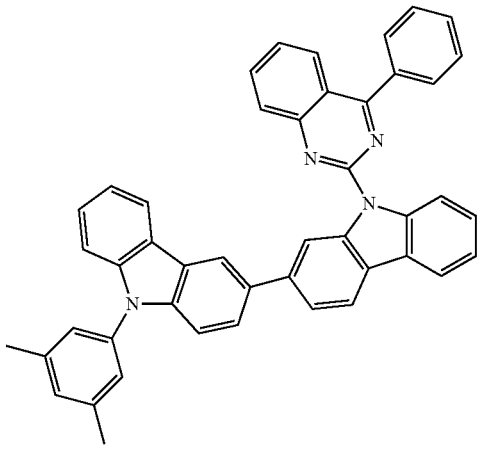
C-88
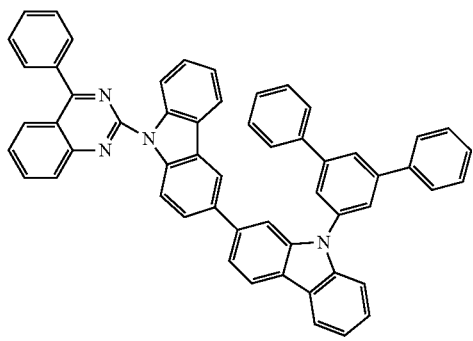
C-89
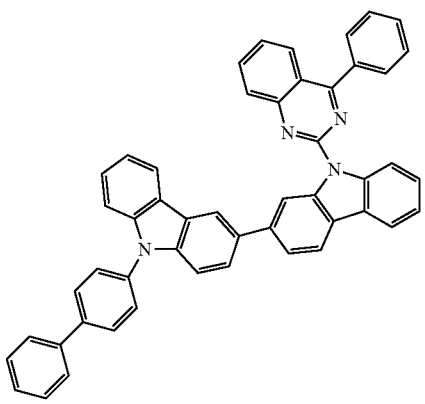
C-90
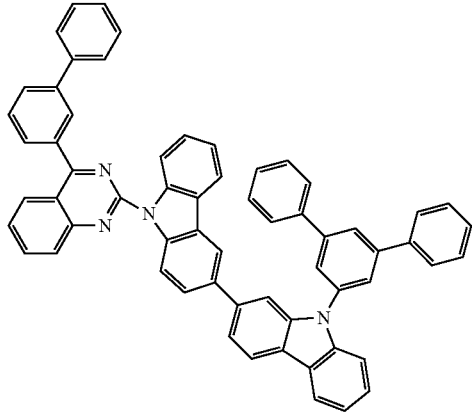
C-91
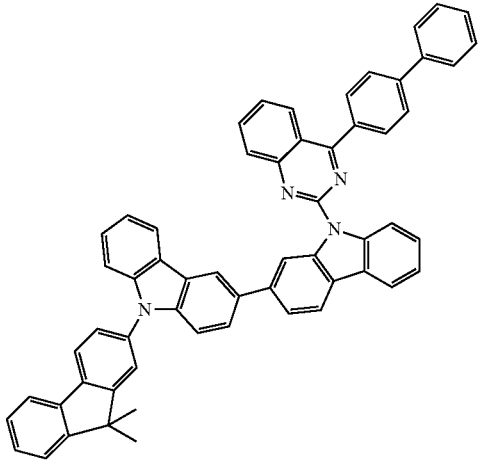

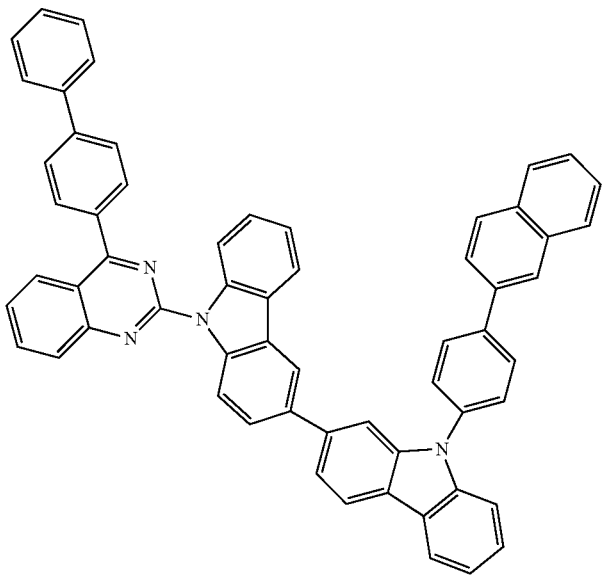
C-92
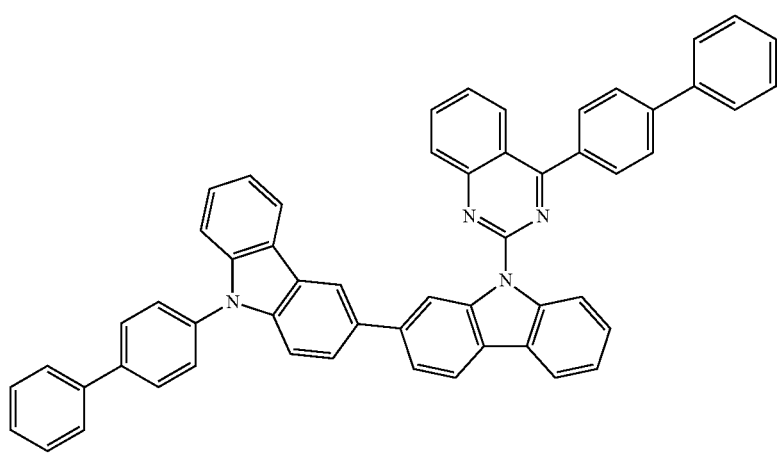
C-93
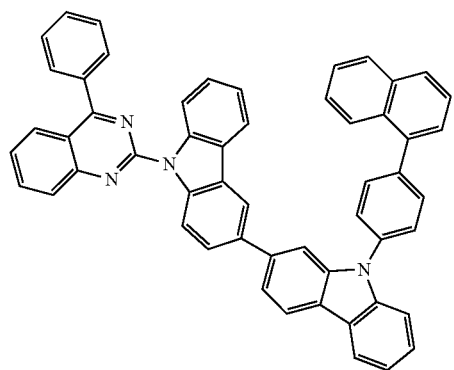
C-94
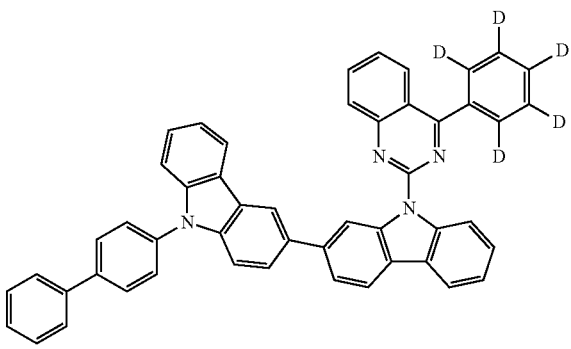
C-95

-continued
C-96
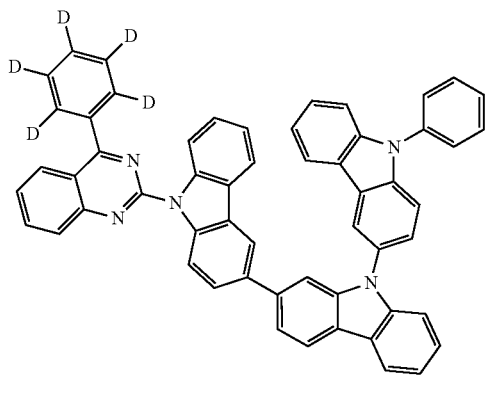
C-97
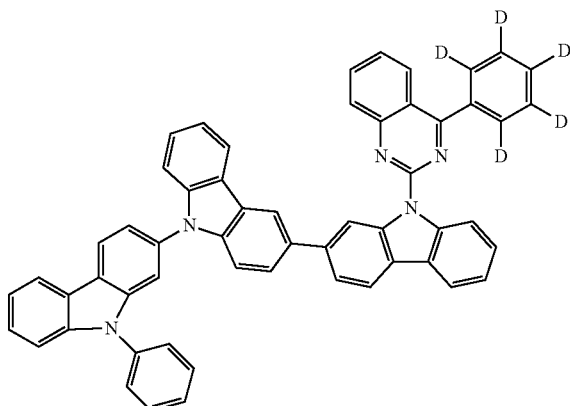
C-98
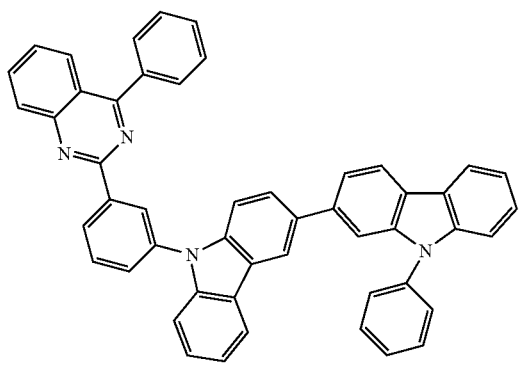
C-99
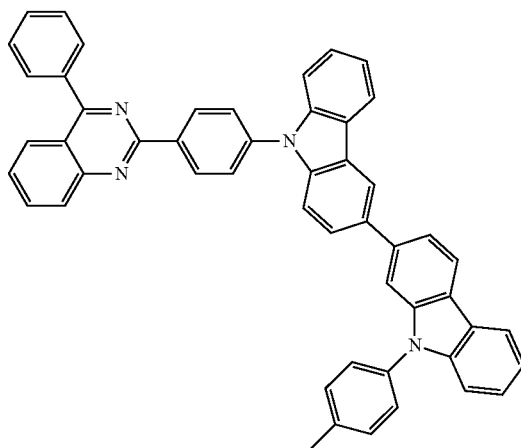
C-100
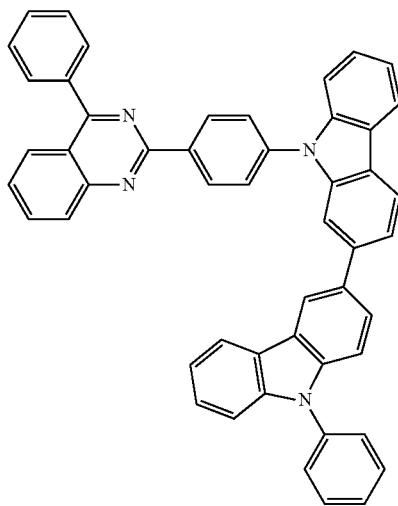
C-101
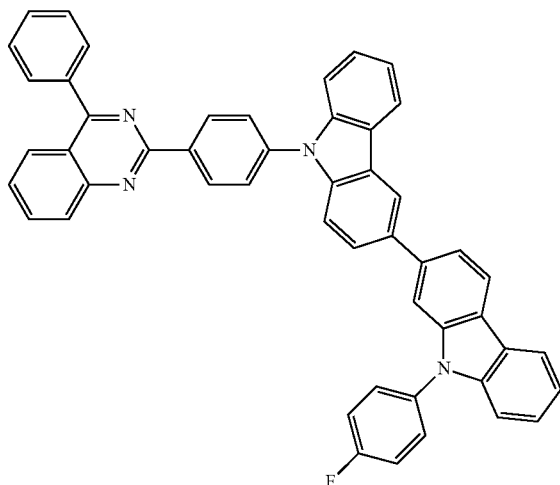

-continued
C-102
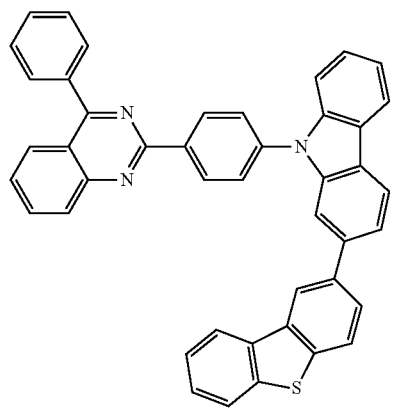
C-103
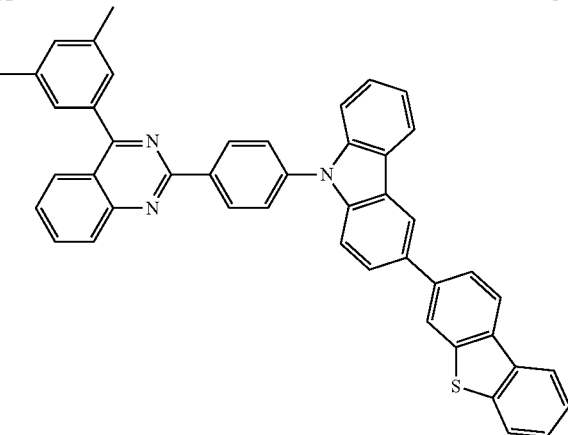
C-104
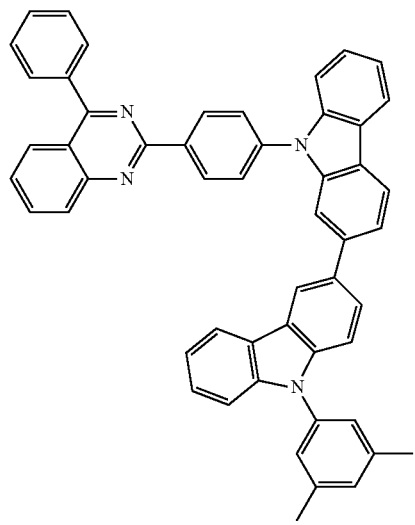
C-105
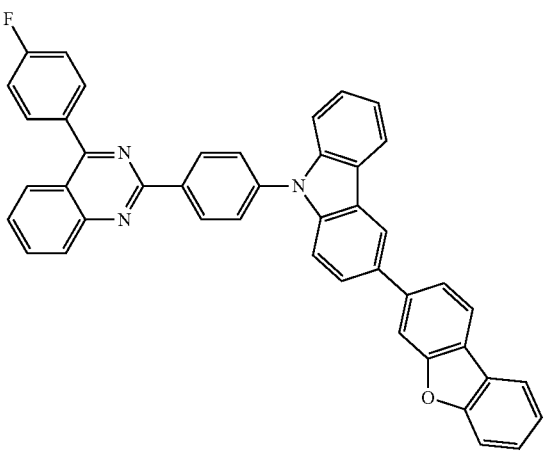
C-106
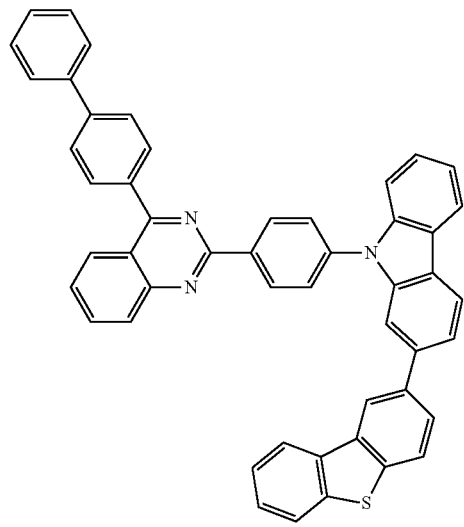
C-107
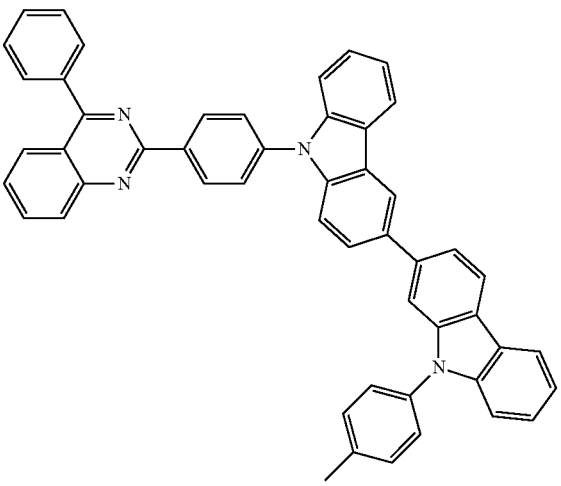

-continued
C-108
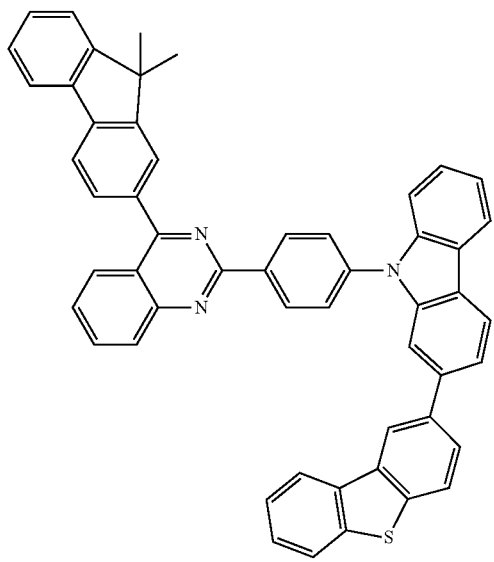
C-109
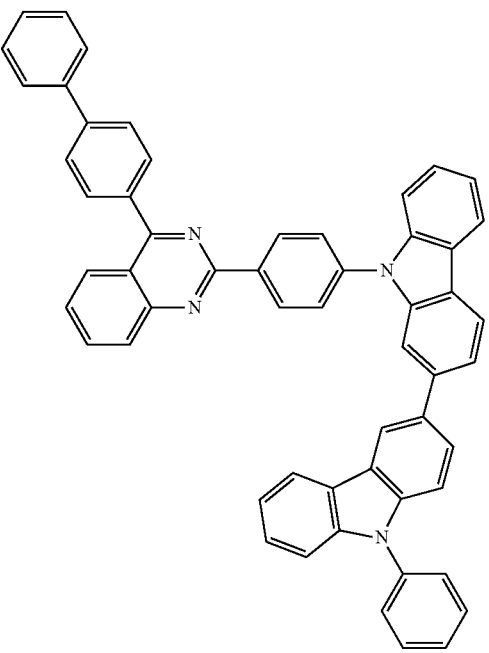
C-110
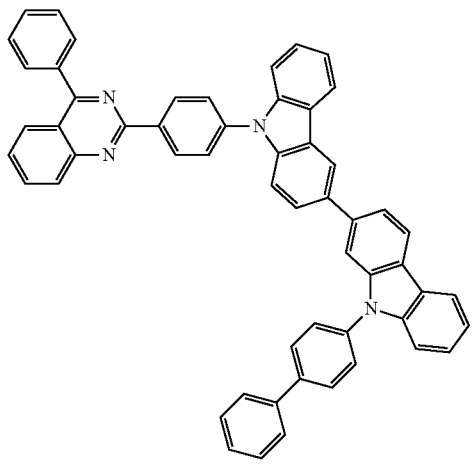
C-111
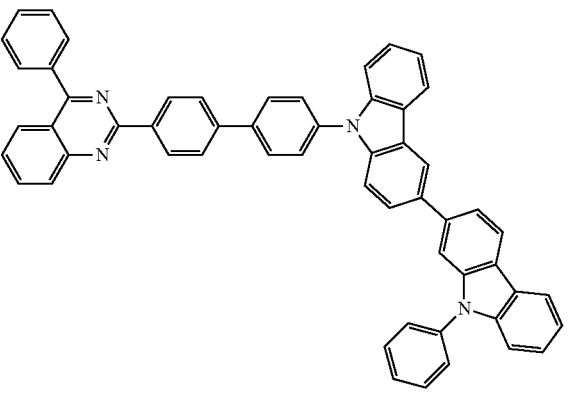
C-112
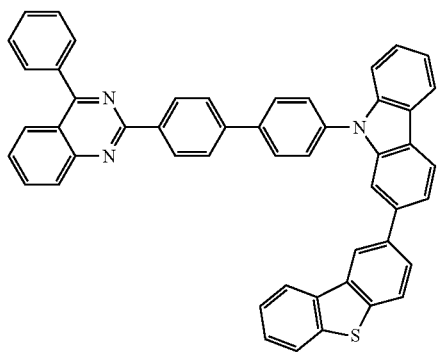
C-113
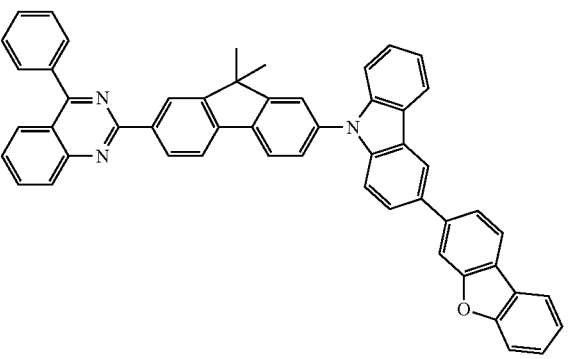

-continued
C-114
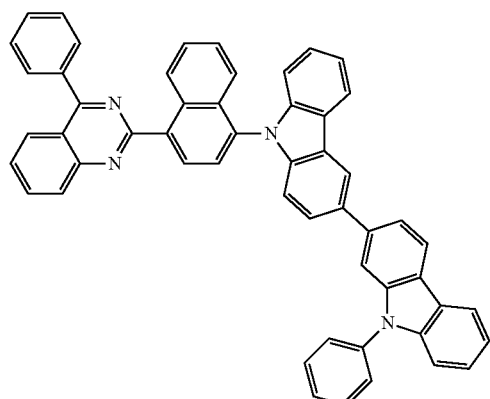
C-115
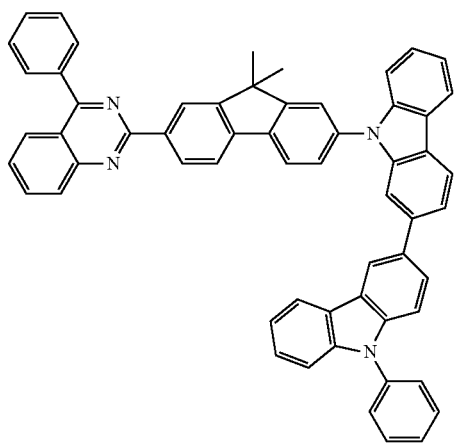
C-116
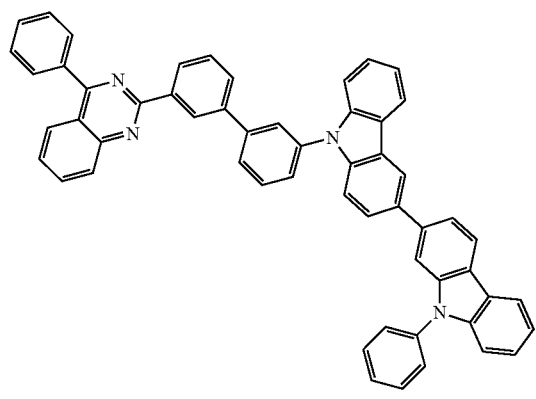
C-117
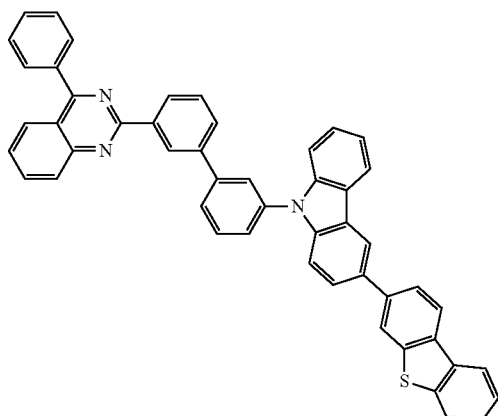
C-118
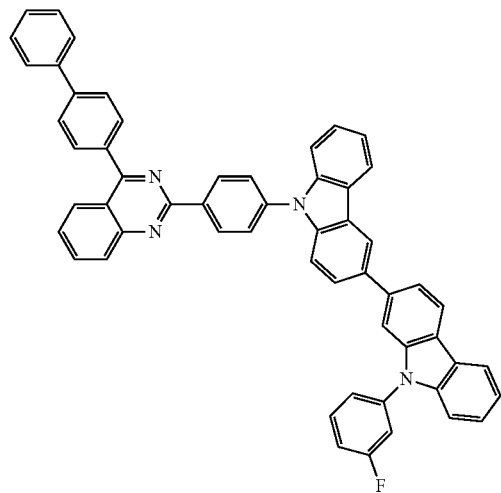
C-119
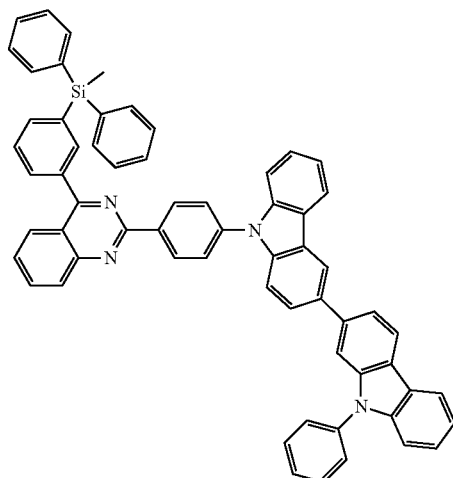

-continued
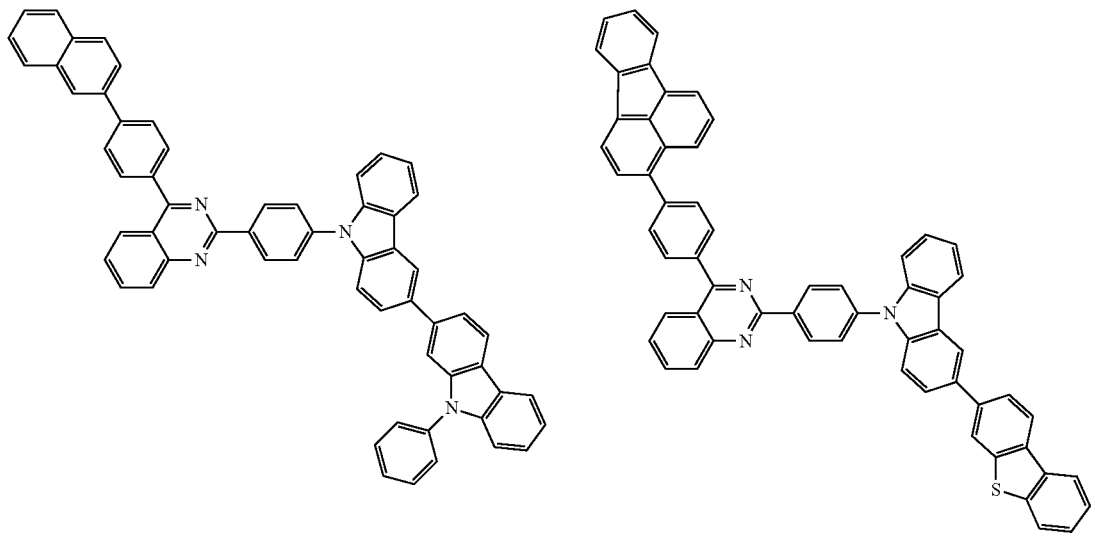
C-120
C-121
6. An organic electroluminescent device comprising the compound according to claim 1.
* * * * *